US008293881B2

(12) United States Patent
Seehra et al.

(10) Patent No.: US 8,293,881 B2
(45) Date of Patent: Oct. 23, 2012

(54) ISOLATED NUCLEIC ACID ENCODING A TRUNCATED ACTRIIB FUSION PROTEIN

(75) Inventors: Jasbir Seehra, Lexington, MA (US); Ravindra Kumar, Acton, MA (US)

(73) Assignee: Acceleron Pharma Inc., Cambridge, MA (US)

( * ) Notice: Subject to any disclaimer, the term of this patent is extended or adjusted under 35 U.S.C. 154(b) by 0 days.

(21) Appl. No.: 12/796,307

(22) Filed: Jun. 8, 2010

(65) Prior Publication Data

US 2010/0316644 A1   Dec. 16, 2010

Related U.S. Application Data

(60) Provisional application No. 61/268,420, filed on Jun. 12, 2009, provisional application No. 61/280,543, filed on Nov. 3, 2009.

(51) Int. Cl.
*C07H 21/04* (2006.01)
*C12N 15/09* (2006.01)
*C12N 5/02* (2006.01)

(52) U.S. Cl. ............... 536/23.4; 435/69.7; 435/325

(58) Field of Classification Search .............. None
See application file for complete search history.

(56) References Cited

U.S. PATENT DOCUMENTS

| | | | |
|---|---|---|---|
| 4,973,577 A | 11/1990 | Vale, Jr. et al. |
| 5,118,667 A | 6/1992 | Adams et al. |
| 5,658,876 A | 8/1997 | Crowley et al. |
| 5,808,007 A | 9/1998 | Lee et al. |
| 5,824,637 A | 10/1998 | Crowley et al. |
| 5,847,078 A | 12/1998 | Eto et al. |
| 5,885,794 A | 3/1999 | Mathews et al. |
| 6,004,780 A | 12/1999 | Soppet et al. |
| 6,093,547 A | 7/2000 | Jin et al. |
| 6,132,988 A | 10/2000 | Sugino et al. |
| 6,162,896 A | 12/2000 | Mathews et al. |
| 6,451,334 B2 | 9/2002 | Perrine |
| 6,599,876 B2 | 7/2003 | Kojima |
| 6,605,699 B1 | 8/2003 | Ni et al. |
| 6,656,475 B1 | 12/2003 | Lee et al. |
| 6,656,708 B1 | 12/2003 | Yu et al. |
| 6,692,925 B1 | 2/2004 | Miyazono et al. |
| 6,696,260 B1 | 2/2004 | Lee et al. |
| 6,777,205 B1 | 8/2004 | Carcagno et al. |
| 6,835,544 B2 | 12/2004 | Mathews et al. |
| 6,891,082 B2 | 5/2005 | Lee et al. |
| 7,192,717 B2 | 3/2007 | Hill et al. |
| 7,202,210 B2 | 4/2007 | Wolfman et al. |
| 7,261,893 B2 | 8/2007 | Veldman et al. |
| 7,320,789 B2 | 1/2008 | Aghajania et al. |
| 7,560,441 B2 | 7/2009 | Wolfman et al. |
| 7,612,041 B2 | 11/2009 | Knopf et al. |
| 7,988,973 B2 | 8/2011 | Sherman |
| 8,007,809 B2 | 8/2011 | Sherman |
| 2001/0039036 A1 | 11/2001 | Mathews et al. |
| 2003/0083251 A1 | 5/2003 | Westenfelder |
| 2003/0144203 A1 | 7/2003 | Bowen |
| 2004/0132675 A1 | 7/2004 | Kuo et al. |
| 2004/0138129 A1 | 7/2004 | MacLeod |
| 2004/0197828 A1 | 10/2004 | Gaddy |
| 2004/0209805 A1 | 10/2004 | Phillips et al. |
| 2004/0223966 A1 | 11/2004 | Wolfman et al. |
| 2005/0106148 A1 | 5/2005 | Kay et al. |
| 2005/0197292 A1 | 9/2005 | Smithson et al. |
| 2005/0244867 A1 | 11/2005 | Soppet et al. |
| 2005/0257278 A1 | 11/2005 | Lee et al. |
| 2006/0068468 A1 | 3/2006 | Knopf et al. |
| 2006/0210657 A1 | 9/2006 | Chou |
| 2007/0048830 A1 | 3/2007 | Gilbert et al. |
| 2007/0149455 A1 | 6/2007 | Wolfman et al. |
| 2007/0172956 A1 | 7/2007 | Magari et al. |
| 2007/0184052 A1 | 8/2007 | Lin et al. |
| 2007/0249022 A1 | 10/2007 | Knopf et al. |
| 2007/0275895 A1 | 11/2007 | Duan et al. |
| 2007/0292885 A1 | 12/2007 | Bejanin et al. |
| 2008/0021104 A1 | 1/2008 | Tarallo |
| 2008/0075692 A1 | 3/2008 | Perrine |
| 2008/0089897 A1 | 4/2008 | Wolfman |
| 2008/0102065 A1 | 5/2008 | Borges et al. |
| 2008/0139590 A1 | 6/2008 | Qian et al. |
| 2009/0005308 A1 | 1/2009 | Knopf et al. |
| 2009/0017019 A1 | 1/2009 | Shields et al. |
| 2009/0047281 A1 | 2/2009 | Sherman |
| 2009/0074768 A1 | 3/2009 | Knopf et al. |
| 2009/0087433 A1 | 4/2009 | Wolfman et al. |
| 2009/0098113 A1 | 4/2009 | Knopf et al. |

(Continued)

FOREIGN PATENT DOCUMENTS

WO        WO-92/20793 A1        11/1992

(Continued)

OTHER PUBLICATIONS

Bowie et al., 1990, Science 247: 1306-1310.*
Wells, 1990, Biochemistry 29:8509-8517.*
Cadena, S.M., et al., "Administration of a Soluble Activin Type IIB Receptor Promotes Skeletal Muscle Growth Independent of Fiber Type," Journal of Applied Physiology, 109:635-642 (2010).
Sako, D., et al., "Characterization of the Ligand Binding Functionality of the Extracellular Domain of Activin Receptor Type IIB," The Journal of Biological Chemistry, 285(27):21037-21048 (2010).
International Search Report for PCT/US2010/037787, dated Aug. 31, 2010.
"Recombinant Human Activin RIIA/Fc Chimera," R&D Systems 340-R2 (Aug. 27, 2003).

(Continued)

*Primary Examiner* — Gyan Chandra
(74) *Attorney, Agent, or Firm* — Ropes & Gray LLP

(57) ABSTRACT

In certain aspects, the present invention provides compositions and methods for modulating (promoting or inhibiting) growth of a tissue, such as bone, cartilage, muscle, fat, brown fat and/or neuronal tissue and for treating metabolic disorders such as diabetes and obesity, as well as disorders associated with any of the foregoing tissue.

9 Claims, 34 Drawing Sheets
(32 of 34 Drawing Sheet(s) Filed in Color)

U.S. PATENT DOCUMENTS

| | | |
|---|---|---|
| 2009/0099086 A1 | 4/2009 | Knopf et al. |
| 2009/0118188 A1 | 5/2009 | Knopf et al. |
| 2009/0142333 A1 | 6/2009 | Knopf et al. |
| 2009/0148436 A1 | 6/2009 | LaVallie et al. |
| 2009/0163417 A1 | 6/2009 | Sherman |
| 2010/0068215 A1 | 3/2010 | Seehra et al. |
| 2010/0183624 A1 | 7/2010 | Seehra et al. |
| 2010/0272734 A1 | 10/2010 | Berger et al. |

FOREIGN PATENT DOCUMENTS

| | | |
|---|---|---|
| WO | WO 94/15965 A1 | 7/1994 |
| WO | WO-95/10611 A1 | 4/1995 |
| WO | WO-95/29685 A1 | 11/1995 |
| WO | WO 9723613 A2 | 7/1997 |
| WO | WO-99/06559 A1 | 2/1999 |
| WO | WO-00/43781 A2 | 7/2000 |
| WO | WO-02/10214 A2 | 2/2002 |
| WO | WO-02/43759 A2 | 6/2002 |
| WO | WO-02/085306 A2 | 10/2002 |
| WO | WO 02094852 A2 | 11/2002 |
| WO | WO-03/006057 A1 | 1/2003 |
| WO | WO-03/053219 A2 | 7/2003 |
| WO | WO-03/072808 A1 | 9/2003 |
| WO | WO-2004/039948 | 5/2004 |
| WO | WO-2004/108157 A2 | 12/2004 |
| WO | WO 2005003158 A2 | 1/2005 |
| WO | WO-2005/009460 | 2/2005 |
| WO | WO 2005014650 A2 | 2/2005 |
| WO | WO-2005/028517 | 3/2005 |
| WO | WO 2005070967 A2 | 8/2005 |
| WO | WO-2005/094871 A2 | 10/2005 |
| WO | WO-2005/097825 A2 | 10/2005 |
| WO | WO-2006/002387 A2 | 1/2006 |
| WO | WO-2006/012627 A2 | 2/2006 |
| WO | WO-2006/020884 A2 | 2/2006 |
| WO | WO-2006/039400 A2 | 4/2006 |
| WO | WO-2006/083183 A1 | 8/2006 |
| WO | WO-2006/088972 | 8/2006 |
| WO | WO 2007038703 A2 | 4/2007 |
| WO | WO-2007/053775 A1 | 5/2007 |
| WO | WO-2007/062188 | 5/2007 |
| WO | WO-2007/067616 A2 | 6/2007 |
| WO | WO-2007/076127 A2 | 7/2007 |
| WO | WO-2008/031061 | 3/2008 |
| WO | WO-2008/060139 A1 | 5/2008 |
| WO | WO-2008/076437 A2 | 6/2008 |
| WO | WO 2008072723 A1 | 6/2008 |
| WO | WO-2008/097541 A2 | 8/2008 |
| WO | WO-2008/100384 A2 | 8/2008 |
| WO | WO 2008094708 A2 | 8/2008 |
| WO | WO-2008/109167 A2 | 9/2008 |
| WO | WO-2008/151078 A1 | 12/2008 |
| WO | WO-2009/009059 A1 | 1/2009 |
| WO | WO-2009/019504 A1 | 2/2009 |
| WO | WO-2009/019505 A2 | 2/2009 |
| WO | WO 2009025651 A1 | 2/2009 |
| WO | WO-2009/137613 A2 | 11/2009 |
| WO | WO 2009137075 A1 | 11/2009 |
| WO | WO-2009/158015 A2 | 12/2009 |
| WO | WO-2009/158025 A2 | 12/2009 |
| WO | WO-2010/019261 A1 | 2/2010 |
| WO | WO-2010/083034 A1 | 7/2010 |

OTHER PUBLICATIONS

"Recombinant Human Activin RIIB/Fc Chimera," R&D Systems 339-RB/CF (Aug. 27, 2003).

Acceleron Pharma Presents Positive Phase 1 Results Demonstrating ACE-011 Increases Markers of Bone Formation, Acceleron Pharma, pp. 1-2, <www.acceleronpharma.com/contents/news/press-releases/detail.jsp/q/news-id/47> Downloaded from the Internet on Feb. 17, 2009.

Akel et al, "Neutralization of Autocrine Transforming Growth Factor -β in Human Cord Blood CD34+ CD38− Lin− Cells Promotes Stem-Cell-Factor-Mediated Erythropoietin-Independent Early Erythroid Progenitor Development and Reduces Terminal Differentiation." Stem Cells, 21:557-567 (2003).

Akpan, I., et al., "The effects of a soluble activin type IIB receptor on obesity and insulin sensitivity," International Journal of Obesity, 33(11):1265-1273 (2009).

Allendorph, G.P., et al., "Structure of the ternary signaling complex of a TGF-β superfamily member," PNAS, 103(20):7643-7648 (2006).

Banks, G.B., et al., "The Value of Mammalian Models for Duchenne Muscular Dystrophy in Developing Therapeutic Strategies," Current Topics in Developmental Biology, 84:431-453 (2008).

Berenson, J.R., "Multiple Myeloma," Multiple Myeloma: Plasma Cell Disorders: Merck Manual Professional (2008). Downloaded from the internet on Sep. 17, 2010. <http://www.merk.com/mmpe/print/sec11/ch144/ch144e.html> pp. 1-5.

Bodey, B., et al., "Failure of Cancer Vaccines: The Significant Limitations of this Approach to Immunotherapy," Anticancer Research, 20:2665-2676 (2000).

Bogdanovich, S., et al., "Functional improvement of dystrophic muscle by myostatin blockade," Nature, 420:418-421 (2002).

Broxmeyer, H.E., et al, "Selective and indirect modulation of human multipotential and erythroid hematopoietic progenitor cell proliferation by recombinant human activin and inhibin," Proc. Natl. Acad. Sci. USA, 85:9052-9056 (1988).

Burdette et al., "Activin A mediates growth inhibition and cell cycle arest through Smads in human breast cancer cells." Cancer Research, 65(17):7968-7975; Abstract (2005).

Centrella et al., "Activin-A Binding and Biochemical Effects in Osteoblast-Enriched Cultures from Fetal-Rat Parietal Bone," Molecular and Cellular Biology, 11(1):250-58 (1991).

Chamberlain, R.S., et al., "Innovations and strategies for the development of anticancer vaccines," Expert Opinion on Pharmacotherapy, 1(4):603-614 (2000).

Chen, Y.G., et al. "Regulation of Cell Proliferation, Apoptosis, and Carcinogenesis by Activin," Exp. Biol. Med., 227(2):75-87 (2002).

Cirillo et al., "Hematocrit, blood pressure, and hypertension. The Gubbio Population Study." Hypertension, 20(3):319-326 (1992).

Coerver, et al., "Activin Signaling through Activin Receptor Type II Causes the Cachexia-Like Symptoms in Inhibin-Deficent Mice," 10(5):534-543 (1996).

Collins, C.D., "Multidisciplinary Symposium: Haematological Malignancies," Cancer Imaging 5:S119-S126 (2005).

Colman, P.M., et al., "Effects of amino acid sequence changes on antibody-antigen interactions," Research of Immunology, 145(1):33-36 (1994).

Daluiski et al., "Bone Morphogenetic Protein-3 is a Negative Regulator of Bone Density," Nature Genetics, 27:84-88 (2001).

Deconinck, N., et al., "Pathophysiology of Duchenne Muscular Dystrophy: Current Hypotheses," Pediatr. Neurol., 36:1-7 (2007).

del Re et al., "Reconstitution and Analysis of Soluble Inhibin and Activin Receptor Complexes in a Cell-free System," The Journal of Biological Chemistry, 279(51):53126-53135 (2004).

Donaldson, et al., "Activin and inhibin binding to the soluble extracellular domain of activin receptor II", Endocrinology 140(4):1760-1766 (1999).

Donaldson, et al., "Molecular Cloning and Binding Properties of the Human Type II Activin Receptor", Biochemical and Biophysical Research Communications, 184(1):310-316 (1992).

Fafioffe, et al.,"Activin and inhibin receptor gene expression in the ewe pituitary throughout the oestrous cycle," Journal of Endocrinology, 182:55-68 (2004).

Frigon, N.L., et al, "Regulation of Globin Gene Expression in Human K562 Cells by Recombinant Activin A," Blood, 79(3):765-772 (1992).

Fuller et al., "Activin A Is an Essential Cofactor for Osteoclast Induction," Biochemical and Biophysical Research Communications, 268:2-7 (2000).

Funaba et al., "Expression and Localization of Activin Receptors During Endochondral Bone Development," European Journal of Endocrinology, 144:63-71 (2001).

Gaddy-Kurten et al., "Inhibin Suppresses and Activin Stimulates Osteoblastogenesis and Osteoclastogenesis in Murine Bone Marrow Cultures," Endocrinology, 143(1):74-83 (2002).

Gamer et al., "BMP-3 is a Novel Inhibitor of Both Activin and BMP-4 Signaling in *Xenopus* Embryos," Developmental Biology, 285:156-168 (2005).

Ge, G., et al., "GDF11 Forms a Bone Morphogenetic Protein 1-Activated Latent Complex That Can Modulate Nerve Growth Factor-Induced Differentiation of PC12 Cells", Molecular and Cellular Biology, 25(14):5846-5858 (2005).

GenBank NM_001106, *Homo sapiens* activin A receptor, type IIB (ACVR2B), mRNA, http://www.ncbi.nlm.nih.gov/entrez/viewer.fcgi?db=nucleotide&val=116734707 (Downloaded on Jan. 29, 2007).

Gilbert, R., et al., "Prolonged dystrophin expression and functional correction of mdx mouse muscle following gene transfer with a helper-dependent (gutted) adenovirus-encoding murine dystrophin," Human Molecular Genetics, 12(11)1287-1299 (2003).

Gonzalez-Cadavid, N.F., et al., "Organization of the human myostatin gene and expression in healthy men and HIV-infected men with muscle wasting," PNAS, 95:14938-14943 (1998).

Gray, et al., "Identification of a binding site on the type II activin receptor for activin and inhibin", Journal of Biological Chemistry, 275(5):3206-3212(2000).

Greenspan, N.S., et al., "Defining epitopes: It's not as easy as it seems," Nature Biotechnology, 17:936-937 (1999).

Greenwald, et al., "The BMP7/ActRII Extracellular Domain Complex Provides New Insights into the Cooperative Nature of Receptor Assembly," Molecular Cell, 11:605-617 (2003).

Greenwald, J., et al., "Three-finger toxin fold for the extracellular ligand-binding domain of the type II activin receptor serine kinase," Nature Structural Biology, 6(1):18-22 (1999).

Gregoriadis, G., et al., "Polysialic acids: potential in drug delivery," FEBS, 315(3):271-276 (1993).

Gupta, V. et al., "Transforming Growth Factor-b Superfamily: Evaluation as Breast Cancer Biomarkers and Preventive Agents," Current Cancer Drug Targets, 4:165-182 (2004).

Gura, T., "Cancer Models: Systems for Identifying New Drugs Are Often Faulty," Science, 278(5340):1041-1042 (1997).

Hamrick et al., "Bone Mineral Content and Density in the Humerus of Adult Myostatin-Deficient Mice," Calcified Tissue International, 71:63-68 (2002).

Hamrick, "Increased Bone Mineral Density in the Femora of GDF8 Knockout Mice," The Anatomical Record, Part A 272A:388-391 (2003).

Hamrick, M.W., et al., "Femoral Morphology and Cross-sectional Geometry of Adult Myostatin-deficient Mice," Bone, 27(3):343-349 (2000).

Harrison, C.A., et al., "An Activin Mutant with Disrupted ALK4 Binding Blocks Signaling via Type II Receptors," The Journal of Biological Chemistry, 279(27):28036-28044 (2004).

Harrison, et al., "Antagonists of activin signaling: mechanisms and potential biological applications," Trends in Endocrinology and Metabolism, 16(2):73-78 (2005).

Hashimoto et al., "Functional Regulation of Osteoblastic Cells by the Interaction of Activin-A with Follistatin," The Journal of Biological Chemistry, 267(7):4999-5004 (1992).

Hemmati-Brivanlou, A., et al., "A truncated activin receptor inhibits mesoderm induction and formation of axial structures in *Xenopus* embryos," Nature, 359:609-614 (1992).

Herbert, W.J., et al., The Dictionary of Immunology, Academic Press, 3rd Edition, London, pp. 58-59 (1985).

Hilden, K., et al., "Expression of Type II Activin Receptor Genes During Differentiation of Human K562 Cells and cDNA Cloning of the Human Type IIB Activin Receptor," Blood, 83(8):2163-2170 (1994).

Hill, J.J., et al., "Regulation of Myostatin in Vivo by Growth and Differentiation Factor-Associated Serum Protein-1: A Novel Protein with Protease Inhibitor and Follistatin Domains," Molecular Endocrinology, 17(6):1144-1154 (2003).

Hsieh, Matthew M, et al., "HIF-prolyl hydroxylase inhibition results in endogenous erythropoietin induction, erythrocytosis, and modest fetal hemoglobin expression in rhesus macaques," Blood, 110(6):2140-2147 (2007).

lkenoue et al., "Inhibitory Effects of Activin-A on Osteoblast Differentiation During Cultures of Fetal Rat Calvarial Cells," Journal of Cellular Biochemistry, 75:206-214 (1999).

Kaiser, J., "First Pass at Cancer Genome Reveals Complex Landscape," Science, 313:1370 (2006).

Kaspar, B.K., et al., "Retrograde Viral Delivery of IGF-1 Prolongs Survival in a Mouse ALS Model," Science, 301:839-842 (2003).

Kim, et al., "Type IIA IgG-Fc Fusion Protein, Increases Hemoglobin and Hematocrit Levels in Postmenopausal Healthy Women," Blood, 112(11):1316 (2008).

Knight, "Roles of Inhibins, Activins, and Follistatin in the Female Reproductive System," Frontiers in Neuroendocrinology, 17:476-509 (1996).

Kosaki, R., et al., "Left-Right Axis Malformations Associated With Mutations in ACVR2B, the Gene for Human Activin Receptor Type IIB," American Journal of Medical Genetics, 82:70-76 (1999).

Koseki, et al., "Role of TCF-b Family in Osteoclastogenesis Induced by RANKL," Cellular Signaling, 14:31-36 (2002).

Krag, T.O.B., et al., "Heregulin ameliorates the dystrophic phenotype in mdx mice," PNAS, 101(38):13856-13860 (2004).

Krneta, J., et al., "Dissociation of Angiogenesis and Tumorigenesis in Follistatin- and Activin-Expressing Tumors," Cancer Research, 66(11):5686-5695 (2006).

Krystal et al., "Transforming Growth Factor β1 Is an Inducer of Erythroid Differentiation." J. Exp. Med. 180:851-860 (1994).

Kubanek, B., "Introduction: The Role of the Microenvironment and Cytokines on the Modulation of Erythropoiesis," Annals New York Academy of Sciences, pp. 257-258 (1994).

Kunihro, T., et al., "Regulation of Muscle Mass and Hepatic Steatosis by Follistatin-derived Myostatin Inhibitors," Making Muscle in the Embryo and Adult: a joint meeting of Frontiers in Myogenesis and Skeletal Muscle Stem and Satellite Cells, New York, NY, p. 45 (Abstract) (1990).

Lazar, E., et al., "Transforming Growth Factor α: Mutation of Aspartic Acid 47 and Leucine 48 Results in Different Biological Activities," Molecular and Cellular Biology, 8(3):1247-1252 (1988).

Lebrun, J.J., et al, "Activin and Inhibin Have Antagonistic Effects on Ligand-Dependent Heteromerization of the Type I and Type II Activin Receptors and Human Erythroid Differentiation," Molecular and Cellular Biology, 17(3):1682-1691 (1997).

Lee et al., "Regulation of Muscle Growth by Multiple Ligands Signaling Through Activin Type II Receptors," PNAS 102(50):18117-18122 (2005).

Lee, et al., "Regulation of Myostatin Activity and Muscle Growth," PNAS, 98(16):9306-9311 (2001).

Leto et al., "Activin A Circulating Levels in Patients with Bone Metastasis from Breast or Prostate Cancer," Clin Exp Metastasis, 23(2):117-122 (2006).

Li, Q., et al., "Prevention of cachexia-like syndrome development and reduction of tumor progression in inhibin-deficient mice following administration of a chimeric activin receptor type II-murine Fc protein," Molecular Human Reproduction, 13(9):675-683 (2007).

Ludlow, H., et al., "Development of a new antibody to the human inhibin/activin βB subunit and its application to improved inhibin B ELISAs," J. Immunol. Methods, 329:102-111 (2008).

Maguer-Satta, V., et al, "Regulation of human erythropoiesis by activin A, BMP2, and BMP4, members of the TGFβ family," Experimental Cell Research, 282:110-120 (2003).

Matzuk et al., "Different phenotypes for mice deficient in either activins or activin receptor type II," Nature, 374:356-360 (1995).

McNally, E.M., "Powerful Genes—Myostatin Regulation of Human Muscle Mass," N. Engl. J. Med., 350(26):2642-2644 (2004).

McPherron, A.C., et al., "Regulation of Skeletal Muscle Mass in Mice by a Bew TGF-b Superfamily Member," Nature, 387:83-90 (1997).

McPherson, S.J., et al., "Growth inhibitory response to activin A and B by human prostate tumour cell lines LNCaP and DU1465", Journal of Endocrinology, 154:535-545 (1997).

Menstruation: Absent Periods (Amenorrhea), Website downloaded on Jun. 14, 2010, <http://adam.about.com/reports/000101_2.htm?p=1> (11 pages).

Merck Manuals Online Medical Library (online). Anemia of Chronic Disease, Jun. 10, 2008. Downloaded from the internet on Jan. 5, 2010. <http://web.archive.org/web/20080610070226/http://www.merck.com/mmpe/sec11/ch130/ch130d.html> pp. 1-2.

Merck Manuals Online Medical Library (online). Iron Deficiency Anemia, Jun. 10, 2008. Downloaded from the internet on Jan. 5, 2010. <http://web.archive.org/web/20080610070221/http://www.merck.com/mmpe/sec11/ch130/ch130d.html> pp. 1-4.

Meriggiola et al., "Follistatin Decreases Activin-Stimulated FSH Secretion with No Effect on GnRH-Stimulated FSH Secretion in Prepubertal Male Monkeys," Endocrinology, 134(4):1967-1970 (1994).

Mickle, et al., "Genotype-Phenotype Relationships in Cystic Fibrosis," Med. Clin. North Am., 84(3):597-607 (2000).

Miura, P., et al., "Utrophin upregulation for treating Duchenne or Becker muscular dystrophy: how close are we?," Trends in Molecular Medicine, 12(3):122-129 (2006).

Murase et al., "Possible Involvement of Protein Kinases and Smad2 Signaling Pathways on Osteoclast Differentiation Enhanced by Activin A," Journal of Cellular Physiology, 188:236-242 (2001).

Nagamine et al., "Immunohistochemical Detection of Activin A, Follistatin, and Activin Receptors during Fracture Healing in the Rat," Journal of Orthopaedic Research, 16:314-321 (1998).

Nakamura, K., et al, "Effect of Erythroid Differentiation Factor on Maintenance of Human Hematopoietic Cells in Co-cultures with Allogenic Stromal Cells," Biochemical and Biophysical Research Communications, 194(3):1103-1110 (1993).

Ngo, J.T., et al., "Computational Complexity, Protein Structure Prediction, and the Levinthal Paradox," The Protein Folding Problem and Tertiary Structure Prediction, Merz et al., eds., Birkhauser, Boston, 492-495 (1994).

Ogawa et al., "Bovine Bone Activin Enhances Bone Morphogenetic Protein-Induced Ectopic Bone Formation," The Journal of Biological Chemistry, 267(20):14233-14237 (1992).

Oh, S.P., et al., "Activin type IIA and IIB receptors mediate Gdf11 signaling in axial vertebral patterning," Genes & Development, 16:2749-2754 (2002).

Oue et al., "Effect of Local Injection of Activin A on Bone Formation in Newborn Rats," Bone, 15(3):361-366 (1994).

Patel, K., et al., "The function of Myostatin and strategies of Myostatin blockade—new hope for therapies aimed at promoting growth of skeletal muscle," Neuromuscular Disorders, 15:117-126 (2005).

Pearsall, et al., "A Soluble Activin Receptor Type IIA (ACTRIIA) Acts As a Novel Bone Anabolic Agent," The Official Journal of the European Calcified Tissue Society, 34th Europena Symposium on Calcified Tissues (2007).

Pearsall, et al., "Treatment with a Soluble Activin Type II Receptor Reverses Bone Loss in Ovariectomized Mice," Journal of Bone and Mineral Research 2006 Abstracts, 21(1):s1-s530 (2006).

Pearsall, R.S., et al., "A soluble activin Type IIA receptor induces bone formation and improves skeletal integrity", PNAS, 105(9):7082-7087 (2008).

Qi, et al., "Blockade of type β transforming growth factor signaling prevents liver fibrosis and dysfunction in the rat," PNAS, 96:2345-2349 (1999).

Raju, T.S., "Glycosylation in the Fc domain of IgG increases resistance to proteolytic cleavage by papain," Biochemical and Biophysical Research Communications, 341:797-803 (2006).

Rebbapragada, et al., "Myostatin Signals Through a Transforming Growth Fact b-Like Signaling Pathway to Block Adipogenesis," Molecular and Cellular Biology, 23(20):7230-7242 (2003).

Reis, F.M., et al., "Activin, Inhibin and the Human Breast," Molecular and Cellular Edocrinology, 225:77-82 (2004).

Risbridger, G.P, et al., "Activins and Inhibins in Endocrine and Other Tumors," Endocrine Reviews, 22(6):836-858 (2001).

Robinson, G.W., et al., "Inhibins and Activins Regulate Mammary Epithelial Cell Differentiation Through Mesenchymal-epithelial Interactions," Development, 124:2701-2708 (1997).

Rodriquez, J.E.S., et al., "Enhanced Osteoclastogenesis Causes Osteopenia in Twisted Gastrulation-Deficient Mice Through Increased BMP Signaling," J. Bone Miner. Res., 24:1917-1926 (2009).

Rosenzweig et al., "Cloning and characterization of a human type II receptor for bone morphogenetic proteins," PNAS, 92:7632-7636 (1995).

Ruzek et al. "Minimal Effects on Immune Parameters Following Chronic Anti-TGF-β Monoclonal Antibody Administration to Normal Mice." Immunopharmacology and Immunotoxicology, 25(2):235-257 (2003).

Sakai et al., "Activin Enhances Osteoclast-Like Cell Formation in Vitro," Biochemical and Biophysical Research Communications, 195(1):39-46 (1993).

Sakai et al., "Activin Increases Bone Mass and Mechanical Strength of Lumbar Vertebrae in Aged Ovariectomized Rats," Bone, 27(1):91-96 (2000).

Sakai et al., "Activin release from bone coupled to bone resorption in organ culture of neonatal mouse calvaria," Bone, 26(3):235-240 (2000).

Sakai et al., "Involvement of Activin in the Regulation of Bone Metabolism," Molecular and Cellular Endocrinology, 180:183-188 (2001).

Sakai et al., "Local Administration of Activin Promotes Fracture Healing in the Rat Fibula Fracture Model," Bone, 25(2):191-196 (1999).

Sakai et al., "The Measurement of Activin/EDF in Mouse Serum: Evidence for Extragonadal Production." Biochecmical and Biophysical Research Communications, 188(2):921-926 (1992).

Sakai, et al., "Osteogenic Activity of Activin in Young Normal Rats and Young Adult and Aged Rats after Ovariectomy," Bone, 23:S467 (1998).

Satoh et al., "Hemodynamic changes by recombinant erythropoietin therapy in hemodialyzed patients." Hypertension, 15(3):262-266 (1990).

Schuelke, M., et al., "Myostatin Mutation Associated with Gross Muscle Hypertrophy in a Child," New England Journal of Medicine, 350(26):2682-2688 (2004).

Shao, L., et al., "Effect of Activin A on Globin Gene Expression in Purified Human Erythroid Progenitors," Blood, 79(3):773-781 (1992).

Shav-Tal, Y., et al., "The Role of Activin A in Regulation of Hemopoiesis," Stem Cells, 20:493-500 (2002).

Shiozaki, M., et al, "Activin A: A Commitment Factor in Erythroid Differentiation," Biochemical and Biophysical Research Communications, 242:631-635 (1998).

Shiozaki, M., et al, "Evidence for the participation of endogenous activin A/erythroid differentiation factor in the regulation of erythropoiesis," Proc. Natl. Acad. Sci. USA, 89:1553-1556 (1992).

Shiozaki, M., et al.,"In Vivo Treatment With Erythroid Differentiation Factor (EDF / Activin A) Increases Erythroid Precursors (CFU-E and BFU-E) in Mice," Biochemical and Biophysical Research Communications, 165(3):1155-1161 (1989).

Shuto et al., "Osteoblasts Express Types I and II Activin Receptors During Early Intramembranous and Endochondral Bone Formation," Journal of Bone Mineral Research, 12(3):403-411 (1997).

Song, J., et al., "The Type II Activin Receptors Are Essential for Egg Cylinder Growth, Gastrulation, and Rostral Head Development in Mice," Development Biology, 213:157-169 (1999).

Springer, et al., "Seventh European Congress on Clinical and Economic Aspects of Osteoporosis and Osteoarthritis," Osteoporosis International, 18(1):S29-S75 (2007).

Sun, et al., "FSH Directly Regulates Bone Mass," Cell, 125:247-260 (2006).

Thompson, et al., "Structures of an ActRIIB: activin A complex reveal a novel binding mode for TGF-beta ligand: receptor interactions", EMBO 22(7):1555-1566 (2003).

Tinsley, J., et al., "Expression of full-length utrophin prevents muscular dystrophy in *mdx* mice," Nature Medicine, 4(12):1441-1444 (1998).

Tsuchida, et al., "Activin isoforms signal through type I receptor serine/threonine kinase ALK7," Molecular and Cellular Endocrinology, 220:59-65 (2004).

Tu, P., et al., "Genetic Disruption of Myostatin Reduces the Development of Proatherogenic Dyslipidemia and Atherogenic Lesions in Ldlr Null Mice," Diabetes, 58:1739-1748 (2009).

Ukkola, et al., "Adiponectin: A Link Between Excess Adiposity and Associated Comorbidities?", Journal of Molecular Medicine, 80(11):696-702 (2002).

Vallet, S., et al., "Activin A promotes multiple myeloma-induced osteolysis and is a promising target for myeloma bone disease," PNAS, 107(11):5124-5129 (2010).

Wagner, K.R., et al., "A Phase I/II trial of MYO-029 in Adult Subjects with Muscular Dystrophy," Ann. Neurol., 63:561-571 (2008).

Wagner, K.R., et al., "Loss of Myostatin Attenuates Severity of Muscular Dystrophy in *mdx* Mice," Ann. Neurol., 52:832-836 (2002).

Wagner, K.R., et al., "Muscle regeneration in the prolonged absence of myostatin," PNAS, 102(7):2519-2524 (2005).

Walsh, F. S, et al., "Myostatin: a modulator of skeletal-muscle stems cells," Biochemical Society Transactions, 33(Pt.6):1513-1517 (2005).

Weber, et al., "A slient H-bond can by mutationally activated for high-affinity interaction of BMP-2 and activin type IIB receptor," BMC Structural Biology, 7(6):1-20 (2007).

Wells, J.A., "Additivity of Mutational Effects in Proteins," Biochemistry, 29(37):8509-8517 (1990).

Welt, et al., "Activin: an endocrine or panacrine agent?," European Journal of Endocrinology 139:469-471 (1998).

Wiater, et al., "Inhibin is an Antagonist of Bone Morphogenetic Protein Signaling," The Journal of Biological Chemistry, 278(10):7934-7941 (2003).

Wolfman, N.M., et al., "Activation of latent myostatin by the BMP-1/tolloid family of metalloproteinases," PNAS, 100(26):15842-15846 (2003).

Yokota, T., et al., "Isolation and characterization of a mouse cDNA clone that expresses mast-cell growth-factor activity in monkey cells," Proc. Natl. Acad. Sci. USA, 81:1070-1074 (1984).

Yu et al., "Specific roles of activin/inhibin in human erythropoiesis in vitro," Annals New York Academy of Sciences, 20(10):1243-1246 (1991).

Yu, J., et al., "Importance of FSH-releasing protein and inhibin in erythrodifferentiation," Nature, 330:765-767 (1987).

Zhao, B., et al., "Transgenic expression of myostatin propeptide prevents diet-induced obesity and insulin resistance," Biochemical and Biophysical Research Communications, 337:248-255 (2005).

Benny Klimek, Margaret E., et al., "Acute inhibition of myostatin-family proteins preserves skeletal muscle in mouse models of cancer cachexia," Biochemical and Biophysical Research Communications, 391:1548-1554 (2010).

Binkert, et al., "Cloning, sequence analysis and expression of a cDNA encoding a novel insulin-like growth factor binding protein (IGFBP-2)," The EMBO Journal, 8(9):2497-2502 (1989).

Caricasole, A. A. D., et al., "Human Growth-Differentiation Factor 3 (HGDF3): Developmental Regulation in Human Teratocarcinoma Cell Lines and Expression in Primary Testicular Germ Cell Tumours," Oncogene, 16:95-103 (1998).

DePaolo, L.V., et al., "Passive Immunoneutralization with a Monoclonal Antibody Reveals a Role for Endogenous Activin-B in Mediating FSH Hypersecretion during Estrus and Following Ovariectomy of Hypophysectomized, Pituitary-Grafted Rats," Endocrinology, 130(3):1741-1743 (1992).

Gilchrist, A., et al., "Antagonists of the Receptor-G Protein Interface Block Gi-coupled Signal Transduction," Journal of Biological Chemistry, The American Society of Biological Chemists, Inc., 273(24):14912-14919 (1998).

Greenwald, et al., "Characterization of the Extracellular Ligand-Binding Domain of the Type II Activin Receptor," Biochemistry, 37(47):16711-16718 (1998).

Mathews, L.S., et al., "Expression Cloning of an Activin Receptor, a Predicted Transmembrane Serine Kinase," Cell, 65(6):973-982 (1991).

Matzuk et al., "Cloning of the human activin receptor cDNA reveals high evolutionary conservation," Biochim Biophys Acta, 1130(1):105-108 (1992).

McPherron, A.C., et al., "GDF-3 and GDF-9: Two New Members of the Transforming Growth Factor-B Superfamily Containing a Novel Pattern of Cysteines," Journal of Endocrinology, 268(5):3444-3449 (1993).

Murata, T., et al., "Anti-activin A Antibody (IgY) Specifically Neutralizes Various Activin A Activities," Proceedings of the Society for Experimental Biology & Medicine, 211(1):100-107 (1996).

Ruckle et al., "Single-Dose, Randomized, Double-Blind, Pacebo-Controlled Study of ACE-011 (ACTRIIA-IgG1) in Postmenopausal Women," Journal of Bone and Mineral Research, vol. 24(4), pp. 744-752 (2009).

Schmelzer, C.H., et al., "Purification and Characterization of Recombinant Human Activin B," Biochimica et Biophysica Acta, 1039(2):135-141 (1990).

Thompson, T.B., et al., "Beta A versus beta B: is it merely a matter of express?," Molecular and Cellular Endocrinology, 225:9-17 (2004).

Tisdale, M.J., "Cachexia in Cancer Patients," Nat. Rev. Cancer, 2:862-871 (2002).

Wang, W., et al., "GDF-3 is an adipogenic cytokine under high fat dietary condition," Biochemical and Biophysical Research Comm., 321(4):1024-1031 (2004).

\* cited by examiner

```
  1  MDAMKRGLCC VLLLCGAVFV SPGAA TREC IYYNANWELE RTNQSGLERC
 51  EGEQDKRLHC YASWRNSSGT IELVKKGCWL DDFNCYDRQE CVATEENPQV
101  YFCCCEGNFC NERFTHLPEA GGPEVTYEPP PTGGGTHTCP PCPAPELLGG
151  PSVFLFPPKP KDTLMISRTP EVTCVVVDVS HEDPEVKFNW YVDGVEVHNA
201  KTKPREEQYN STYRVVSVLT VLHQDWLNGK EYKCKVSNKA LPAPIEKTIS
251  KAKGQPREPQ VYTLPPSREE MTKNQVSLTC LVKGFYPSDI AVEWESNGQP
301  ENNYKTTPPV LDSDGSFFLY SKLTVDKSRW QQGNVFSCSV MHEALHNHYT
351  QKSLSLSPGK (SEQ ID NO: 3)
```

FIGURE 1

```
  1  ATGGATGCAA TGAAGAGAGG GCTCTGCTGT GTGCTGCTGC TGTGTGGAGC
     TACCTACGTT ACTTCTCTCC CGAGACGACA CACGACGACG ACACACCTCG

A  E  T     R  E  C     I  Y  Y
 51  AGTCTTCGTT TCGCCCGGCG CCGCTGAGAC ACGGGAGTGC ATCTACTACA
     TCAGAAGCAA AGCGGGCCGC GGCGACTCTG TGCCCTCACG TAGATGATGT

N  A  N  W     E  L  E     R  T  N     Q  S  G     L  E  R  C
101  ACGCCAACTG GGAGCTGGAG CGCACCAACC AGAGCGGCCT GGAGCGCTGC
     TGCGGTTGAC CCTCGACCTC GCGTGGTTGG TCTCGCCGGA CCTCGCGACG

E  G  E     Q  D  K  R     L  H  C     Y  A  S     W  R  N  S
151  GAAGGCGAGC AGGACAAGCG GCTGCACTGC TACGCCTCCT GGCGCAACAG
     CTTCCGCTCG TCCTGTTCGC CGACGTGACG ATGCGGAGGA CCGCGTTGTC

S  G  T     I  E  L     V  K  K  G     C  W  L     D  D  F
201  CTCTGGCACC ATCGAGCTCG TGAAGAAGGG CTGCTGGCTA GATGACTTCA
     GAGACCGTGG TAGCTCGAGC ACTTCTTCCC GACGACCGAT CTACTGAAGT

N  C  Y  D     R  Q  E     C  V  A     T  E  E  N     P  Q  V
251  ACTGCTACGA TAGGCAGGAG TGTGTGGCCA CTGAGGAGAA CCCCCAGGTG
     TGACGATGCT ATCCGTCCTC ACACACCGGT GACTCCTCTT GGGGGTCCAC

Y  F  C     C  C  E  G     N  F  C     N  E  R     F  T  H  L
301  TACTTCTGCT GCTGTGAAGG CAACTTCTGC AACGAGCGCT TCACTCATTT
     ATGAAGACGA CGACACTTCC GTTGAAGACG TTGCTCGCGA AGTGAGTAAA

P  E  A     G  G  P     E  V  T  Y     E  P  P     P  T
351  GCCAGAGGCT GGGGGCCCGG AAGTCACGTA CGAGCCACCC CCGACAGGTG
     CGGTCTCCGA CCCCCGGGCC TTCAGTGCAT GCTCGGTGGG GGCTGTCCAC

401  GTGGAACTCA CACATGCCCA CCGTGCCCAG CACCTGAACT CCTGGGGGGA
     CACCTTGAGT GTGTACGGGT GGCACGGGTC GTGGACTTGA GGACCCCCCT

451  CCGTCAGTCT TCCTCTTCCC CCCAAAACCC AAGGACACCC TCATGATCTC
     GGCAGTCAGA AGGAGAAGGG GGGTTTTGGG TTCCTGTGGG AGTACTAGAG

501  CCGGACCCCT GAGGTCACAT GCGTGGTGGT GGACGTGAGC CACGAAGACC
     GGCCTGGGGA CTCCAGTGTA CGCACCACCA CCTGCACTCG GTGCTTCTGG

551  CTGAGGTCAA GTTCAACTGG TACGTGGACG GCGTGGAGGT GCATAATGCC
     GACTCCAGTT CAAGTTGACC ATGCACCTGC CGCACCTCCA CGTATTACGG

601  AAGACAAAGC CGCGGGAGGA GCAGTACAAC AGCACGTACC GTGTGGTCAG
     TTCTGTTTCG GCGCCCTCCT CGTCATGTTG TCGTGCATGG CACACCAGTC

651  CGTCCTCACC GTCCTGCACC AGGACTGGCT GAATGGCAAG GAGTACAAGT
     GCAGGAGTGG CAGGACGTGG TCCTGACCGA CTTACCGTTC CTCATGTTCA

701  GCAAGGTCTC CAACAAAGCC CTCCCAGCCC CCATCGAGAA AACCATCTCC
     CGTTCCAGAG GTTGTTTCGG GAGGGTCGGG GGTAGCTCTT TTGGTAGAGG

751  AAAGCCAAAG GGCAGCCCCG AGAACCACAG GTGTACACCC TGCCCCCATC
     TTTCGGTTTC CCGTCGGGGC TCTTGGTGTC CACATGTGGG ACGGGGGTAG
```

FIGURE 2

```
 801   CCGGGAGGAG ATGACCAAGA ACCAGGTCAG CCTGACCTGC CTGGTCAAAG
       GGCCCTCCTC TACTGGTTCT TGGTCCAGTC GGACTGGACG GACCAGTTTC

851   GCTTCTATCC CAGCGACATC GCCGTGGAGT GGGAGAGCAA TGGGCAGCCG
       CGAAGATAGG GTCGCTGTAG CGGCACCTCA CCCTCTCGTT ACCCGTCGGC

901   GAGAACAACT ACAAGACCAC GCCTCCCGTG CTGGACTCCG ACGGCTCCTT
       CTCTTGTTGA TGTTCTGGTG CGGAGGGCAC GACCTGAGGC TGCCGAGGAA

951   CTTCCTCTAT AGCAAGCTCA CCGTGGACAA GAGCAGGTGG CAGCAGGGGA
       GAAGGAGATA TCGTTCGAGT GGCACCTGTT CTCGTCCACC GTCGTCCCCT

1001   ACGTCTTCTC ATGCTCCGTG ATGCATGAGG CTCTGCACAA CCACTACACG
       TGCAGAAGAG TACGAGGCAC TACGTACTCC GAGACGTGTT GGTGATGTGC

1051   CAGAAGAGCC TCTCCCTGTC CCGGGTAAA TGA (SEQ ID NO: 4)
       GTCTTCTCGG AGAGGGACAG GGCCCATTT ACT (SEQ ID NO: 5)
```

FIGURE 2 CONT

```
  1   ATGGATGCAA TGAAGAGAGG GCTCTGCTGT GTGCTGCTGC TGTGTGGAGC
      TACCTACGTT ACTTCTCTCC CGAGACGACA CACGACGACG ACACACCTCG

A   E   T   R   E   C   I   Y   Y
 51   AGTCTTCGTT TCGCCCGGCG CCGCCGAAAC CCGCGAATGT ATTTATTACA
      TCAGAAGCAA AGCGGGCCGC GGCGGCTTTG GGCGCTTACA TAAATAATGT

N   A   N   W   E   L   E   R   T   N   Q   S   G   L   E   R   C
101   ATGCTAATTG GGAACTCGAA CGGACGAACC AATCCGGGCT CGAACGGTGT
      TACGATTAAC CCTTGAGCTT GCCTGCTTGG TTAGGCCCGA GCTTGCCACA

E   G   E   Q   D   K   R   L   H   C   Y   A   S   W   R   N   S
151   GAGGGGGAAC AGGATAAACG GCTCCATTGC TATGCGTCGT GGAGGAACTC
      CTCCCCCTTG TCCTATTTGC GGAGGTAACG ATACGCAGCA CCTCCTTGAG

S   G   T   I   E   L   V   K   K   G   C   W   L   D   D   F
201   CTCCGGGACG ATTGAACTGG TCAAGAAAGG GTGCTGGCTG GACGATTTCA
      GAGGCCCTGC TAACTTGACC AGTTCTTTCC CACGACCGAC CTGCTAAAGT

N   C   Y   D   R   Q   E   C   V   A   T   E   E   N   P   Q   V
251   ATTGTTATGA CCGCCAGGAA TGTGTCGCGA CCGAAGAGAA TCCGCAGGTC
      TAACAATACT GGCGGTCCTT ACACAGCGCT GGCTTCTCTT AGGCGTCCAG

Y   F   C   C   E   G   N   F   C   N   E   R   F   T   H   L
301   TATTTCTGTT GTTGCGAGGG GAATTTCTGT AATGAACGGT TTACCCACCT
      ATAAAGACAA CAACGCTCCC CTTAAAGACA TTACTTGCCA AATGGGTGGA

P   E   A   G   G   P   E   V   T   Y   E   P   P   P   T
351   CCCCGAAGCC GGCGGGCCCG AGGTGACCTA TGAACCCCCG CCCACCGGTG
      GGGGCTTCGG CCGCCCGGGC TCCACTGGAT ACTTGGGGGC GGGTGGCCAC

401   GTGGAACTCA CACATGCCCA CCGTGCCCAG CACCTGAACT CCTGGGGGGA
      CACCTTGAGT GTGTACGGGT GGCACGGGTC GTGGACTTGA GGACCCCCCT

451   CCGTCAGTCT TCCTCTTCCC CCCAAAACCC AAGGACACCC TCATGATCTC
      GGCAGTCAGA AGGAGAAGGG GGGTTTTGGG TTCCTGTGGG AGTACTAGAG

501   CCGGACCCCT GAGGTCACAT GCGTGGTGGT GGACGTGAGC CACGAAGACC
      GGCCTGGGGA CTCCAGTGTA CGCACCACCA CCTGCACTCG GTGCTTCTGG

551   CTGAGGTCAA GTTCAACTGG TACGTGGACG GCGTGGAGGT GCATAATGCC
      GACTCCAGTT CAAGTTGACC ATGCACCTGC CGCACCTCCA CGTATTACGG

601   AAGACAAAGC CGCGGGAGGA GCAGTACAAC AGCACGTACC GTGTGGTCAG
      TTCTGTTTCG GCGCCCTCCT CGTCATGTTG TCGTGCATGG CACACCAGTC

651   CGTCCTCACC GTCCTGCACC AGGACTGGCT GAATGGCAAG GAGTACAAGT
      GCAGGAGTGG CAGGACGTGG TCCTGACCGA CTTACCGTTC CTCATGTTCA

701   GCAAGGTCTC CAACAAAGCC CTCCCAGCCC CCATCGAGAA AACCATCTCC
      CGTTCCAGAG GTTGTTTCGG GAGGGTCGGG GGTAGCTCTT TTGGTAGAGG

751   AAAGCCAAAG GGCAGCCCCG AGAACCACAG GTGTACACCC TGCCCCCATC
      TTTCGGTTTC CCGTCGGGGC TCTTGGTGTC CACATGTGGG ACGGGGGTAG
```

FIGURE 3

```
 801    CCGGGAGGAG ATGACCAAGA ACCAGGTCAG CCTGACCTGC CTGGTCAAAG
        GGCCCTCCTC TACTGGTTCT TGGTCCAGTC GGACTGGACG GACCAGTTTC

851    GCTTCTATCC CAGCGACATC GCCGTGGAGT GGGAGAGCAA TGGGCAGCCG
        CGAAGATAGG GTCGCTGTAG CGGCACCTCA CCCTCTCGTT ACCCGTCGGC

901    GAGAACAACT ACAAGACCAC GCCTCCCGTG CTGGACTCCG ACGGCTCCTT
        CTCTTGTTGA TGTTCTGGTG CGGAGGGCAC GACCTGAGGC TGCCGAGGAA

951    CTTCCTCTAT AGCAAGCTCA CCGTGGACAA GAGCAGGTGG CAGCAGGGGA
        GAAGGAGATA TCGTTCGAGT GGCACCTGTT CTCGTCCACC GTCGTCCCCT

1001    ACGTCTTCTC ATGCTCCGTG ATGCATGAGG CTCTGCACAA CCACTACACG
        TGCAGAAGAG TACGAGGCAC TACGTACTCC GAGACGTGTT GGTGATGTGC

1051    CAGAAGAGCC TCTCCCTGTC CCGGGTAAA TGA  (SEQ ID NO: 6)
        GTCTTCTCGG AGAGGGACAG GGGCCCATTT ACT  (SEQ ID NO: 7)
```

ISOLATED NUCLEIC ACID ENCODING A TRUNCATED ACTRIIB FUSION PROTEIN

CROSS-REFERENCE TO RELATED APPLICATIONS

This application claims the benefit of U.S. Provisional Application Ser. Nos. 61/268,420, filed on Jun. 12, 2009, 61/280,543, filed on Nov. 3, 2009. These applications are hereby incorporated by reference in their entireties.

SEQUENCE LISTING

The instant application contains a Sequence Listing which has been submitted via EFS-Web and is hereby incorporated by reference in its entirety. Said ASCII copy, created on Aug. 11, 2010, is named PHPH0451.txt and is 27,489 bytes in size.

BACKGROUND OF THE INVENTION

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The family is represented by proteins named, variously, the activins and inhibins, TGF-beta, Growth and Differentiation Factors (GDFs) and Bone Morphogenetic Factors (BMPs). Other members of the family are also known, such as Nodal and Lefty. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al., Nat Genet. 1997, 17(1):71-4. Furthermore, in humans, inactive alleles of GDF8 are associated with increased muscle mass and, reportedly, exceptional strength. Schuelke et al., N Engl J Med 2004, 350:2682-8.

Changes in muscle, bone, fat, cartilage and other tissues may be achieved by agonizing or antagonizing signaling that is mediated by an appropriate TGF-beta family member. Thus, there is a need for agents that function as potent regulators of signaling by members of the TGF-beta superfamily.

SUMMARY OF THE INVENTION

In certain aspects, the present disclosure provides novel ActRIIB polypeptides, particularly amino- and carboxy-terminal truncations and sequence alterations. In one embodiment, polypeptides including amino acids 25-131 of human ActRIIB (SEQ ID NO:1) or variants thereof, are described. Such polypeptides are demonstrated to have surprising efficacy in the treatment of a variety of disorders, but particularly disorders associated with obesity, insulin resistance and other metabolic disorders. ActRIIB polypeptides disclosed herein can be used to have a variety of desirable effects in patients, including, for example, increasing lean body mass, decreasing white fat mass, increasing brown fat mass, decreasing serum triglycerides, decreasing serum insulin levels or decreasing serum free fatty acid levels. ActRIIB polypeptides disclosed herein may be used for the treatment of a variety of disorders or conditions, including muscle and neuromuscular disorders (e.g., muscular dystrophy, amyotrophic lateral sclerosis (ALS), and muscle atrophy), adipose tissue disorders (e.g., obesity, fatty liver disease), metabolic disorders (e.g., type 2 diabetes, insulin resistance, metabolic syndrome), neurodegenerative disorders, and muscle wasting associated with old age (sarcopenia), prostate cancer therapy (e.g., androgen deprivation therapy), and cachexia associated with a variety of cancers. Examples of ActRIIB polypeptides include a human ActRIIB-Fc fusion protein set forth in SEQ ID NO:8 and described herein as ActRIIB(25-131)-hFc.

In certain aspects, the disclosure provides novel polypeptides that are derived from ActRIIB (referred to as ActRIIB polypeptides). In some embodiments, a polypeptide may be selected from the group consisting of: a polypeptide comprising an amino acid sequence wherein the amino acid sequence consists of the sequence of SEQ ID NO:8 or an amino acid sequence that differs from SEQ ID NO:8 at no more than one, two, three, four or five amino acid positions; a polypeptide produced by the expression in a mammalian cell of the nucleic acid of SEQ ID NO: 4 or a nucleic acid that hybridizes under stringent condition to the complement thereof; a polypeptide produced by the expression in a mammalian cell of the nucleic acid of SEQ ID NO:6 or a nucleic acid that hybridizes under stringent conditions to the complement thereof. A polypeptide disclosed herein may comprise a portion derived from ActRIIB and one or more heterologous portions, wherein the portion derived from ActRIIB may comprise an amino acid sequence consisting of the sequence of amino acids 25-131 of SEQ ID NO:1 or an amino acid sequence that differs the sequence of amino acids 25-131 of SEQ ID NO:1 at no more than one, two, three, four or five amino acid positions. The heterologous portion may comprise a constant domain of an immunoglobulin, an Fc domain of an immunoglobulin or, particularly, an Fc domain of a human IgG1 (the term "human IgG1 shall be understood to include variants of such Fc that are compatible with use in humans). ActRIIB polypeptides may include a portion derived from ActRIIB that comprises an amino acid sequence consisting of the sequence of amino acids 25-131 of SEQ ID NO:1. An ActRIIB polypeptide disclosed herein may be such that the amino terminus has the sequence ETR. An ActRIIB polypeptide disclosed herein may cause a statistically significant increase in lean body mass in a mouse after four weeks of treatment twice per week at a dose level of 10 mg/kg. The mean increase of lean tissue mass may be at least 1, 2, 3, 4 or 5 or more grams. An ActRIIB polypeptide disclosed herein may cause a statistically significant decrease in fat mass in a mouse fed a high fat diet after four weeks of treatment twice per week at a dose level of 10 mg/kg. The mean decrease in fat mass may be 5, 7, 10, 15 or more grams. An ActRIIB polypeptide disclosed herein may cause a statistically significant decrease in serum triglyceride levels in a mouse fed a high fat diet after four weeks of treatment twice per week at a dose level of 10 mg/kg. The mean decrease in serum triglycerides may be at least 50, 75, 100, 125 or 150 or more mg/dl. An ActRIIB polypeptide disclosed herein may cause a statistically significant decrease in serum free fatty acid levels in a mouse fed a high fat diet after four weeks of treatment twice per week at a dose level of 10 mg/kg. The mean decrease in free fatty acids may be at least 500, 750, 1000 or more micromoles/dl free fatty acids. An ActRIIB polypeptide disclosed herein may cause a statistically significant decrease in serum insulin levels in a mouse fed a high fat diet after four weeks of treatment twice per week at a dose level of 10 mg/kg. The mean decrease in serum insulin may be at least 0.5, 1, 1.5, 2 or more ng/ml insulin. As used herein, the term "statistically significant" generally refers to a p value or >0.05, but other measures of significance may be recognized for different types of statistical tests, and in such cases, the term "statistically significant" should use the most widely used formula for assessing the significance of the data. ActRIIB polypeptides may comprise at least one N-linked sugar, and may include two, three or more N-linked sugars. Such polypeptides may also comprise O-linked sugars. ActRIIB polypeptides may be produced in a variety of cell lines that glycosylate the protein in a manner that is suitable for patient use, including engineered insect or yeast cells, and mammalian cells such as COS cells, CHO cells, HEK cells and NSO cells. ActRIIB polypeptides may form covalent or non-covalent dimers, including homodimers. Generally, Fc fusion proteins tend to form homodimers that are covalently linked. Any of the foregoing polypeptides may be incorporated into a pharmaceutical preparation.

In certain aspects, the ActRIIB polypeptides disclosed herein bind to an ActRIIB ligand such as GDF8, GDF11, activin, BMP7, GDF3 or nodal. Optionally, an ActRIIB polypeptide binds to an ActRIIB ligand with a Kd less than 10 micromolar or less than 1 micromolar, 100, 10, 1 or 0.1 nanomolar. An ActRIIB polypeptide disclosed herein may include one, two, three, four, five or more alterations in the amino acid sequence (e.g., in the ligand-binding domain) relative to a naturally occurring ActRIIB polypeptide. The alteration in the amino acid sequence may, for example, alter glycosylation of the polypeptide when produced in a mammalian, insect or other eukaryotic cell or alter proteolytic cleavage of the polypeptide relative to the naturally occurring ActRIIB polypeptide. An ActRIIB polypeptide may be a fusion protein that has, as one domain, an amino acid sequence derived from ActRIIB (e.g., a ligand-binding domain of an ActRIIB or a variant thereof) and one or more additional domains that provide a desirable property, such as improved pharmacokinetics, easier purification, targeting to particular tissues, etc. For example, a domain of a fusion protein may enhance one or more of in vivo stability, in vivo half life, uptake/administration, tissue localization or distribution, formation of protein complexes, multimerization of the fusion protein, and/or purification. An ActRIIB fusion protein may include an immunoglobulin Fc domain (wild-type or mutant) or a serum albumin. In certain embodiments, an ActRIIB-Fc fusion comprises a relatively unstructured linker positioned between the Fc domain and the extracellular ActRIIB domain. This unstructured linker may correspond to the roughly 15 amino acid unstructured region at the C-terminal end of the extracellular domain of ActRIIB (the "tail"), or it may be an artificial sequence of between 5 and 15, 20, 30, 50 or more amino acids that are relatively free of secondary structure. A linker may be rich in glycine and proline residues and may, for example, contain repeating sequences of threonine/serine and glycines (e.g., $TG_4$ (SEQ ID NO: 11) or $SG_4$ (SEQ ID NO: 12) repeats). In the context of a polypeptide of SEQ ID NO:8, it appears to be advantageous to use a short, flexible linker, such as one, two, three, four or five glycine residues, optionally with one or more small residues such as alanine, threonine or serine. A fusion protein may include a purification subsequence, such as an epitope tag, a FLAG tag, a polyhistidine sequence, and a GST fusion. Optionally, an ActRIIB polypeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent.

In certain aspects, an ActRIIB polypeptide may be formulated as a pharmaceutical preparation. A pharmaceutical preparation will preferably be pyrogen free (meaning pyrogen free to the extent required by regulations governing the quality of products for therapeutic use). A pharmaceutical preparation may also include one or more additional compounds such as a compound that is used to treat an ActRIIB-associated disorder.

In certain aspects, the disclosure provides nucleic acids encoding an ActRIIB polypeptide. Such a nucleic acid may comprises a nucleic acid sequence of 73-396 of SEQ ID NO:4 or one that hybridizes under stringent conditions to the complement of nucleotides 73-396 of SEQ ID NO:4. A nucleic acid may one that comprises the sequence of SEQ ID NO:4. Such a nucleic acid may comprises a nucleic acid sequence of 73-396 of SEQ ID NO:6 or one that hybridizes under stringent conditions to the complement of nucleotides 73-396 of SEQ ID NO:6. A nucleic acid may one that comprises the sequence of SEQ ID NO:6. In certain aspects, an ActRIIB protein may be expressed in a mammalian cell line that mediates suitably natural glycosylation of the ActRIIB protein so as to diminish the likelihood of an unfavorable immune response in a patient (including the possibility of veterinary patients). Human and CHO cell lines have been used successfully, and it is expected that other common mammalian expression vectors will be useful. Thus the disclosure provides cultured cells comprising any of the nucleic acids disclosed herein. Such cells may be mammalian cells, including CHO cells, NSO cells, HEK cells and COS cells. Other cells may be chosen depending on the species of the intended patient. Other cells are disclosed herein. Cultured cells are understood to mean cells maintained in laboratory or other man-made conditions (e.g., frozen, or in media) and not part of a living organism.

In certain aspects, the disclosure provides methods for making a ActRIIB polypeptide. Such a method may include expressing any of the nucleic acids (e.g., SEQ ID NO: 4 or 6, and nucleic acids that hybridize thereto under stringent conditions) disclosed herein in a suitable cell, such as a Chinese hamster ovary (CHO) cell. Such a method may comprise: a) culturing a cell under conditions suitable for expression of the ActRIIB polypeptide, wherein said cell is transformed with an ActRIIB expression construct; and b) recovering the ActRIIB polypeptide so expressed. ActRIIB polypeptides may be recovered as crude, partially purified or highly purified fractions using any of the well known techniques for obtaining protein from cell cultures as well as techniques described herein.

In certain aspects the disclosure provides methods for treating a subject having a disorder associated with muscle loss or insufficient muscle growth. Such a method may comprise administering to the subject an effective amount of any of the foregoing ActRIIB polypeptides or pharmaceutical preparations thereof.

In certain aspects the disclosure provides methods for increasing the lean mass or reducing the rate of loss of lean mass in a subject in need thereof. Such a method may comprise administering to the subject an effective amount of any of the foregoing ActRIIB polypeptides or pharmaceutical preparations thereof.

In certain aspects, the disclosure provides methods for decreasing the body fat content or reducing the rate of increase in body fat content in a subject. Such a method may comprise administering to the subject an effective amount of any of the foregoing ActRIIB polypeptides or pharmaceutical preparations thereof.

In certain aspects, the disclosure provides methods for treating a disorder associated with undesirable body weight gain in a subject. Such a method may comprise administering to the subject an effective amount of any of the foregoing ActRIIB polypeptides or pharmaceutical preparations thereof.

In certain aspects, the disclosure provides methods for treating a metabolic disorder in a subject. Such a method may comprise administering to the subject an effective amount of any of the foregoing ActRIIB polypeptides or pharmaceutical preparations thereof. A patient eligible for treatment may have one or more of the following characteristics: elevated serum triglyceride levels; elevated free fatty acid levels; or elevated serum insulin levels. Examples of metabolic disorders include type 2 diabetes, metabolic syndrome, insulin resistance and obesity.

In certain aspects, an ActRIIB polypeptide disclosed herein may be used in a method for treating a subject having a disorder associated with muscle loss or insufficient muscle growth. Such disorders include muscle atrophy, muscular dystrophy, amyotrophic lateral sclerosis (ALS), and a muscle wasting disorder (e.g., cachexia, anorexia, DMD syndrome, BMD syndrome, AIDS wasting syndrome, muscular dystrophies, neuromuscular diseases, motor neuron diseases, diseases of the neuromuscular junction, and inflammatory myopathies). A method may comprise administering to a subject in need thereof an effective amount of an ActRIIB polypeptide.

In certain aspects, an ActRIIB polypeptide disclosed herein may be used in a method for decreasing the body fat content or reducing the rate of increase in body fat content, and for treating a disorder associated with undesirable body weight gain, such as obesity, non-insulin dependent diabetes mellitus (NIDDM), cardiovascular disease, cancer, hypertension, osteoarthritis, stroke, respiratory problems, and gall bladder disease. These methods may comprise administering to a subject in need thereof an effective amount of an ActRIIB polypeptide.

In certain specific aspects, an ActRIIB polypeptide disclosed herein may be used in a method for treating a disorder associated with abnormal activity of GDF8. Such disorders include metabolic disorders such as type 2 diabetes, impaired glucose tolerance, metabolic syndrome (e.g., syndrome X), and insulin resistance induced by trauma (e.g., burns or nitrogen imbalance); adipose tissue disorders (e.g., obesity); muscular dystrophy (including Duchenne muscular dystrophy); amyotrophic lateral sclerosis (ALS); muscle atrophy; organ atrophy; frailty; carpal tunnel syndrome; congestive obstructive pulmonary disease; sarcopenia, cachexia and other muscle wasting syndromes; osteoporosis; glucocorticoid-induced osteoporosis; osteopenia; osteoarthritis; osteoporosis-related fractures; low bone mass due to chronic glucocorticoid therapy, premature gonadal failure, androgen suppression, vitamin D deficiency, secondary hyperparathyroidism, nutritional deficiencies, and anorexia nervosa. The method may comprise administering to a subject in need thereof an effective amount of an ActRIIB polypeptide.

In certain aspects, the disclosure provides a method for identifying an agent that stimulates growth of a tissue such as bone, cartilage, muscle and fat. The method comprises: a) identifying a test agent that binds to a ligand-binding domain of an ActRIIB polypeptide competitively with an ActRIIB polypeptide; and b) evaluating the effect of the agent on growth of the tissue.

In certain aspects, the disclosure provides methods for antagonizing activity of an ActRIIB polypeptide or an ActRIIB ligand (e.g., GDF8, GDF11, activin, GDF3, BMP7, and Nodal) in a cell. The methods comprise contacting the cell with an ActRIIB polypeptide. Optionally, the activity of the ActRIIB polypeptide or the ActRIIB ligand is monitored by a signaling transduction mediated by the ActRIIB/ActRIIB ligand complex, for example, by monitoring cell proliferation. The cells of the methods include an osteoblast, a chondrocyte, a myocyte, an adipocyte and a muscle cell.

In certain aspects, the disclosure provides uses of an ActRIIB polypeptide for making a medicament for the treatment of a disorder or condition as described herein.

BRIEF DESCRIPTION OF THE DRAWINGS

The patent or application file contains at least one drawing executed in color. Copies of this patent or patent application publication with color drawing(s) will be provided by the Patent Office upon request and payment of the necessary fee.

FIG. 1 shows the full, unprocessed amino acid sequence for ActRIIB(25-131)-hFc (SEQ ID NO:3). The TPA leader (residues 1-22) and double-truncated ActRIIB extracellular domain (residues 24-131, using numbering based on the native sequence in SEQ ID NO:1) are each underlined. Highlighted is the glutamate revealed by sequencing to be the N-terminal amino acid of the mature fusion protein, which is at position 25 relative to SEQ ID NO:1.

FIG. 2 shows a nucleotide sequence encoding ActRIIB(25-131)-hFc (the coding strand is shown at top, SEQ ID NO:4, and the complement shown at bottom 3'-5', SEQ ID NO:5). Sequences encoding the TPA leader (nucleotides 1-66) and ActRIIB extracellular domain (nucleotides 73-396) are underlined. The corresponding amino acid sequence (SEQ ID NO: 14) for ActRIIB(25-131) is also shown.

FIG. 3 shows an alternative nucleotide sequence encoding ActRIIB(25-131)-hFc (the coding strand is shown at top, SEQ ID NO:6, and the complement shown at bottom 3'-5', SEQ ID NO:7). This sequence confers a greater level of protein expression in initial transformants, making cell line development a more rapid process. Sequences encoding the TPA leader (nucleotides 1-66) and ActRIIB extracellular domain (nucleotides 73-396) are underlined, and substitutions in the wild type nucleotide sequence of the ECD (see FIG. 2) are highlighted. The corresponding amino acid sequence (SEQ ID NO: 15) for ActRIIB(25-131) is also shown.

DETAILED DESCRIPTION

1. Overview

Figure 4:
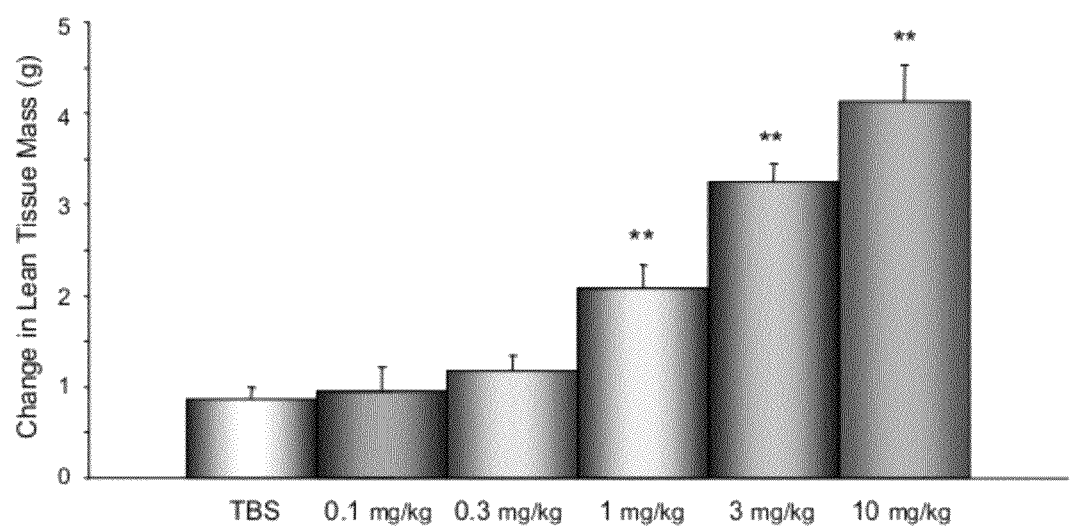
FIG. 4 shows the effect of four weeks treatment with ActRIIB(25-131)-hFc on lean tissue mass in mouse. Vehicle was Tris-buffered saline (TBS). Data are means (n=10 per group)±SEM. **, P<0.01 vs. TBS by unpaired t-test. ActRIIB (25-131)-hFc treatment increased lean tissue mass in a clear dose-dependent manner.

In certain aspects, the present disclosure relates to ActRIIB polypeptides. As used herein, the term "ActRIIB" refers to a family of activin receptor type IIB (ActRIIB) proteins and ActRIIB-related proteins, derived from any species. Members of the ActRIIB family are generally all transmembrane proteins, composed of a ligand-binding extracellular domain with cysteine-rich region, a transmembrane domain, and a cytoplasmic domain with predicted serine/threonine kinase specificity.

The term "ActRIIB polypeptide" is used to refer to polypeptides comprising any naturally occurring polypeptide of an ActRIIB family member as well as any variants thereof (including mutants, fragments, fusions, and peptidomimetic forms) that retain a useful activity. For example, ActRIIB polypeptides include polypeptides derived from the sequence of any known ActRIIB having a sequence at least about 80% identical to the sequence of an ActRIIB polypeptide, and preferably at least 85%, 90%, 95%, 97%, 99% or greater identity.

The human ActRIIB precursor has the following amino acid sequence, with the signal peptide underlined, the extracellular domain indicated in bold, and the potential N-linked glycosylation sites boxed (SEQ ID NO: 1) (NM_001106, 512 aa).

MTAPWVALALLWGSLWPGSGRGEAETRECIYYNANWELERT NQSGLER

CEGEQDKRLHCYASWR NSSGTIELVKKGCWLDDFNCYDRQECVATEEN

PQVYFCCCEGNFCNERFTHLPEAGGPEVTYEPPPTAPTLLTVLAYSLL

PIGGLSLIVLLAFWMYRHRKPPYGHVDIHEDPGPPPPSPLVGLKPLQL

LEIKARGRFGCVWKAQLMNDFVAVKIFPLQDKQSWQSEREIFSTPGMK

HENLLQFIAAEKRGSNLEVELWLITAFHDKGSLTDYLKGNIITWNELC

HVAETMSRGLSYLHEDVPWCRGEGHKPSIAHRDFKSKNVLLKSDLTAV

LADFGLAVRFEPGKPPGDTHGQVGTRRYMAPEVLEGAINFQRDAFLRI

DMYAMGLVLWELVSRCKAADGPVDEYMLPFEEEIGQHPSLEELQEVVV

HKKMRPTIKDHWLKHPGLAQLCVTIEECWDHDAEARLSAGCVEERVSL

IRRSVNGTTSDCLVSLVTSVTNVDLPPKESSI

ActRIIB polypeptides may include any naturally occurring extracellular domain of an ActRIIB protein as well as any variants thereof (including mutants, fragments and peptidomimetic forms) that retain a useful activity. For example, the extracellular domain of an ActRIIB protein binds to a ligand and is generally soluble. The signal sequence can be a native signal sequence of an ActRIIB, or a signal sequence from another protein, such as a tissue plasminogen activator (TPA) signal sequence or a honey bee melatin (HBM) signal sequence.

In part the disclosure provides a novel ActRIIB polypeptide that is truncated, such that the portion derived from ActRIIB is from amino acids 25-131 of SEQ ID NO:1. As shown herein, polypeptides of this type when administered as an Fc construct, ActRIIB(25-131)-hFc, promote the formation of lean body mass (primarily muscle) and the loss of fat mass, while also having marked desirable effects on metabolic parameters such as serum triglycerides, serum free fatty acids and serum insulin levels. Remarkably, ActRIIB(25-131)-hFc has a much greater effect on these metabolic parameters than does a related protein, ActRIIB(20-134). These data are presented in the Examples below.

TGF-β signals are mediated by heteromeric complexes of type I and type II serine/threonine kinase receptors, which phosphorylate and activate downstream Smad proteins upon ligand stimulation (Massagué, 2000, Nat. Rev. Mol. Cell Biol. 1:169-178). These type I and type II receptors are all transmembrane proteins, composed of a ligand-binding extracellular domain with cysteine-rich region, a transmembrane domain, and a cytoplasmic domain with predicted serine/threonine specificity. Type I receptors are essential for signaling; and type II receptors are required for binding ligands and for expression of type I receptors. Type I and II activin receptors form a stable complex after ligand binding, resulting in phosphorylation of type I receptors by type II receptors.

Two related type II receptors, ActRIIA and ActRIIB, have been identified as the type II receptors for activins (Mathews and Vale, 1991, Cell 65:973-982; Attisano et al., 1992, Cell 68: 97-108). Besides activins, ActRIIA and ActRIIB can biochemically interact with several other TGF-β family proteins, including BMP7, Nodal, GDF8, and GDF11 (Yamashita et al., 1995, J. Cell Biol. 130:217-226; Lee and McPherron, 2001, Proc. Natl. Acad. Sci. 98:9306-9311; Yeo and Whitman, 2001, Mol. Cell 7: 949-957; Oh et al., 2002, Genes Dev. 16:2749-54).

In certain embodiments, the present invention relates to antagonizing a ligand of ActRIIB receptors (also referred to as an ActRIIB ligand) with a subject ActRIIB polypeptide (e.g., an ActRIIB-Fc polypeptide). Thus, compositions and methods of the present invention are useful for treating disorders associated with abnormal activity of one or more ligands of ActRIIB receptors. Exemplary ligands of ActRIIB receptors include some TGF-β family members, such as activin, Nodal, GDF3, GDF8, GDF11, and BMP7.

Activins are dimeric polypeptide growth factors and belong to the TGF-beta superfamily. There are three activins (A, B, and AB) that are homo/heterodimers of two closely related β subunits ($\beta_A\beta_A$, $\beta_B\beta_B$, and $\beta_A\beta_B$). In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos (DePaolo et al., 1991, Proc SocEp Biol Med. 198: 500-512; Dyson et al., 1997, Curr Biol. 7:81-84; Woodruff, 1998, Biochem Pharmacol. 55:953-963). Moreover, erythroid differentiation factor (EDF) isolated from the stimulated human monocytic leukemic cells was found to be identical to activin A (Murata et al., 1988, PNAS, 85:2434). It was suggested that activin A acts as a natural regulator of erythropoiesis in the bone marrow. In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Other proteins that may regulate activin bioactivity and/or bind to activin include follistatin (FS), follistatin-related protein (FSRP), $\alpha_2$-macroglobulin, Cerberus, and endoglin, which are described below.

Bone morphogenetic protein 7 (BMP7), also called osteogenic protein-1 (OP-1), is well known to induce cartilage and bone formation. In addition, BMP7 regulates a wide array of physiological processes. Notably, BMP7 has recently been identified as a key promoter of brown adipocyte differentiation (Tseng et al., 2008, Nature 454:1000-1004). In this study, genetic ablation of BMP7 led to scarcity of brown fat and nearly complete absence of UCP1 in murine embryos. Moreover, upregulation of BMP7 expression in mice by adenovirus administration increased brown fat mass and energy expenditure. Like activin, BMP7 binds to type II receptors, ActRIIA and ActRIIB. However, BMP7 and activin recruit distinct type I receptors into heteromeric receptor complexes. The major BMP7 type I receptor observed was ALK2, while activin bound exclusively to ALK4 (ActRIIB). BMP7 and activin elicited distinct biological responses and activated different Smad pathways (Macias-Silva et al., 1998, J Biol Chem. 273:25628-36).

Growth-and-Differentiation Factor-3 (GDF3), also known as Vg1-related 2, plays an important role in embryonic development and has also been implicated in adipogenesis during adulthood. In brief, expression of GDF3 in white adipose tissue is correlated with body mass or obesity (Weisberg et al., 2003, J Clin Invest 112:1796-1808), and adenovirus-mediated overexpression of GDF3 exaggerates the increase in adiposity observed under high-fat dietary conditions in wild-type mice (Wang et al., 2004, Biochem Biophys Res Commun 321:1024-1031) Importantly, mice with genetic ablation of GDF3 are healthy and essentially normal when maintained on a standard diet but are protected from obesity, and display an increased basal metabolic rate, when maintained on a high-fat diet (Shen et al., 2009, Mol Endocrinol 23:113-123). Taken together, these findings implicate GDF3 specifically in diet-induced obesity and more generally in the regulation of adiposity.

Nodal proteins have functions in mesoderm and endoderm induction and formation, as well as subsequent organization of axial structures such as heart and stomach in early embryogenesis. It has been demonstrated that dorsal tissue in a developing vertebrate embryo contributes predominantly to the axial structures of the notochord and pre-chordal plate while it recruits surrounding cells to form non-axial embryonic structures. Nodal appears to signal through both type I and type II receptors and intracellular effectors known as Smad proteins. Recent studies support the idea that ActRIIA and ActRIIB serve as type II receptors for Nodal (Sakuma et al., Genes Cells. 2002, 7:401-12). It is suggested that Nodal ligands interact with their co-factors (e.g., cripto) to activate activin type I and type II receptors, which phosphorylate Smad2. Nodal proteins are implicated in many events critical to the early vertebrate embryo, including mesoderm formation, anterior patterning, and left-right axis specification. Experimental evidence has demonstrated that Nodal signaling activates pAR3-Lux, a luciferase reporter previously shown to respond specifically to activin and TGF-beta. However, Nodal is unable to induce pTlx2-Lux, a reporter specifically responsive to bone morphogenetic proteins. Recent results provide direct biochemical evidence that Nodal signaling is mediated by both activin-TGF-beta pathway Smads, Smad2 and Smad3. Further evidence has shown that the extracellular cripto protein is required for Nodal signaling, making it distinct from activin or TGF-beta signaling.

Growth and Differentiation Factor-8 (GDF8) is also known as myostatin. GDF8 is a negative regulator of skeletal muscle mass. GDF8 is highly expressed in the developing and adult skeletal muscle. The GDF8 null mutation in transgenic mice is characterized by a marked hypertrophy and hyperplasia of the skeletal muscle (McPherron et al., Nature, 1997, 387:83-90). Similar increases in skeletal muscle mass are evident in naturally occurring mutations of GDF8 in cattle (Ashmore et al., 1974, Growth, 38:501-507; Swatland and Kieffer, J. Anim Sci., 1994, 38:752-757; McPherron and Lee, Proc. Natl. Acad. Sci. USA, 1997, 94:12457-12461; and Kambadur et al., Genome Res., 1997, 7:910-915) and, strikingly, in humans (Schuelke et al., N Engl J Med 2004; 350:2682-8). Studies have also shown that muscle wasting associated with HIV-infection in humans is accompanied by increases in GDF8 protein expression (Gonzalez-Cadavid et al., PNAS, 1998, 95:14938-43). In addition, GDF8 can modulate the production of muscle-specific enzymes (e.g., creatine kinase) and modulate myoblast cell proliferation (WO 00/43781). The GDF8 propeptide can noncovalently bind to the mature GDF8 domain dimer, inactivating its biological activity (Miyazono et al. (1988) J. Biol. Chem., 263: 6407-6415; Wakefield et al. (1988) J. Biol. Chem., 263; 7646-7654; and Brown et al. (1990) Growth Factors, 3: 35-43). Other proteins which bind to GDF8 or structurally related proteins and inhibit their biological activity include follistatin, and potentially, follistatin-related proteins (Gamer et al. (1999) Dev. Biol., 208: 222-232).

Growth and Differentiation Factor-11 (GDF11), also known as BMP11, is a secreted protein (McPherron et al., 1999, Nat. Genet. 22: 260-264). GDF11 is expressed in the tail bud, limb bud, maxillary and mandibular arches, and dorsal root ganglia during mouse development (Nakashima et al., 1999, Mech. Dev. 80: 185-189). GDF11 plays a unique role in patterning both mesodermal and neural tissues (Gamer et al., 1999, Dev Biol., 208:222-32). GDF11 was shown to be a negative regulator of chondrogenesis and myogenesis in developing chick limb (Gamer et al., 2001, Dev Biol. 229: 407-20). The expression of GDF11 in muscle also suggests its role in regulating muscle growth in a similar way to GDF8. In addition, the expression of GDF11 in brain suggests that GDF11 may also possess activities that relate to the function of the nervous system. Interestingly, GDF11 was found to inhibit neurogenesis in the olfactory epithelium (Wu et al., 2003, Neuron. 37:197-207). Hence, GDF11 may have in vitro and in vivo applications in the treatment of diseases such as muscle diseases and neurodegenerative diseases (e.g., amyotrophic lateral sclerosis).

In certain aspects, the present invention relates to the use of certain ActRIIB polypeptides to antagonize the signaling of ActRIIB ligands generally, in any process associated with ActRIIB activity. Optionally, ActRIIB polypeptides of the invention may antagonize one or more ligands of ActRIIB receptors, such as activin, Nodal, GDF8, GDF11, and BMP7, and may therefore be useful in the treatment of additional disorders.

Therefore, the present invention contemplates using ActRIIB polypeptides in treating or preventing diseases or conditions that are associated with abnormal activity of an ActRIIB or an ActRIIB ligand. ActRIIB or ActRIIB ligands are involved in the regulation of many critical biological processes. Due to their key functions in these processes, they may be desirable targets for therapeutic intervention. For example, ActRIIB polypeptides (e.g., ActRIIB-Fc polypeptides) may be used to treat human or animal disorders or conditions. Example of such disorders or conditions include, but are not limited to, metabolic disorders such as type 2 diabetes, impaired glucose tolerance, metabolic syndrome (e.g., syndrome X), and insulin resistance induced by trauma (e.g., burns or nitrogen imbalance); adipose tissue disorders (e.g., obesity); muscle and neuromuscular disorders such as muscular dystrophy (including Duchenne muscular dystrophy); amyotrophic lateral sclerosis (ALS); muscle atrophy; organ atrophy; frailty; carpal tunnel syndrome; congestive obstructive pulmonary disease; and sarcopenia, cachexia and other muscle wasting syndromes. Other examples include osteoporosis, especially in the elderly and/or postmenopausal women; glucocorticoid-induced osteoporosis; osteopenia; osteoarthritis; and osteoporosis-related fractures. Yet further examples include low bone mass due to chronic glucocorticoid therapy, premature gonadal failure, androgen suppression, vitamin D deficiency, secondary hyperparathyroidism, nutritional deficiencies, and anorexia nervosa. These disorders and conditions are discussed below under "Exemplary Therapeutic Uses." As noted, the truncated ActRIIB polypeptides disclosed herein appear to have particularly beneficial effects on metabolic parameters.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "A") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

2. ActRIIB Polypeptides

In certain aspects, the invention relates to ActRIIB polypeptides (e.g., ActRIIB-Fc polypeptides), and particularly truncated forms exemplified by polypeptides comprising amino acids 25-131 of SEQ ID NO:1, and variants thereof. Optionally, the fragments, functional variants, and modified forms have similar or the same biological activities of their corresponding wild-type ActRIIB polypeptides. For example, an ActRIIB variant of the invention may bind to and inhibit function of an ActRIIB ligand (e.g., activin A, activin AB, activin B, Nodal, GDF8, GDF11 or BMP7). Optionally, an ActRIIB polypeptide modulates growth of tissues such as bone, cartilage, muscle or fat or metabolic parameters such as triglycerides, free fatty acids or insulin. Examples of ActRIIB polypeptides include human ActRIIB precursor polypeptide (SEQ ID NO: 1), and Fc fusion proteins, e.g., SEQ ID Nos. 3 and 8. Variations on these polypeptides may be prepared according to the following guidance. The numbering of amino acids in the ActRIIB polypeptides is based on the sequence of SEQ ID NO:1, regardless of whether the native leader sequence is used.

The disclosure identifies functionally active portions and variants of ActRIIB. Applicants have ascertained that an Fc fusion protein having the sequence disclosed by Hilden et al. (Blood. 1994 Apr. 15; 83(8):2163-70), which has an Alanine at the position corresponding to amino acid 64 of SEQ ID NO: 1 (A64), has a relatively low affinity for activin and GDF-11. By contrast, the same Fc fusion protein with an Arginine at position 64 (R64) has an affinity for activin and GDF-11 in the low nanomolar to high picomolar range. Therefore, a sequence with an R64 is used as the wild-type reference sequence for human ActRIIB in this disclosure.

Attisano et al. (Cell. 1992 Jan. 10; 68(1):97-108) showed that a deletion of the proline knot at the C-terminus of the extracellular domain of ActRIIB reduced the affinity of the receptor for activin. Mutations of P129 and P130 do not substantially decrease ligand binding.

The ActRIIB ligand binding pocket is defined by residues Y31, N33, N35, L38 through T41, E47, E50, Q53 through K55, L57, H58, Y60, S62, K74, W78 through N83, Y85, R87, A92, and E94 through F101. At these positions, it is expected that conservative mutations will be tolerated, although a K74A mutation is well-tolerated, as are R40A, K55A, F82A and mutations at position L79. R40 is a K in *Xenopus*, indicating that basic amino acids at this position will be tolerated. Q53 is R in bovine ActRIIB and K in *Xenopus* ActRIIB, and therefore amino acids including R, K, Q, N and H will be tolerated at this position. Thus, an ActRIIB protein may be one that comprises amino acids 25-131 and comprising no more than 1, 2, 5, 10 or 15 conservative amino acid changes in the ligand binding pocket, and zero, one or more non-conservative alterations at positions 40, 53, 55, 74, 79 and/or 82 in the ligand binding pocket. Such a protein may retain greater than 80%, 90%, 95% or 99% sequence identity to the sequence of amino acids 25-131 of SEQ ID NO:1. Sites outside the binding pocket, at which variability may be particularly well tolerated, include the amino and carboxy termini of the extracellular domain (as noted above), and positions 42-46 and 65-73. An asparagine to alanine alteration at position 65 (N65A) actually improves ligand binding in the A64 background, and is thus expected to have no detrimental effect on ligand binding in the R64 background. This change probably eliminates glycosylation at N65 in the A64 background, thus demonstrating that a significant change in this region is likely to be tolerated. While an R64A change is poorly tolerated, R64K is well-tolerated, and thus another basic residue, such as H may be tolerated at position 64.

ActRIIB is well-conserved across nearly all vertebrates, with large stretches of the extracellular domain conserved completely. Many of the ligands that bind to ActRIIB are also highly conserved. Accordingly, comparisons of ActRIIB sequences from various vertebrate organisms provide insights into residues that may be altered. Therefore, an active, human ActRIIB may include one or more amino acids at corresponding positions from the sequence of another vertebrate ActRIIB, or may include a residue that is similar to that in the human or other vertebrate sequence. The following examples illustrate this approach to defining an active ActRIIB variant. L46 is a valine in *Xenopus* ActRIIB, and so this position may be altered, and optionally may be altered to another hydrophobic residue, such as V, I or F, or a non-polar residue such as A. E52 is a K in *Xenopus*, indicating that this site may be tolerant of a wide variety of changes, including polar residues, such as E, D, K, R, H, S, T, P, G, Y and probably A. T93 is a K in *Xenopus*, indicating that a wide structural variation is tolerated at this position, with polar residues favored, such as S, K, R, E, D, H, G, P, G and Y. F108 is a Y in *Xenopus*, and therefore Y or other hydrophobic group, such as I, V or L should be tolerated. E111 is K in *Xenopus*, indicating that charged residues will be tolerated at this position, including D, R, K and H, as well as Q and N. R112 is K in *Xenopus*, indicating that basic residues are tolerated at this position, including R and H. A at position 119 is relatively poorly conserved, and appears as P in rodents and V in *Xenopus*, thus essentially any amino acid should be tolerated at this position.

Further N-linked glycosylation sites (N-X-S/T) may be added to an ActRIIB polypeptide, and may increase the serum half-life of an ActRIIB-Fc fusion protein, relative to the ActRIIB(R64)-Fc form. Examples of NX(T/S) sequences are found at 42-44 (NQS) and 65-67 (NSS), although the latter may not be efficiently glycosylated with the R at position 64. N-X-S/T sequences may be generally introduced at positions outside the ligand binding pocket. Particularly suitable sites for the introduction of non-endogenous N-X-S/T sequences include amino acids 20-29, 20-24, 22-25, 109-134, 120-134 or 129-134. N-X-S/T sequences may also be introduced into the linker between the ActRIIB sequence and the Fc or other fusion component. Such a site may be introduced with minimal effort by introducing an N in the correct position with respect to a pre-existing S or T, or by introducing an S or T at a position corresponding to a pre-existing N. Thus, desirable alterations that would create an N-linked glycosylation site are: A24N, R64N, S67N (possibly combined with an N65A alteration), E106N, R112N, G120N, E123N, P129N, A132N, R112S and R112T. Any S that is predicted to be glycosylated may be altered to a T without creating an immunogenic site, because of the protection afforded by the glycosylation. Likewise, any T that is predicted to be glycosylated may be altered to an S. Thus the alterations S67T and S44T are contemplated. Likewise, in an A24N variant, an S26T alteration may be used. Accordingly, an ActRIIB variant may include one or more additional, non-endogenous N-linked glycosylation consensus sequences.

The variations described may be combined in various ways. Additionally, there are amino acid positions in ActRIIB that are often beneficial to conserve. These include position 64 (basic amino acid), position 80 (acidic or hydrophobic amino acid), position 78 (hydrophobic, and particularly tryptophan), position 37 (acidic, and particularly aspartic or glutamic acid), position 56 (basic amino acid), position 60 (hydrophobic amino acid, particularly phenylalanine or tyrosine). Other positions that may be desirable to conserve are as follows: position 52 (acidic amino acid), position 55 (basic amino acid), position 81 (acidic), 98 (polar or charged, particularly E, D, R or K).

In certain embodiments, the present invention contemplates making functional variants by modifying the structure of an ActRIIB polypeptide for such purposes as enhancing therapeutic efficacy, or stability (e.g., ex vivo shelf life and resistance to proteolytic degradation in vivo). Modified ActRIIB polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an ActRIIB polypeptide results in a functional homolog can be readily determined by assessing the ability of the variant ActRIIB polypeptide to produce a response in cells in a fashion similar to the wildtype ActRIIB polypeptide, or to bind to one or more ligands, such as activin, GDF-11 or myostatin in a fashion similar to wild type.

In certain specific embodiments, the present invention contemplates making mutations in the extracellular domain (also referred to as ligand-binding domain) of an ActRIIB polypeptide such that the variant (or mutant) ActRIIB polypeptide has altered ligand-binding activities (e.g., binding affinity or binding specificity). In certain cases, such variant ActRIIB polypeptides have altered (elevated or reduced) binding affinity for a specific ligand. In other cases, the variant ActRIIB polypeptides have altered binding specificity for their ligands.

In certain embodiments, the present invention contemplates specific mutations of the ActRIIB polypeptides so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (where "X" is any amino acid) which is specifically recognized by appropriate cellular glycosylation enzymes. The alteration may also be made by the addition of, or substitution by, one or more serine or threonine residues to the sequence of the wild-type ActRIIB polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ActRIIB polypeptide is by chemical or enzymatic coupling of glycosides to the ActRIIB polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on an ActRIIB polypeptide may be accomplished chemically and/or enzymatically. Chemical deglycosylation may involve, for example, exposure of the ActRIIB polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on ActRIIB polypeptides can be achieved by the use of a variety of endo- and exo-glycosidases as described by Thotakura et al. (1987) Meth. Enzymol. 138:350. The sequence of an ActRIIB polypeptide may be adjusted, as appropriate, depending on the type of expression system used, as mammalian, yeast, insect and plant cells may all introduce differing glycosylation patterns that can be affected by the amino acid sequence of the peptide. In general, ActRIIB proteins for use in humans will be expressed in a mammalian cell line that provides proper glycosylation, such as HEK293 or CHO cell lines, although other mammalian expression cell lines are expected to be useful as well.

This disclosure further contemplates a method of generating variants, particularly sets of combinatorial variants of an ActRIIB polypeptide, including, optionally, truncation variants; pools of combinatorial mutants are especially useful for identifying functional variant sequences. The purpose of screening such combinatorial libraries may be to generate, for example, ActRIIB polypeptide variants which have altered properties, such as altered pharmacokinetics, or altered ligand binding. A variety of screening assays are provided below, and such assays may be used to evaluate variants. For example, an ActRIIB polypeptide variant may be screened for ability to bind to an ActRIIB polypeptide, to prevent binding of an ActRIIB ligand to an ActRIIB polypeptide.

The activity of an ActRIIB polypeptide or its variants may also be tested in a cell-based or in vivo assay. For example, the effect of an ActRIIB polypeptide variant on the expression of genes involved in bone production in an osteoblast or precursor may be assessed. This may, as needed, be performed in the presence of one or more recombinant ActRIIB ligand protein (e.g., BMP7), and cells may be transfected so as to produce an ActRIIB polypeptide and/or variants thereof, and optionally, an ActRIIB ligand. Likewise, an ActRIIB polypeptide may be administered to a mouse or other animal, and one or more bone properties, such as density or volume may be assessed. The healing rate for bone fractures may also be evaluated. Similarly, the activity of an ActRIIB polypeptide or its variants may be tested in muscle cells, adipocytes, and neuronal cells for any effect on growth of these cells, for example, by the assays as described below. Such assays are well known and routine in the art. A SMAD-responsive reporter gene may be used in such cell lines to monitor effects on downstream signaling.

Combinatorially-derived variants can be generated which have a selective potency relative to a naturally occurring ActRIIB polypeptide. Such variant proteins, when expressed from recombinant DNA constructs, can be used in gene therapy protocols. Likewise, mutagenesis can give rise to variants which have intracellular half-lives dramatically different than the corresponding a wild-type ActRIIB polypeptide. For example, the altered protein can be rendered either more stable or less stable to proteolytic degradation or other processes which result in destruction of, or otherwise inactivation of a native ActRIIB polypeptide. Such variants, and the genes which encode them, can be utilized to alter ActRIIB polypeptide levels by modulating the half-life of the ActRIIB polypeptides. For instance, a short half-life can give rise to more transient biological effects and, when part of an inducible expression system, can allow tighter control of recombinant ActRIIB polypeptide levels within the cell.

In certain embodiments, the ActRIIB polypeptides of the invention may further comprise post-translational modifications in addition to any that are naturally present in the ActRIIB polypeptides. Such modifications include, but are not limited to, acetylation, carboxylation, glycosylation, phosphorylation, lipidation, and acylation. As a result, the modified ActRIIB polypeptides may contain non-amino acid elements, such as polyethylene glycols, lipids, poly- or monosaccharide, and phosphates. Effects of such non-amino acid elements on the functionality of a ActRIIB polypeptide may be tested as described herein for other ActRIIB polypeptide variants. When an ActRIIB polypeptide is produced in cells by cleaving a nascent form of the ActRIIB polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the ActRIIB polypeptides.

In certain aspects, functional variants or modified forms of the ActRIIB polypeptides include fusion proteins having at least a portion of the ActRIIB polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (e.g., an Fc), maltose binding protein (MBP), or human serum albumin A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$ (SEQ ID NO: 13)) fusion partners. As another example, a fusion domain may be selected so as to facilitate detection of the ActRIIB polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ActRIIB polypeptide is fused with a domain that stabilizes the ActRIIB polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of muscle growth).

As a specific example, the present invention provides a fusion protein as a GDF8 antagonist which comprises an extracellular (e.g., GDF8-binding) domain fused to an Fc domain (e.g., SEQ ID NO: 9).

```
THTCPPCPAPELLGGPSVFLFPPKPKDTLMISRTPEVTCVVVD(A)VS

HEDPEVKFNWYVDGVEVHNAKTKPREEQYNSTYRVVSVLTVLHQDWLN

GKEYKCK(A)VSNKALPVPIEKTISKAKGQPREPQVYTLPPSREEMTK

NQVSLTCLVKGFYPSDIAVEWESNGQPENNYKTTPPVLDSDGPFFLYS

KLTVDKSRWQQGNVFSCSVMHEALHN(A)HYTQKSLSLSPGK*
```

Optionally, the Fc domain has one or more mutations at residues such as Asp-265, lysine 322, and Asn-434. In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

It is understood that different elements of the fusion proteins may be arranged in any manner that is consistent with the desired functionality. For example, an ActRIIB polypeptide may be placed C-terminal to a heterologous domain, or, alternatively, a heterologous domain may be placed C-terminal to an ActRIIB polypeptide. The ActRIIB polypeptide domain and the heterologous domain need not be adjacent in a fusion protein, and additional domains or amino acid sequences may be included C- or N-terminal to either domain or between the domains.

In certain embodiments, the ActRIIB polypeptides of the present invention contain one or more modifications that are capable of stabilizing the ActRIIB polypeptides. For example, such modifications enhance the in vitro half life of the ActRIIB polypeptides, enhance circulatory half life of the ActRIIB polypeptides or reducing proteolytic degradation of the ActRIIB polypeptides. Such stabilizing modifications include, but are not limited to, fusion proteins (including, for example, fusion proteins comprising an ActRIIB polypeptide and a stabilizer domain), modifications of a glycosylation site (including, for example, addition of a glycosylation site to an ActRIIB polypeptide), and modifications of carbohydrate moiety (including, for example, removal of carbohydrate moieties from an ActRIIB polypeptide). In the case of fusion proteins, an ActRIIB polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

In certain embodiments, the present invention makes available isolated and/or purified forms of the ActRIIB polypeptides, which are isolated from, or otherwise substantially free of, other proteins.

In certain embodiments, ActRIIB polypeptides (unmodified or modified) of the invention can be produced by a variety of art-known techniques. For example, such ActRIIB polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the ActRIIB polypeptides, fragments or variants thereof may be recombinantly produced using various expression systems (e.g., E. coli, Chinese Hamster Ovary cells, COS cells, baculovirus) as is well known in the art (also see below). In a further embodiment, the modified or unmodified ActRIIB polypeptides may be produced by digestion of naturally occurring or recombinantly produced full-length ActRIIB polypeptides by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites. Alternatively, such ActRIIB polypeptides may be produced from naturally occurring or recombinantly produced full-length ActRIIB polypeptides such as standard techniques known in the art, such as by chemical cleavage (e.g., cyanogen bromide, hydroxylamine).

3. Nucleic Acids Encoding ActRIIB Polypeptides

In certain aspects, the invention provides isolated and/or recombinant nucleic acids encoding any of the ActRIIB polypeptides disclosed herein. For example, SEQ ID NO: 4 encodes an ActRIIB(25-131)-hFc precursor polypeptide, while SEQ ID NO: 6 encodes a the same protein but with an alternative sequence, and nucleotides 73-396 of each of SEQ ID Nos. 4 and 6 encode the ActRIIB-derived portion of the encoded proteins. The subject nucleic acids may be single-stranded or double stranded. Such nucleic acids may be DNA or RNA molecules. These nucleic acids are may be used, for example, in methods for making ActRIIB polypeptides.

For example, the following sequence encodes a naturally occurring human ActRIIB precursor polypeptide (SEQ ID NO: 2) (nucleotides 5-1543 of NM_001106, 1539 bp):

```
atgacggcgccctgggtggccctcgccctcctctggggatcgctgtgg
cccggctctgggcgtggggaggctgagacacgggagtgcatctactac
aacgccaactgggagctggagcgcaccaaccagagcggcctggagcgc
tgcgaaggcgagcaggacaagcggctgcactgctacgcctcctggcgc
aacagctctggcaccatcgagctcgtgaagaagggctgctggctagat
gacttcaactgctacgataggcaggagtgtgtggccactgaggagaac
ccccaggtgtacttctgctgctgtgaaggcaacttctgcaacgagcgc
ttcactcatttgccagaggctggggccccggaagtcacgtacgagcca
ccccgacagccccacccctgctcacggtgctggcctactcactgctg
cccatcggggccttccctcatcgtcctgctggccttttggatgtac
cggcatcgcaagccccctacggtcatgtggacatccatgaggaccct
gggcctccaccaccatccctctggtgggcctgaagccactgcagctg
ctggagatcaaggctcgggggcgctttggctgtgtctggaaggcccag
ctcatgaatgactttgtagctgtcaagatcttcccactccaggacaag
cagtcgtggcagagtgaacgggagatcttcagcacacctggcatgaag
cacgagaacctgctacagttcattgctgccgagaagcgaggctccaac
ctcgaagtagagctgtggctcatcacggccttccatgacaagggctcc
ctcacggattacctcaaggggaacatcatcacatggaacgaactgtgt
catgtagcagagacgatgtcacgaggcctctcatacctgcatgaggat
gtgccctggtgccgtggcgagggccacaagccgtctattgcccacagg
gactttaaaagtaagaatgtattgctgaagagcgacctcacagccgtg
ctggctgactttggcttggctgttcgatttgagccagggaaacctcca
ggggacacccacggacaggtaggcacgagacggtacatggctcctgag
gtgctcgagggagccatcaacttccagagagatgccttcctgcgcatt
gacatgtatgccatggggttggtgctgtgggagcttgtgtctcgctgc
aaggctgcagacggaccccgtggatgagtacatgctgccctttgaggaa
gagattggccagcaccttcgttggaggagctgcaggaggtggtggtg
cacaagaagatgaggccaccattaaagatcactggttgaaacaccg
ggcctggcccagctttgtgtgaccatcgaggagtgctgggaccatgat
gcagaggctcgcttgtccgcgggctgtgtggaggagcgggtgtccctg
attcggaggtcggtcaacggcactacctcggactgtctcgtttccctg
gtgacctctgtcaccaatgtggacctgccccctaaagagtcaagcatc
taa
```

The following sequence encodes a human soluble (extra-cellular) ActRIIB polypeptide (SEQ ID NO: 10) (348 bp).

```
tctgggcgtggggaggctgagacacgggagtgcatctactacaacgcc
aactgggagctggagcgcaccaaccagagcggcctggagcgctgcgaa
ggcgagcaggacaagcggctgcactgctacgcctcctggcgcaacagc
tctggcaccatcgagctcgtgaagaagggctgctggctagatgacttc
aactgctacgataggcaggagtgtgtggccactgaggagaaccccag
gtgtacttctgctgctgtgaaggcaacttctgcaacgagcgcttcact
catttgccagaggctggggccccggaagtcacgtacgagccacccccg
acagcccccacc
```

In certain aspects, the subject nucleic acids encoding ActRIIB polypeptides are further understood to include nucleic acids that are variants of SEQ ID NO: 4 or 6. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NO: 4 or 6.

In certain embodiments, the invention provides isolated or recombinant nucleic acid sequences that are at least 80%, 85%, 90%, 95%, 97%, 98%, 99% or 100% identical to SEQ ID NO: 4 or 6, and particularly those portions thereof that are derived from ActRIIB (nucleotides 73-396). One of ordinary skill in the art will appreciate that nucleic acid sequences complementary to SEQ ID NO: 4 or 6, and variants of SEQ ID NO: 4 are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence designated in SEQ ID NO: 4 or 6, complement sequence of SEQ ID NO: 4 or 6, or fragments thereof (e.g., nucleotides 73-396). As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2× SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the nucleic acids as set forth in SEQ ID NO: 4 or 6 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects of the invention, the subject nucleic acid is provided in an expression vector comprising a nucleotide sequence encoding an ActRIIB polypeptide and operably linked to at least one regulatory sequence. Regulatory sequences are art-recognized and are selected to direct expression of the ActRIIB polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding an ActRIIB polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant ActRIIB polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject ActRIIB polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ActRIIB polypeptides in cells propagated in culture, e.g., to produce proteins, including fusion proteins or variant proteins, for purification.

This invention also pertains to a host cell transfected with a recombinant gene including a coding sequence (e.g., SEQ ID NO: 4 or 6) for one or more of the subject ActRIIB polypeptide. The host cell may be any prokaryotic or eukaryotic cell. For example, an ActRIIB polypeptide of the invention may be expressed in bacterial cells such as *E. coli*, insect cells (e.g., using a baculovirus expression system), yeast, or mammalian cells. Other suitable host cells are known to those skilled in the art.

Accordingly, the present invention further pertains to methods of producing the subject ActRIIB polypeptides. For example, a host cell transfected with an expression vector encoding an ActRIIB polypeptide can be cultured under appropriate conditions to allow expression of the ActRIIB polypeptide to occur. The ActRIIB polypeptide may be secreted and isolated from a mixture of cells and medium containing the ActRIIB polypeptide. Alternatively, the ActRIIB polypeptide may be retained cytoplasmically or in a membrane fraction and the cells harvested, lysed and the protein isolated. A cell culture includes host cells, media and other byproducts. Suitable media for cell culture are well known in the art. The subject ActRIIB polypeptides can be isolated from cell culture medium, host cells, or both, using techniques known in the art for purifying proteins, including ion-exchange chromatography, gel filtration chromatography, ultrafiltration, electrophoresis, and immunoaffinity purification with antibodies specific for particular epitopes of the ActRIIB polypeptides. In a preferred embodiment, the ActRIIB polypeptide is a fusion protein containing a domain which facilitates its purification.

In another embodiment, a fusion gene coding for a purification leader sequence, such as a poly-(His)/enterokinase cleavage site sequence at the N-terminus of the desired portion of the recombinant ActRIIB polypeptide, can allow purification of the expressed fusion protein by affinity chromatography using a $Ni^{2+}$ metal resin. The purification leader sequence can then be subsequently removed by treatment with enterokinase to provide the purified ActRIIB polypeptide (e.g., see Hochuli et al., (1987) *J. Chromatography* 411: 177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

5. Exemplary Therapeutic Uses

In certain embodiments, compositions (e.g., ActRIIB polypeptides) of the present invention can be used for treating or preventing a disease or condition that is associated with abnormal activity of an ActRIIB polypeptide and/or an ActRIIB ligand (e.g., GDF8). These diseases, disorders or conditions are generally referred to herein as "ActRIIB-associated conditions." In certain embodiments, the present invention provides methods of treating or preventing an individual in need thereof through administering to the individual a therapeutically effective amount of an ActRIIB polypeptide as described above. These methods are particularly aimed at therapeutic and prophylactic treatments of animals, and more particularly, humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes prophylaxis of the named condition or amelioration or elimination of the condition once it has been established.

ActRIIB/ActRIIB ligand complexes play essential roles in tissue growth as well as early developmental processes such as the correct formation of various structures or in one or more post-developmental capacities including sexual development, pituitary hormone production, and creation of bone and cartilage. Thus, ActRIIB-associated conditions include abnormal tissue growth and developmental defects. In addition, ActRIIB-associated conditions include, but are not limited to, disorders of cell growth and differentiation such as inflammation, allergy, autoimmune diseases, infectious diseases, and tumors.

Exemplary conditions for treatment include neuromuscular disorders (e.g., muscular dystrophy and muscle atrophy), congestive obstructive pulmonary disease (and muscle wasting associated with COPD), muscle wasting syndrome, sarcopenia, cachexia, adipose tissue disorders (e.g., obesity), type 2 diabetes, and bone degenerative disease (e.g., osteoporosis). Other exemplary conditions include musculodegenerative and neuromuscular disorders, tissue repair (e.g., wound healing), neurodegenerative diseases (e.g., amyotrophic lateral sclerosis), immunologic disorders (e.g., disorders related to abnormal proliferation or function of lymphocytes), and obesity or disorders related to abnormal proliferation of adipocytes.

In certain embodiments, compositions (e.g., ActRIIB-Fc polypeptides) of the invention are used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Exemplary muscular dystrophies that can be treated with a regimen including the subject ActRIIB polypeptides include: Duchenne Muscular Dystrophy (DMD), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (also known as Landouzy-Dejerine), Myotonic Dystrophy (MMD) (also known as Steinert's Disease), Oculopharyngeal Muscular Dystrophy (OPMD), Distal Muscular Dystrophy (DD), Congenital Muscular Dystrophy (CMD).

Duchenne Muscular Dystrophy (DMD) was first described by the French neurologist Guillaume Benjamin Amand Duchenne in the 1860s. Becker Muscular Dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is broken. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

BMD results from different mutations in the dystrophin gene. BMD patients have some dystrophin, but it is either insufficient in quantity or poor in quality. Having some dystrophin protects the muscles of those with BMD from degenerating as badly or as quickly as those of people with DMD.

For example, recent researches demonstrate that blocking or eliminating function of GDF8 (an ActRIIB ligand) in vivo can effectively treat at least certain symptoms in DMD and BMD patients. Thus, the subject ActRIIB polypeptides may act as GDF8 inhibitors (antagonists), and constitute an alternative means of blocking the functions of GDF8 and/or ActRIIB in vivo in DMD and BMD patients. This approach is confirmed and supported by the data shown herein, whereby an ActRIIB-Fc protein was shown to increase muscle mass in a mouse model of muscular dystrophy.

Similarly, the subject ActRIIB polypeptides provide an effective means to increase muscle mass in other disease conditions that are in need of muscle growth. For example, ALS, also called Lou Gehrig's disease (motor neuron disease) is a chronic, incurable, and unstoppable CNS disorder that attacks the motor neurons, components of the CNS that connect the brain to the skeletal muscles. In ALS, the motor neurons deteriorate and eventually die, and though a person's brain normally remains fully functioning and alert, the command to move never reaches the muscles. Most people who get ALS are between 40 and 70 years old. The first motor neurons that weaken are those leading to the arms or legs. Those with ALS may have trouble walking, they may drop things, fall, slur their speech, and laugh or cry uncontrollably. Eventually the muscles in the limbs begin to atrophy from disuse. This muscle weakness will become debilitating and a person will need a wheel chair or become unable to function out of bed. Most ALS patients die from respiratory failure or from complications of ventilator assistance like pneumonia, 3-5 years from disease onset. This approach is confirmed and supported by the data shown herein, whereby an ActRIIB-Fc protein was shown to improve the appearance, muscle mass and lifespan of a mouse model of ALS.

ActRIIB polypeptide-induced increased muscle mass might also benefit those suffering from muscle wasting diseases. Gonzalez-Cadavid et al. (supra) reported that GDF8 expression correlates inversely with fat-free mass in humans and that increased expression of the GDF8 gene is associated with weight loss in men with AIDS wasting syndrome. By inhibiting the function of GDF8 in AIDS patients, at least certain symptoms of AIDS may be alleviated, if not completely eliminated, thus significantly improving quality of life in AIDS patients.

Since loss of GDF8 (an ActRIIB ligand) function is also associated with fat loss without diminution of nutrient intake (Zimmers et al., supra; McPherron and Lee, supra), the subject ActRIIB polypeptides may further be used as a therapeutic agent for slowing or preventing the development of obesity and type II diabetes. This approach is confirmed and supported by the data shown herein, whereby an ActRIIB-Fc protein was shown to improve metabolic status in obese mice.

In certain embodiments, compositions (e.g., ActRIIB polypeptides) of the invention are used as part of a treatment for metabolic syndrome (also known as syndrome X and insulin resistance syndrome), which is a combination of disorders and risk factors that increase the risk of developing cardiovascular disease and diabetes mellitus type II. Most patients are older, obese, sedentary, and have some degree of insulin resistance. Central (abdominal or visceral) adiposity is a significant feature of the syndrome.

In related embodiments, ActRIIB polypeptides and other compositions of the invention can be used as part of a treatment for diabetes mellitus type II (also known as non-insulin-dependent diabetes mellitus or adult-onset diabetes), which is characterized by elevated blood glucose in the context of insulin resistance and relative insulin deficiency. Complex and multifactorial metabolic changes in diabetes often lead to damage and functional impairment of many organs, most importantly the cardiovascular system. Diabetes mellitus type II is often associated with obesity (abdominal or visceral adiposity), hypertension, elevated cholesterol, and metabolic syndrome Important risk factors for diabetes mellitus type II include aging, high-fat diets, and a sedentary lifestyle.

In other related embodiments, ActRIIB polypeptides and other compositions of the invention can be used as part of a treatment for atherosclerosis, a chronic inflammatory condition in which artery walls thicken due to the accumulation of fatty deposits, often referred to as plaques. Risk factors for atherosclerosis include aging, diabetes mellitus, dyslipoproteinemia, obesity (abdominal or visceral adiposity), and a sedentary lifestyle.

ActRIIB polypeptides can also be used for lipodystrophic disorders, which tend to be associated with metabolic syndrome. Severe insulin resistance can result from both genetic and acquired forms of lipodystrophy, including in the latter case human immunodeficiency virus (HIV)-related lipodystrophy in patients treated with antiretroviral therapy.

The cancer anorexia-cachexia syndrome is among the most debilitating and life-threatening aspects of cancer. Progressive weight loss in cancer anorexia-cachexia syndrome is a common feature of many types of cancer and is responsible not only for a poor quality of life and poor response to chemotherapy, but also a shorter survival time than is found in patients with comparable tumors without weight loss. Associated with anorexia, fat and muscle tissue wasting, psychological distress, and a lower quality of life, cachexia arises from a complex interaction between the cancer and the host. It is one of the most common causes of death among cancer patients and is present in 80% at death. It is a complex example of metabolic chaos effecting protein, carbohydrate, and fat metabolism. Tumors produce both direct and indirect abnormalities, resulting in anorexia and weight loss. Currently, there is no treatment to control or reverse the process. Cancer anorexia-cachexia syndrome affects cytokine production, release of lipid-mobilizing and proteolysis-inducing factors, and alterations in intermediary metabolism. Although anorexia is common, a decreased food intake alone is unable to account for the changes in body composition seen in cancer patients, and increasing nutrient intake is unable to reverse the wasting syndrome. Cachexia should be suspected in patients with cancer if an involuntary weight loss of greater than five percent of premorbid weight occurs within a six-month period.

Since systemic overexpression of GDF8 in adult mice was found to induce profound muscle and fat loss analogous to that seen in human cachexia syndromes (Zimmers et al., supra), the subject ActRIIB polypeptides as pharmaceutical compositions can be beneficially used to prevent, treat, or alleviate the symptoms of the cachexia syndrome, where muscle growth is desired.

In other embodiments, the present invention provides methods of inducing bone and/or cartilage formation, preventing bone loss, increasing bone mineralization or preventing the demineralization of bone. For example, the subject ActRIIB polypeptides and compounds identified in the present invention have application in treating osteoporosis and the healing of bone fractures and cartilage defects in humans and other animals. ActRIIB polypeptides may be useful in patients that are diagnosed with subclinical low bone density, as a protective measure against the development of osteoporosis.

In one specific embodiment, methods and compositions of the present invention may find medical utility in the healing of bone fractures and cartilage defects in humans and other animals. The subject methods and compositions may also have prophylactic use in closed as well as open fracture reduction and also in the improved fixation of artificial joints.

De novo bone formation induced by an osteogenic agent contributes to the repair of congenital, trauma-induced, or oncologic resection induced craniofacial defects, and also is useful in cosmetic plastic surgery. Further, methods and compositions of the invention may be used in the treatment of periodontal disease, and in other tooth repair processes. In certain cases, the subject ActRIIB polypeptides may provide an environment to attract bone-forming cells, stimulate growth of bone-forming cells or induce differentiation of progenitors of bone-forming cells. ActRIIB polypeptides of the invention may also be useful in the treatment of osteoporosis. Further, ActRIIB polypeptides may be used in cartilage defect repair and prevention/reversal of osteoarthritis.

In another specific embodiment, the invention provides a therapeutic method and composition for repairing fractures and other conditions related to cartilage and/or bone defects or periodontal diseases. The invention further provides therapeutic methods and compositions for wound healing and tissue repair. The types of wounds include, but are not limited to, burns, incisions and ulcers. See e.g., PCT Publication No. WO84/01106. Such compositions comprise a therapeutically effective amount of at least one of the ActRIIB polypeptides of the invention in admixture with a pharmaceutically acceptable vehicle, carrier or matrix.

In another specific embodiment, methods and compositions of the invention can be applied to conditions causing bone loss such as osteoporosis, hyperparathyroidism, Cushing's disease, thyrotoxicosis, chronic diarrheal state or malabsorption, renal tubular acidosis, chronic renal failure or anorexia nervosa. Many people know that being female, having a low body weight, and leading a sedentary lifestyle are risk factors for osteoporosis (loss of bone mineral density, leading to fracture risk). However, osteoporosis can also result from the long-term use of certain medications. Osteoporosis resulting from drugs or another medical condition is known as secondary osteoporosis. In a condition known as Cushing's disease, the excess amount of cortisol produced by the body results in osteoporosis and fractures. The most common medications associated with secondary osteoporosis are the corticosteroids, a class of drugs that act like cortisol, a hormone produced naturally by the adrenal glands. Although adequate levels of thyroid hormones (which are produced by the thyroid gland) are needed for the development of the skeleton, excess thyroid hormone can decrease bone mass over time. Antacids that contain aluminum can lead to bone loss when taken in high doses by people with kidney problems, particularly those undergoing dialysis. Other medications that can cause secondary osteoporosis include phenytoin (Dilantin) and barbiturates that are used to prevent seizures; methotrexate (Rheumatrex, Immunex, Folex PFS), a drug for some forms of arthritis, cancer, and immune disorders; cyclosporine (Sandimmune, Neoral), a drug used to treat some autoimmune diseases and to suppress the immune system in organ transplant patients; luteinizing hormone-releasing hormone agonists (Lupron, Zoladex), used to treat prostate cancer and endometriosis; heparin (Calciparine, Liquaemin), an anticlotting medication; and cholestyramine (Questran) and colestipol (Colestid), used to treat high cholesterol. Gum disease causes bone loss because these harmful bacteria in our mouths force our bodies to defend against them. The bacteria produce toxins and enzymes under the gum-line, causing a chronic infection.

In other embodiments, the present invention provides compositions and methods for regulating body fat content in an animal and for treating or preventing conditions related thereto, and particularly, health-compromising conditions related thereto. According to the present invention, to regulate (control) body weight can refer to reducing or increasing body weight, reducing or increasing the rate of weight gain, or increasing or reducing the rate of weight loss, and also includes actively maintaining, or not significantly changing body weight (e.g., against external or internal influences which may otherwise increase or decrease body weight). One embodiment of the present invention relates to regulating body weight by administering to an animal (e.g., a human) in need thereof an ActRIIB polypeptide.

In one specific embodiment, the present invention relates to methods and compounds for reducing fat mass and/or reducing gain of fat mass in an animal, and more particularly, for treating or ameliorating obesity in patients at risk for or suffering from obesity. In another specific embodiment, the present invention is directed to methods and compounds for treating an animal that is unable to gain or retain weight (e.g., an animal with a wasting syndrome). Such methods are effective to increase body weight and/or mass, or to reduce weight and/or mass loss, or to improve conditions associated with or caused by undesirably low (e.g., unhealthy) body weight and/or mass.

7. Pharmaceutical Compositions

In certain embodiments, compounds (e.g., ActRIIB polypeptides) of the present invention are formulated with a pharmaceutically acceptable carrier. For example, an ActRIIB polypeptide can be administered alone or as a component of a pharmaceutical formulation (therapeutic composition). The subject compounds may be formulated for administration in any convenient way for use in human or veterinary medicine.

In certain embodiments, the therapeutic method of the invention includes administering the composition topically, systemically, or locally as an implant or device. When administered, the therapeutic composition for use in this invention is, of course, in a pyrogen-free, physiologically acceptable form. Further, the composition may desirably be encapsulated or injected in a viscous form for delivery to a target tissue site (e.g., bone, cartilage, muscle, fat or neurons), for example, a site having a tissue damage. Topical administration may be suitable for wound healing and tissue repair. Therapeutically useful agents other than the ActRIIB polypeptides which may also optionally be included in the composition as described above, may alternatively or additionally, be administered simultaneously or sequentially with the subject compounds (e.g., ActRIIB polypeptides) in the methods of the invention.

In certain embodiments, compositions of the present invention may include a matrix capable of delivering one or more therapeutic compounds (e.g., ActRIIB polypeptides) to a target tissue site, providing a structure for the developing tissue and optimally capable of being resorbed into the body. For example, the matrix may provide slow release of the ActRIIB polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Certain compositions disclosed herein may be administered topically, either to skin or to mucosal membranes. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to a subject compound of the invention (e.g., an ActRIIB polypeptide), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject compound, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

In certain embodiments, pharmaceutical compositions suitable for parenteral administration may comprise one or more ActRIIB polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., ActRIIB polypeptides). The various factors will depend upon the disease to be treated.

In certain embodiments, the present invention also provides gene therapy for the in vivo production of ActRIIB polypeptides or other compounds disclosed herein. Such therapy would achieve its therapeutic effect by introduction of the ActRIIB polynucleotide sequences into cells or tissues having the disorders as listed above. Delivery of ActRIIB polynucleotide sequences can be achieved using a recombinant expression vector such as a chimeric virus or a colloidal dispersion system. Preferred for therapeutic delivery of ActRIIB polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the ActRIIB polynucleotide. In one preferred embodiment, the vector is targeted to bone, cartilage, muscle or neuron cells/tissues.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for ActRIIB polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1

Generation of ActRIIB(25-131)-hFc with Alternative Nucleotide Sequences

To generate ActRIIB(25-131)-hFc, the human ActRIIB extracellular domain with N-terminal and C-terminal truncations (residues 25-131 of the native protein) was fused N-terminally with a TPA leader sequence substituted for the native ActRIIB leader and C-terminally with a human Fc domain via a minimal linker (three glycine residues) (FIG. 1). A nucleotide sequence encoding this fusion protein is shown in FIG. 2. Applicants modified the codons and found a variant nucleic acid encoding the ActRIIB(25-131)-hFc protein that provided substantial improvement in the expression levels of initial transformants (FIG. 3).

The mature protein has an amino acid sequence as follows (N-terminus confirmed by N-terminal sequencing) (SEQ ID NO: 8):

```
ETRECIYYNA NWELERTNQS GLERCEGEQD KRLHCYASWR

NSSGTIELVK KGCWLDDFNC YDRQECVATE ENPQVYFCCC

EGNFCNERFT HLPEAGGPEV TYEPPPTGGG THTCPPCPAP

ELLGGPSVFL FPPKPKDTLM ISRTPEVTCV VVDVSHEDPE

VKFNWYVDGV EVHNAKTKPR EEQYNSTYRV VSVLTVLHQD

WLNGKEYKCK VSNKALPAPI EKTISKAKGQ PREPQVYTLP

PSREEMTKNQ VSLTCLVKGF YPSDIAVEWE SNGQPENNYK

TTPPVLDSDG SFFLYSKLTV DKSRWQQGNV FSCSVMHEAL

HNHYTQKSLS LSPGK
```

Amino acids 1-107 are derived from ActRIIB.

The expressed molecule was purified using a series of column chromatography steps, including for example, three or more of the following, in any order: Protein A chromatography, Q sepharose chromatography, phenylsepharose chromatography, size exclusion chromatography and cation exchange chromatography. The purification could be completed with viral filtration and buffer exchange.

Example 2

High-Affinity Ligand Binding by ActRIIB(25-131)-hFc

Affinities of several ligands for ActRIIB(25-131)-hFc and its full-length counterpart ActRIIB(20-134)-hFc were evaluated in vitro with a Biacore™ instrument, and the results are summarized in the table below. Kd values were obtained by steady-state affinity fit due to very rapid association and dissociation of the complex, which prevented accurate determination of $k_{on}$ and $k_{off}$. ActRIIB(25-131)-hFc bound activin A, activin B, and GDF11 with high affinity. Intriguingly, ActRIIB(25-131)-hFc appears to show a higher affinity for GDF3 than ActRIIB(20-134)-hFc (data not shown).

Ligand Affinities of ActRIIB-hFc Forms:

| Fusion Construct | Activin A (e-11) | Activin B (e-11) | GDF11 (e-11) |
|---|---|---|---|
| ActRIIB(20-134)-hFc | 1.6 | 1.2 | 3.6 |
| ActRIIB(25-131)-hFc | 1.8 | 1.2 | 3.1 |

Example 3

ActRIIB(25-131)-hFc Increases Muscle Mass and Strength In Vivo

Figure 5:
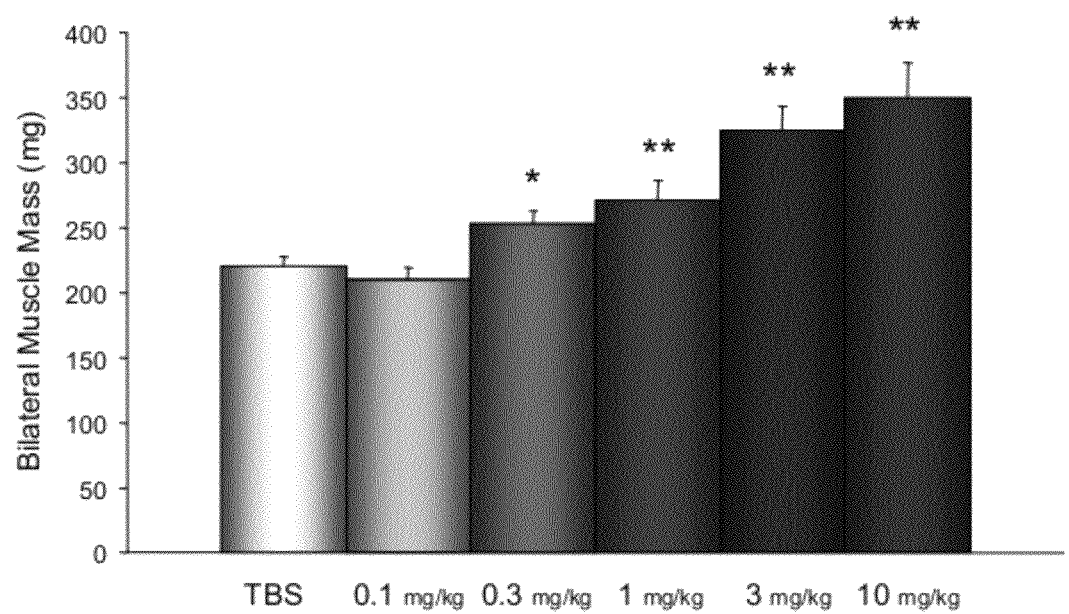
FIG. 5 shows the effect of four weeks treatment with ActRIIB(25-131)-hFc on pectoralis muscle mass in mouse. Vehicle was Tris-buffered saline (TBS). Data are means (n=10 per group)±SEM. *, P<0.05; **, P<0.01 vs. TBS by unpaired t-test. ActRIIB(25-131)-hFc treatment increased pectoralis muscle mass in a clear dose-dependent manner.
Figure 6:
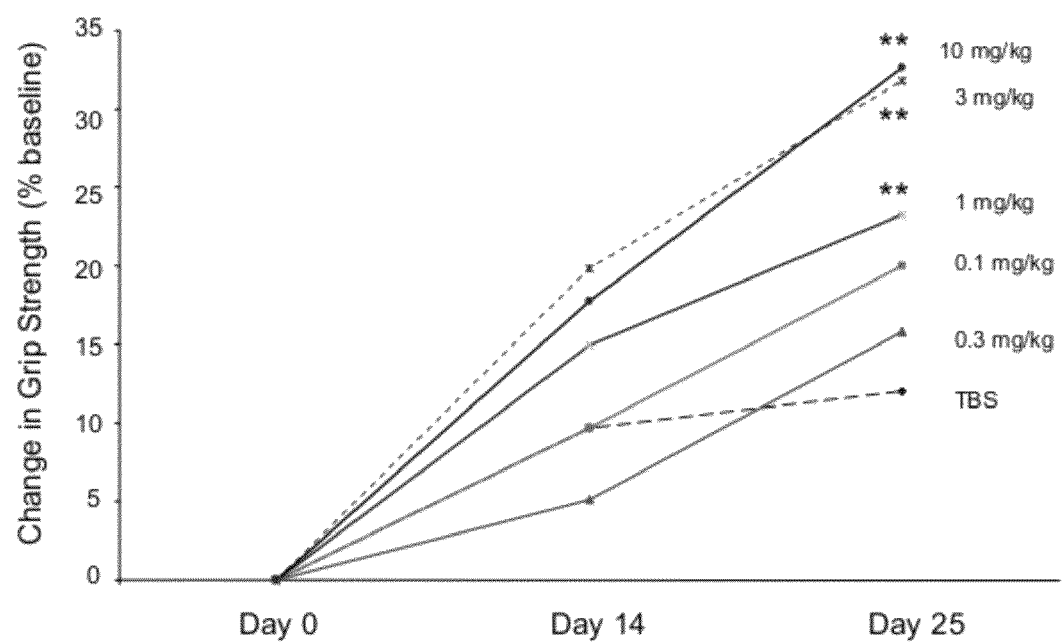
FIG. 6 shows the effect of ActRIIB(25-131)-hFc treatment on grip strength in mouse. Vehicle was Tris-buffered saline (TBS). Data are means (n=10 per group). **, P<0.01 vs. TBS by unpaired t-test. ActRIIB(25-131)-hFc treatment increased grip strength in a dose-dependent manner.

Applicants investigated the ability of ActRIIB(25-131)-hFc to increase muscle mass and strength in the mouse. Male mice (n=10 per group) were treated subcutaneously twice per week with vehicle (Tris-buffered saline) or one of five doses of ActRIIB(25-131)-hFc. Four weeks of treatment with ActRIIB(25-131)-hFc produced a clear dose-dependent increase in lean tissue mass (FIG. 4), as determined by whole-body nuclear magnetic resonance (NMR) scanning Increased muscle mass was confirmed at study termination for specific muscles, including the pectoralis (FIG. 5), rectus femoris, and gastrocnemius. Importantly, increased muscle mass was accompanied by increased strength, as assessed by grip strength, compared to vehicle (FIG. 6). These results provide compelling evidence that ActRIIB(25-131)-hFc increases both muscle mass and muscle strength in vivo.

Example 4

ActRIIB(25-131)-hFc Prevents Muscle Loss in Mouse Model of Androgen Deprivation

Figure 7:
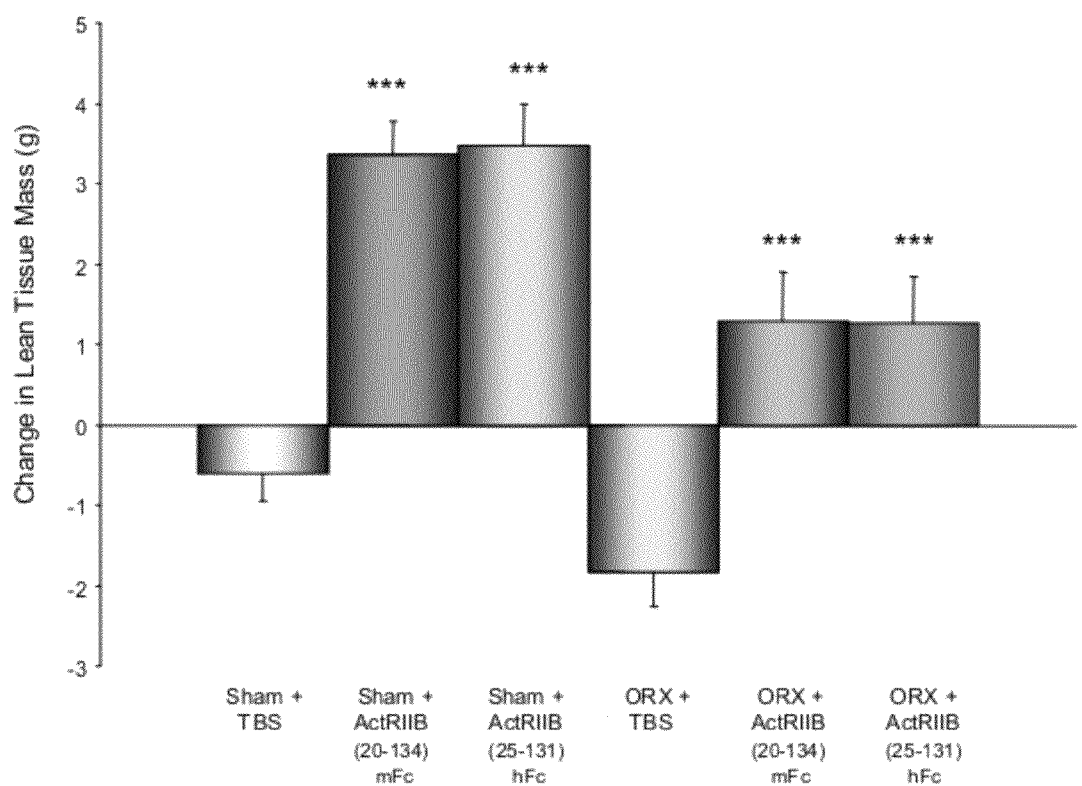
FIG. 7 shows the effect of four weeks treatment with ActRIIB(25-131)-hFc on lean tissue mass in a mouse model of androgen deprivation. Vehicle was Tris-buffered saline (TBS). Data for orchidectomized (ORX) or sham-operated mice are means (n=10 per group)±SD. ***, P<0.001 vs. TBS control. ActRIIB(25-131)-hFc increased lean tissue mass as effectively as did its full-length counterpart ActRIIB(20-134)-mFc.

Applicants investigated the ability of ActRIIB(25-131)-hFc to prevent muscle loss in a mouse model of androgen deprivation, a standard therapeutic intervention for advanced prostate cancer in men. Male mice (n=10 per group) were orchidectomized (ORX) or sham-operated and treated subcutaneously twice per week with TBS vehicle, ActRIIB(25-131)-hFc at 10 mg/kg, or its full-length murine counterpart ActRIIB(20-134)-mFc at 10 mg/kg. Lean tissue mass was determined by whole-body NMR scan. ORX mice treated for four weeks with either of the ActRIIB-Fc forms displayed an increase in lean tissue mass from baseline, which was highly significant compared to the decrease observed in ORX controls over that period (FIG. 7). An analogous, highly significant increase was observed under gonad-intact conditions for both ActRIIB-Fc forms compared to sham controls (FIG. 7). These results demonstrate that ActRIIB(25-131)-hFc can increase lean tissue mass (prevent muscle loss) as effectively as its full-length counterpart ActRIIB(20-134)-mFc in this androgen deprivation model.

Example 5

Figure 8:
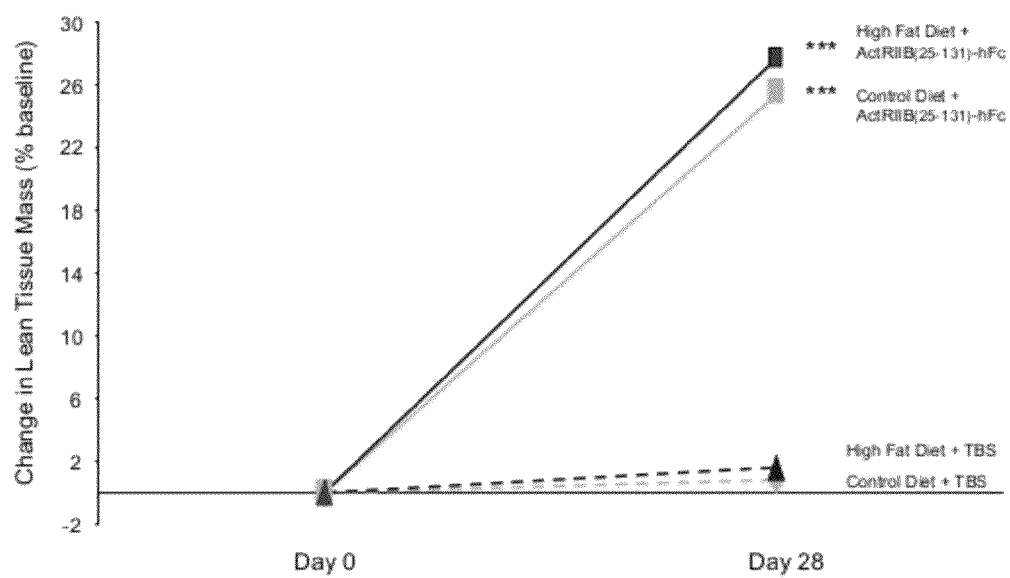
FIG. 8 shows the effect of ActRIIB(25-131)-hFc on lean tissue mass in a mouse model of diet-induced obesity. Vehicle was Tris-buffered saline (TBS). Data are means (n=9-10 per group). ***, P<0.001 vs. TBS control. ActRIIB(25-131)-hFc increased lean tissue mass effectively in mice fed a high fat diet.
Figure 9:
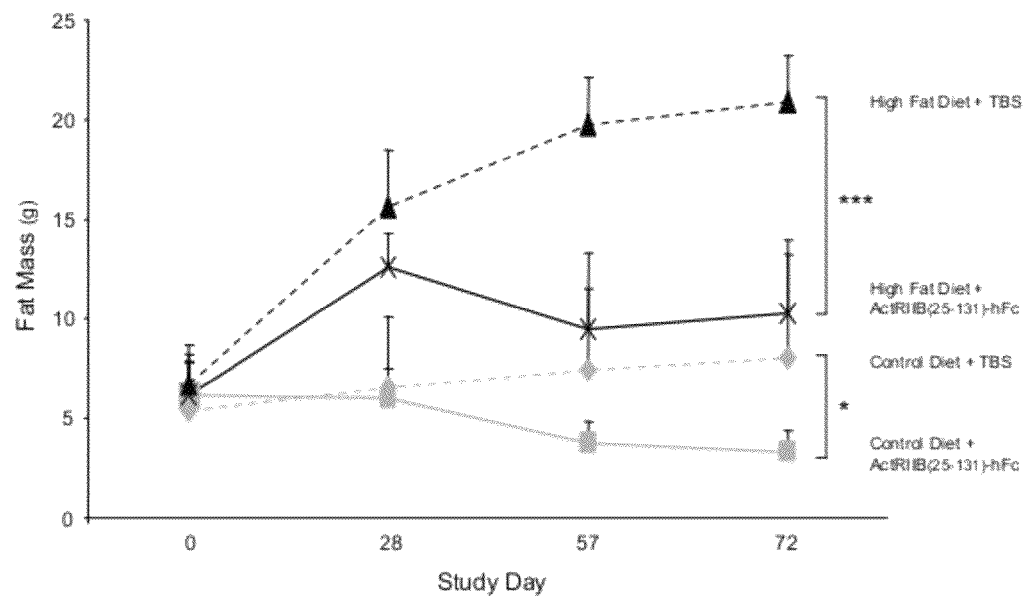
FIG. 9 shows the effect of ActRIIB(25-131)-hFc on fat mass in a mouse model of diet-induced obesity. Vehicle was Tris-buffered saline (TBS). Data are means (n=9-10 per group)±SD. *, P<0.05; ***, P<0.001 vs. TBS control. Compared to vehicle, ActRIIB(25-131)-hFc treatment for 12 weeks reduced fat mass by approximately half in mice fed a high fat diet.
Figure 10:
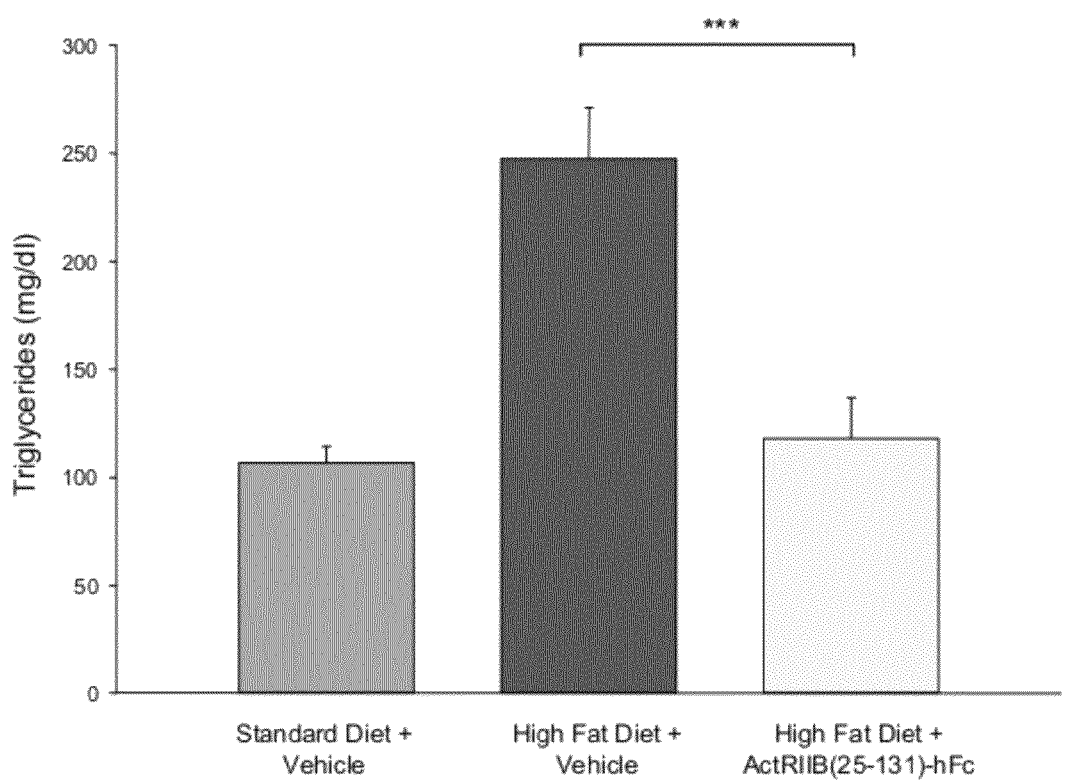
FIG. 10 depicts serum triglyceride concentrations in mice as a function of diet and ActRIIB(25-131)-hFc treatment for 60 days. Data are means±SEM. ***, P<0.001. In mice fed a high-fat diet, ActRIIB(25-131)-hFc reduced triglyceride concentrations by more than 50%, thereby normalizing triglycerides to levels observed in standard-diet controls.
Figure 11:
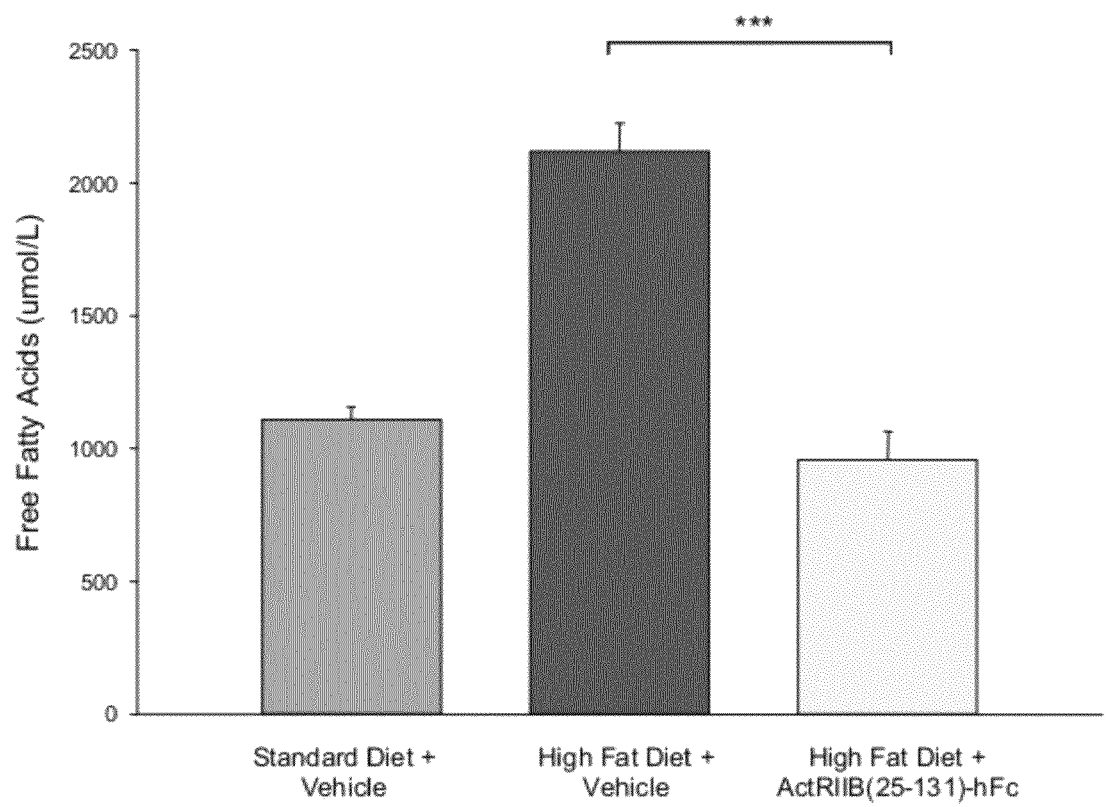
FIG. 11 depicts serum free fatty acid (FFA) concentrations in mice as a function of diet and ActRIIB(25-131)-hFc treatment for 60 days. Data are means±SEM. ***, P<0.001. In mice fed a high-fat diet, ActRIIB(25-131)-hFc reduced FFA concentrations by nearly 55%, thereby normalizing FFA to levels observed in standard-diet controls.
Figure 12:
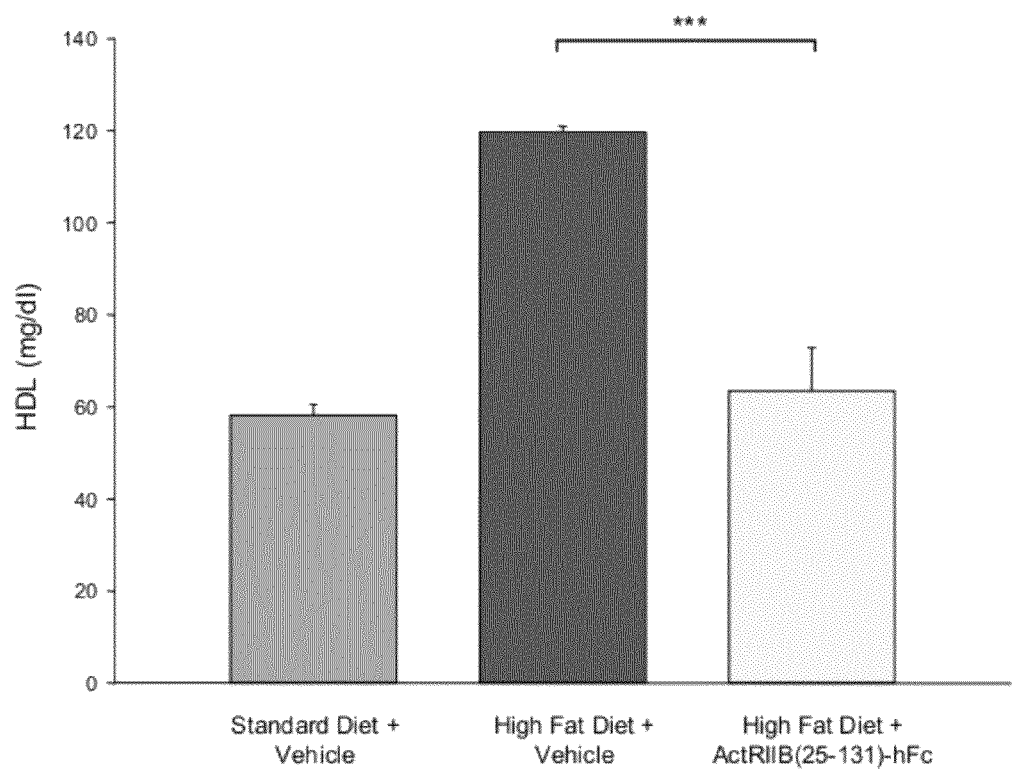
FIG. 12 depicts serum high-density lipoprotein (HDL) concentrations in mice as a function of diet and ActRIIB(25-131)-hFc treatment for 60 days. Data are means±SEM. ***, P<0.001. In mice fed a high-fat diet, ActRIIB(25-131)-hFc reduced HDL concentrations by nearly 50%, thereby normalizing HDL to levels observed in standard-diet controls.
Figure 13:
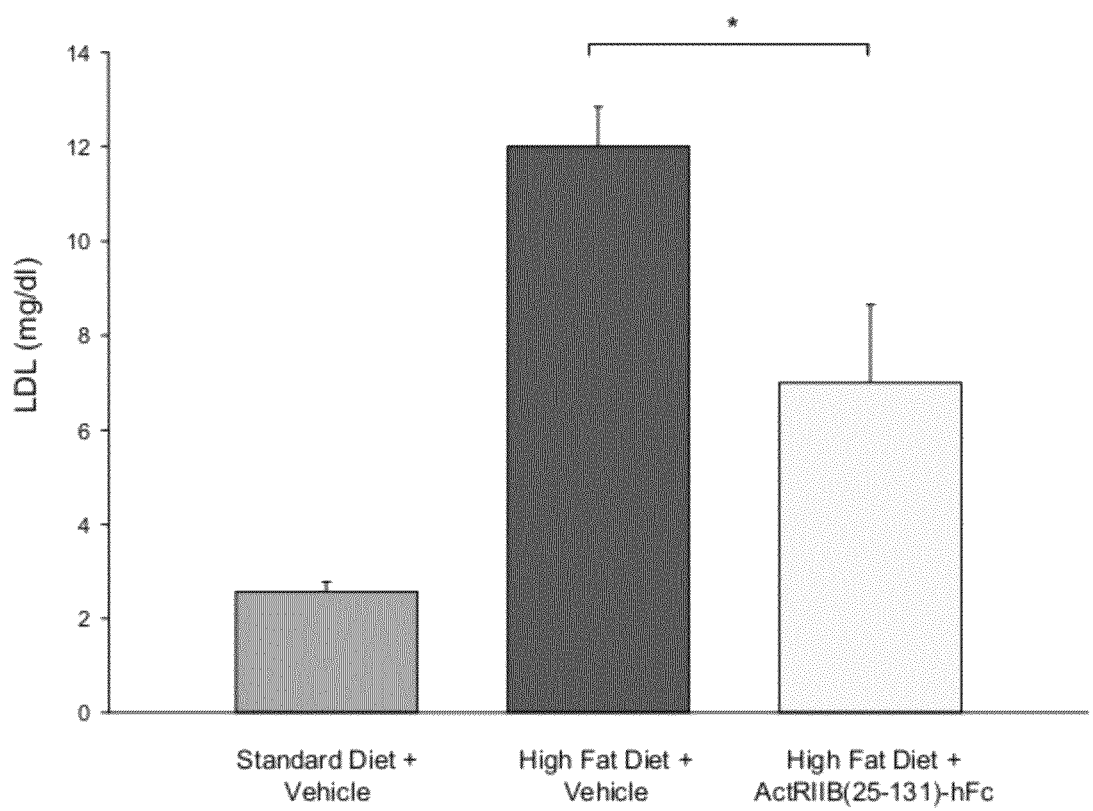
FIG. 13 depicts serum low-density lipoprotein (LDL) concentrations in mice as a function of diet and ActRIIB(25-131)-hFc treatment for 60 days. Data are means±SEM. *, P<0.05. In mice fed a high-fat diet, ActRIIB(25-131)-hFc reduced LDL concentrations by more than 40%.

ActRIIB(25-131)-hFc Improves Body Composition in Mouse Model of Diet-Induced Obesity Applicants also investigated the ability of ActRIIB(25-131)-hFc to increase muscle mass and reduce fat mass in a mouse model of diet-induced obesity. Male mice (n=10 per group) were fed either a standard chow diet or a high fat diet and treated intraperitoneally twice per week with TBS vehicle or ActRIIB(25-131)-hFc at 10 mg/kg. Lean tissue mass and fat mass were determined by whole-body NMR scan. Treatment of mice on the high fat diet with ActRIIB(25-131)-hFc for four weeks resulted in more than a 25% increase in lean tissue mass as compared to a 2% increase with vehicle treatment (FIG. 8). Similar results were obtained in mice on the control diet with ActRIIB(25-131)-hFc as compared to vehicle (FIG. 8). Moreover, continued treatment was found to improve adiposity. Compared to vehicle, ActRIIB(25-131)-hFc treatment for 12 weeks reduced fat mass by approximately half in mice on the high fat diet as well as in those on the control diet (FIG. 9).

Taken together, these data demonstrate that ActRIIB(25-131)-hFc can be used to improve body composition in vivo under a variety of conditions, including androgen deprivation and high fat intake.

Example 6

ActRIIB(25-131)-hFc Normalizes Serum Lipids, Insulin, and Adiponectin in Mouse Model of Diet-Induced Obesity Applicants investigated the effects of ActRIIB(25-131)-hFc on serum concentrations of clinically important lipids, insulin, adiponectin, and on other metabolic endpoints in male mice fed a high-fat diet. Ten-week-old C57BL/6 mice were weight-matched and treated with ActRIIB(25-131)-hFc (n=10) or Tris-buffered-saline (TBS) vehicle (n=7) twice per week at 10 mg/kg, s.c., for 60 days. During this period, mice had unlimited access to a diet containing 58% fat instead of the standard chow containing 4.5% fat.

Figure 14:
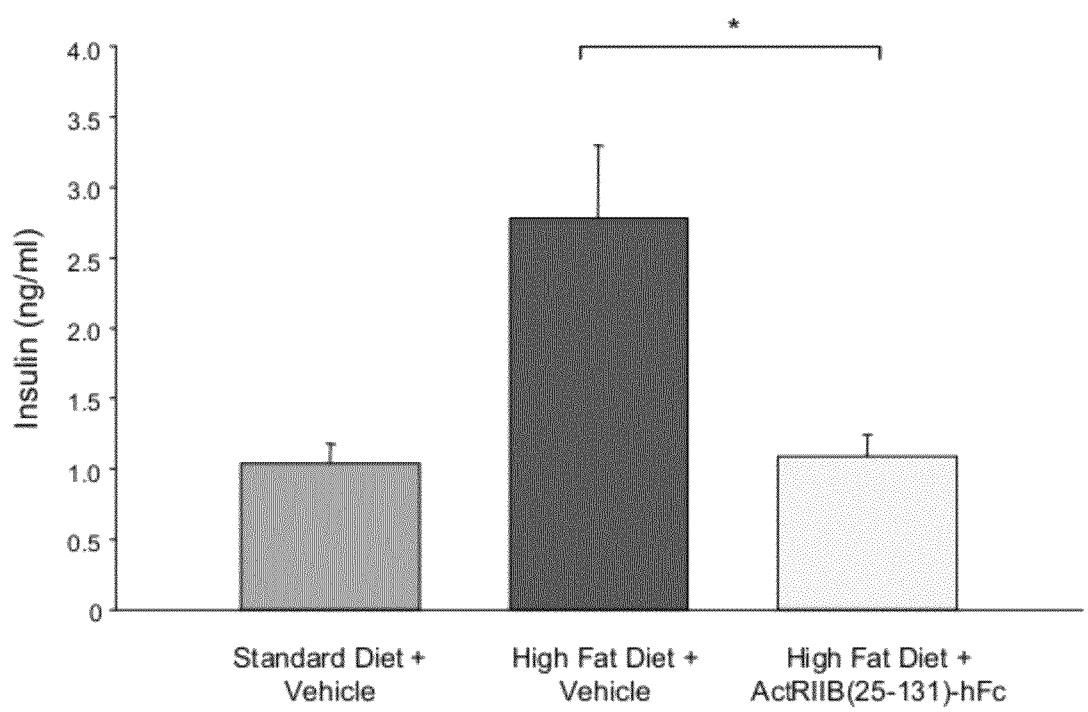
FIG. 14 depicts serum insulin concentrations in mice as a function of diet and ActRIIB(25-131)-hFc treatment for 60 days. Data are means±SEM. **, P<0.01. In mice fed a high-fat diet, ActRIIB(25-131)-hFc reduced insulin concentrations by more than 60%, thereby normalizing insulin to levels observed in standard-diet controls.
Figure 15:
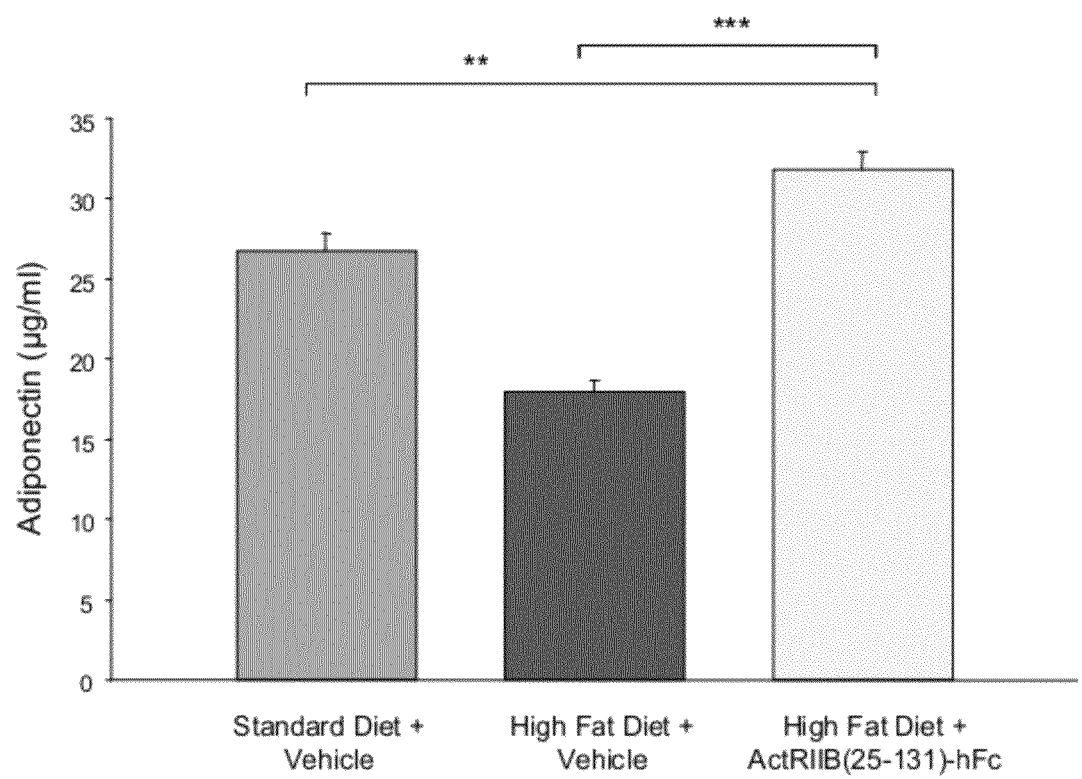
FIG. 15 depicts serum adiponectin concentrations in mice as a function of diet and ActRIIB(25-131)-hFc treatment for 60 days. ELISA measurements detect all main oligomeric isoforms (total adiponectin), and data are means±SEM. , P<0.01; *, P<0.001. In mice fed a high-fat diet, ActRIIB (25-131)-hFc increased adiponectin concentrations by more than 75% and even boosted adiponectin significantly above the levels observed in standard-diet controls.

ActRIIB(25-131)-hFc treatment caused a constellation of noteworthy metabolic effects. In mice fed a high-fat diet, ActRIIB(25-131)-hFc reduced the pathologically elevated serum concentrations of triglycerides, free fatty acids, high-density lipoprotein (HDL), and low-density lipoprotein (LDL) (FIG. 10-13), in most cases normalizing these parameters to levels observed in mice fed a standard diet. Importantly, ActRIIB(25-131)-hFc treatment also normalized insulin concentrations in high-fat-diet mice (FIG. 14) and increased concentrations of adiponectin significantly above even those in mice fed a standard diet (FIG. 15). Adiponectin is a key biomarker of body composition, as circulating adiponectin levels are known to vary inversely with fat mass/obesity, and adiponectin enhances insulin sensitivity in target tissues. ActRIIB(25-131)-hFc also reduced serum concentrations of leptin, another major indicator of adipocyte status, by nearly 50% ($P<0.05$). Finally, the aforementioned effects were accompanied by beneficial changes in body composition, as determined by nuclear magnetic resonance (NMR) at baseline and Day 48. Under high-fat dietary conditions, total fat mass in vehicle-treated controls tripled during this 48-day period, and ActRIIB(25-131)-hFc treatment cut this increase by nearly 40%. By Day 48, total fat mass was 27% of body weight in ActRIIB-Fc-treated mice vs. 39% in control mice, whereas lean tissue mass was 59% of body weight in ActRIIB(25-131)-hFc-treated mice vs. 55% in control mice. Thus, the net result was a healthier body composition under conditions of high-fat diet.

For the foregoing serum parameters, ActRIIB(25-131)-hFc consistently outperformed ActRIIB(20-134)-hFc, which was also evaluated in this same study. Thus, ActRIIB(25-131)-hFc improved triglyceride levels nearly 6 times as much, FFA levels nearly twice as much, HDL levels nearly 4 times as much, insulin levels more than twice as much, and adiponectin levels nearly 1.5 times as much as ActRIIB(20-134)-hFc did at the same dose.

Example 7

Figure 16:
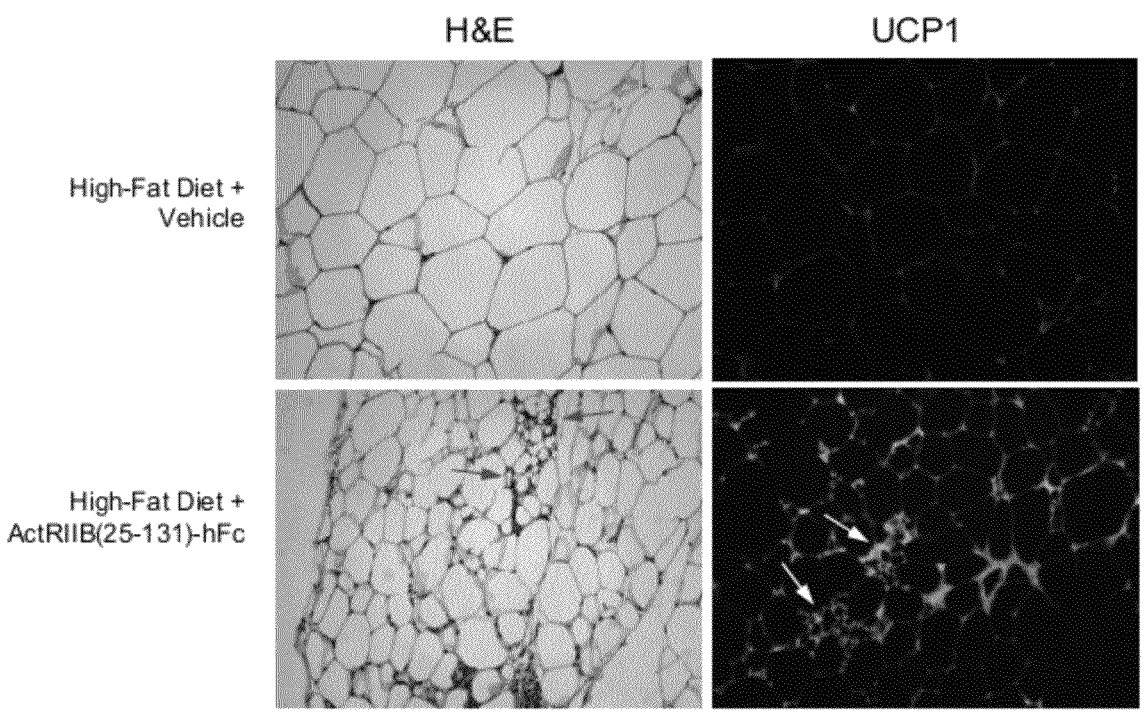
FIG. 16 shows thermogenic histological changes induced within epididymal white adipose tissue by ActRIIB(25-131)-hFc treatment for 60 days in a mouse model of diet-induced obesity. All microscopic images shown at the same magnification. Hematoxylin and eosin (H&E) staining indicates the ability of ActRIIB(25-131)-hFc to reduce lipid droplet size and induce clusters of multilocular adipocytes (arrows) characteristic of brown fat. Immunostaining of non-adjacent sections reveals widespread cytoplasmic induction of UCP1 (green fluorescence) in both multilocular and unilocular adipocytes.

ActRIIB(25-131)-hFc Induces Thermogenic Properties in White Fat in Mouse Model of Diet-Induced Obesity In the study described above (Example 6), Applicants also investigated effects of ActRIIB(25-131)-hFc on thermogenic properties of white adipose tissue. Under high-fat dietary conditions, ActRIIB(25-131)-hFc treatment triggered histological changes and a gene expression profile in white adipose tissue that were consistent with thermogenic capability. As shown in FIG. 16, histological examination of epididymal white fat indicated that ActRIIB(25-131)-hFc reduced lipid droplet size and caused formation of clusters of multilocular adipocytes that are a hallmark of brown fat. Moreover, immunohistochemical analysis of this tissue revealed widespread cytoplasmic induction of UCP1 in both multilocular and unilocular adipocytes as a result of ActRIIB(25-131)-hFc treatment (FIG. 16).

Figure 17:
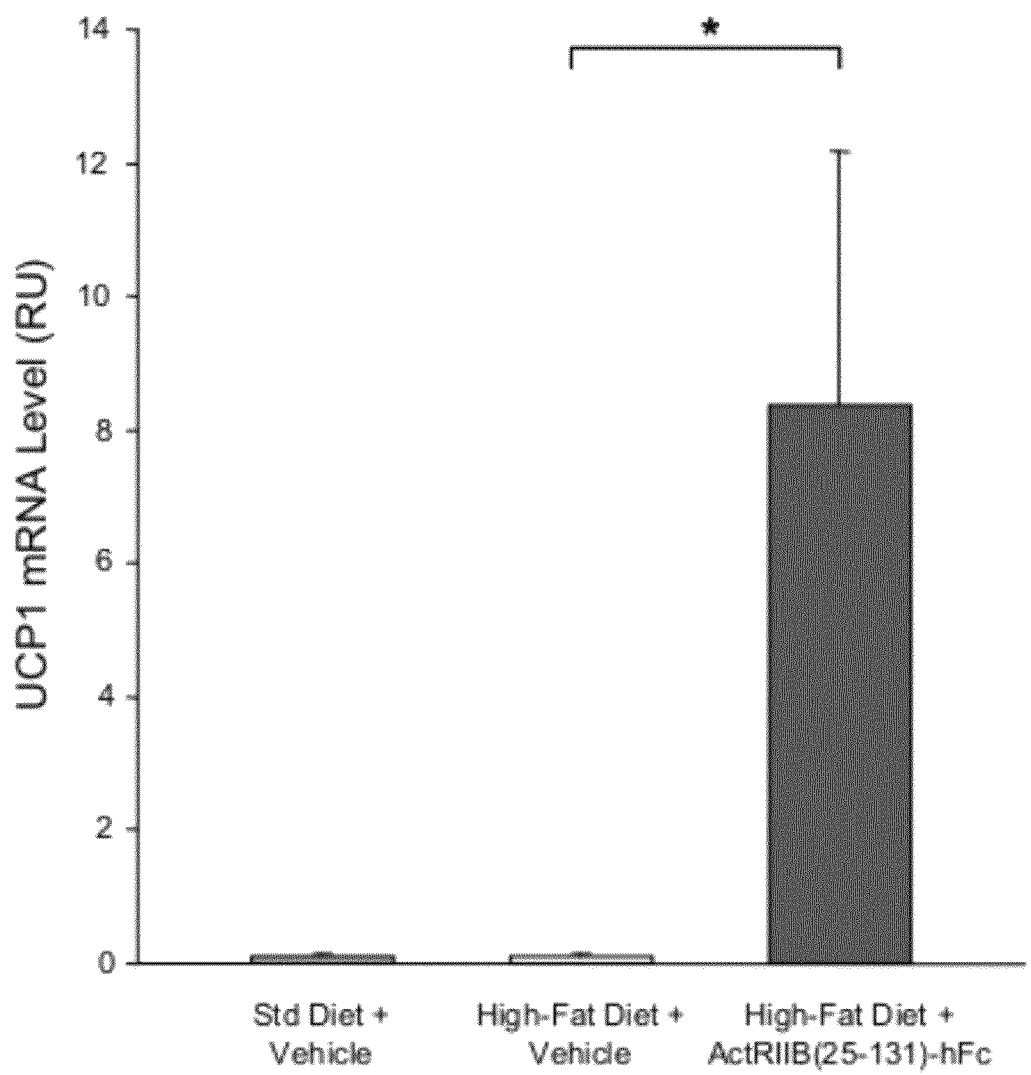
FIG. 17 shows the effect of ActRIIB(25-131)-hFc treatment for 60 days on UCP1 mRNA levels in epididymal white fat in a mouse model of diet-induced obesity. Data obtained by reverse transcriptase polymerase chain reaction (RT-PCR), in relative units (RU), are means±SEM; n=6-7 per group; *, p<0.05. ActRIIB(25-131)-hFc caused a 60-fold increase in mRNA encoding this selective marker for brown fat, thus indicating upregulation of thermogenic capability within this white fat depot.

Accompanying these histological changes were significant changes in the expression of key thermogenic and metabolic regulatory genes in epididymal white fat, as determined by quantitative RT-PCR (reverse transcription polymerase chain reaction). In mice on the high-fat diet, ActRIIB(25-131)-hFc treatment increased UCP1 mRNA levels more than 60-fold compared to vehicle (FIG. 17), a particularly impressive change since this strain of mouse displays severely blunted induction of UCP1 and brown adipocytes within key white fat depots compared to other mouse strains (Guerra et al., 1998, J Clin Invest 102:412-420; Xue et al., 2007, J Lipid Res 48:41-51). In addition, ActRIIB(25-131)-hFc treatment increased levels of mRNA encoding the sirtuin SIRT-1 (silent information regulator two, homolog 1), an energy-sensitive master regulator (deacetylase) that protects against metabolic damage induced by a high-fat diet (Pfluger et al., 2008, Proc Natl Acad Sci USA 105:9793-9798) and is implicated as an important control of fatty acid mobilization (Rodgers et al., 2008, FEBS Lett 582:46-53). Significantly, ActRIIB(25-131)-hFc treatment also increased levels of mRNA encoding PGC-1α (peroxisome proliferator-activated receptor gamma coactivator-1α), a well-documented target of SIRT-1 that, in turn, controls expression of many genes necessary for mitochondrial biogenesis and thermogenic capability in brown adipose tissue (Uldry et al., 2006, Cell Metab, 3:333-341). Notably, forced expression of PGC-1α in white adipocytes has been shown to induce a thermogenic program of gene expression, including UCP1, closely resembling that in brown adipocytes (Hansen et al., 2006, Biochem J 398:153-168). In the present study, ActRIIB(25-131)-hFc restored PGC-1α gene expression in white adipose tissue under high-fat dietary conditions to levels indistinguishable from those in mice fed the standard diet.

Figure 18:
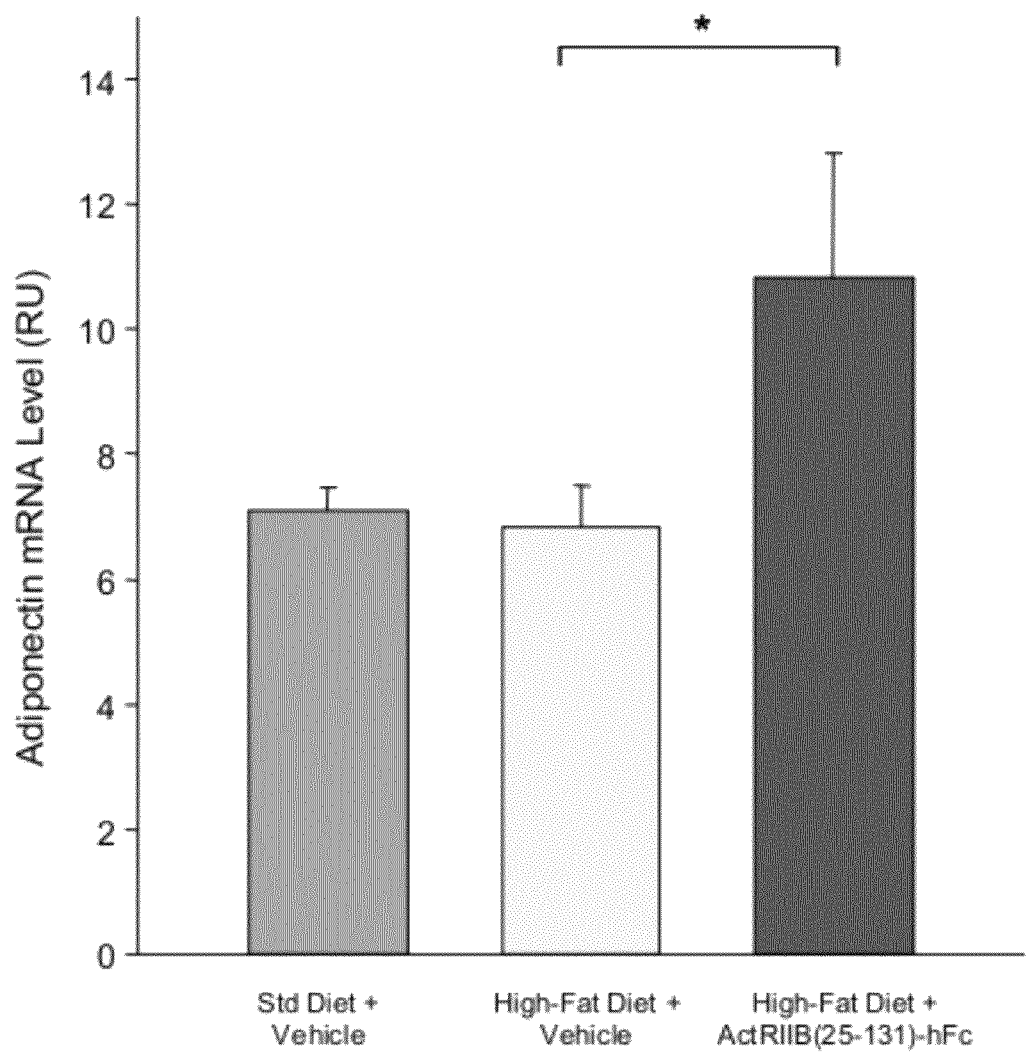
FIG. 18 shows levels of adiponectin mRNA in epididymal white fat of mice as a function of diet and ActRIIB(25-131)-hFc treatment for 60 days. RT-PCR data, in relative units (RU), are means±SEM; n=7 per group; *, p<0.05. In mice fed a high-fat diet, ActRIIB(25-131)-hFc increased adiponectin mRNA levels by more than 60%, thus contributing to elevated concentrations of circulating adiponectin in these mice.

Additional changes associated with treatment constitute a prominent link between the altered expression profile in white adipose tissue and beneficial hormonal and metabolic effects. Thus, in epididymal white fat, ActRIIB(25-131)-hFc increased levels of mRNA encoding Foxo-1 (forkhead box-containing, protein O subfamily-1), a transcription factor that is both a target of SIRT-1 and a key inducer of adiponectin expression (Qiao et al., 2006, J Biol Chem 281:39915-39924). Consistent with Foxo-1 mRNA induction, ActRIIB(25-131)-hFc treatment raised levels of adiponectin mRNA in white fat (FIG. 18), which helps to account for increased circulating levels of adiponectin (FIG. 15, Example 6), enhanced insulin sensitivity in target tissues, and normalized insulin concentrations (FIG. 14, Example 6) in these animals. In summary, ActRIIB(25-131)-hFc treatment under high-fat dietary conditions resulted in 1) histological changes and a gene expression profile in white adipose tissue that were consistent with thermogenic capability and 2) beneficial changes in a wide range of hormonal and metabolic parameters.

Example 8

Figure 19:
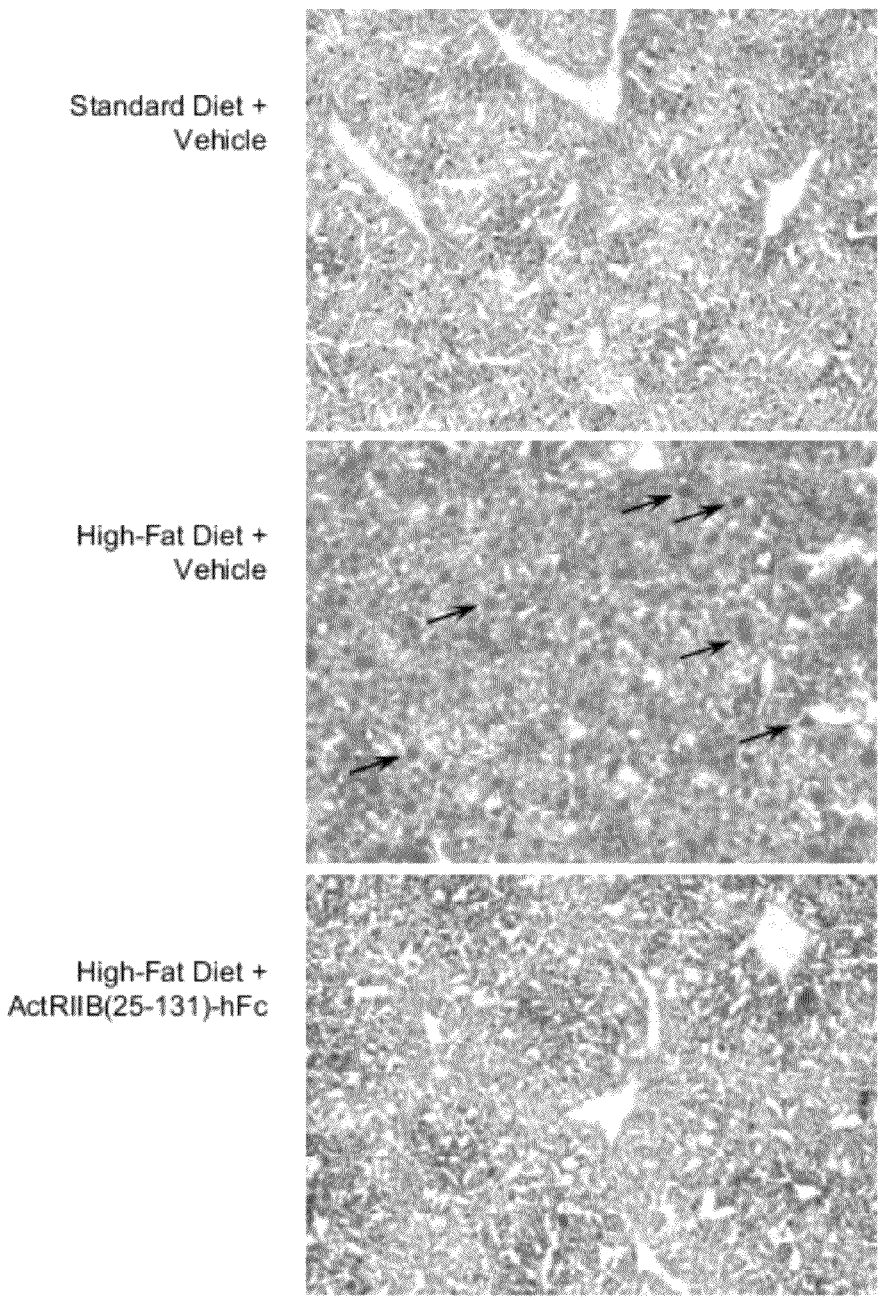
FIG. 19 shows the effect of ActRIIB(25-131)-hFc treatment for 60 days on fatty liver deposits (hepatic steatosis) in a mouse model of diet-induced obesity. Liver sections (all shown at the same magnification) stained with Oil Red O reveal pronounced lipid deposition under high-fat dietary conditions but not control conditions. Arrows indicate several of many densely packed lipid droplets, which are stained bright red but difficult to discern in black-and-white images. ActRIIB(25-131)-hFc inhibited formation of such lipid droplets and largely restored the appearance of liver tissue to that of mice fed the standard diet.

Effects of ActRIIB(25-131)-hFc on Liver and Muscle in Mouse Model of Diet-Induced Obesity Nonalcoholic fatty liver disease (NAFLD) is a spectrum of increasingly common hepatic disorders widely considered to be the hepatic manifestation of metabolic syndrome and characterized by fat accumulation in the liver (steatosis), often with deleterious effects. A subset of NAFLD patients develop an inflammatory condition referred to as nonalcoholic steatohepatitis (NASH), which can progress further to hepatic fibrosis, cirrhosis, and hepatocellular carcinoma (Perlemuter et al., 2007, Nat Clin Pract Endocrinol Metab 3:458-469). In the study described above (Examples 6-7), Applicants investigated whether ActRIIB(25-131)-hFc could inhibit hepatic steatosis associated with a high-fat diet. At study completion, hepatic tissue of mice fed the high-fat diet displayed large numbers of densely packed lipid droplets, as assessed by staining with Oil Red O, whereas mice fed the standard diet showed no evidence of hepatic lipid deposits (FIG. 19). Treatment with ActRIIB(25-131)-hFc almost completely reversed hepatic lipid deposition and normalized the appearance of hepatic tissue despite the high-fat diet. Thus, ActRIIB(25-131)-hFc was an effective inhibitor of hepatic steatosis caused by high-fat diet.

ActRIIB(25-131)-hFc treatment also increased muscle mass in this model of diet-induced obesity, consistent with findings in other models (Examples 3-5). Specifically, ActRIIB(25-131)-hFc increased pectoralis mass by more than 70% (P<0.001), gastrocnemius mass by nearly 40% (P<0.001), and rectus femoris mass by more than 25% (P<0.001) compared to high-fat diet controls. These changes in muscle mass were accompanied by changes in muscle gene expression, as determined in gastrocnemius tissue by RT-PCR. Compared to high-fat diet controls, ActRIIB(25-131)-hFc increased PGC-1α mRNA levels and Foxo-1 mRNA levels by approximately 50% each (P<0.05) in gastrocnemius.

Example 9

Effect of ActRIIB(25-131)-mFc on Visceral White Fat in Mouse Model of Diet-Induced Obesity Accumulation of visceral fat, as opposed to subcutaneous fat, plays a critical role in the development of cardiovascular disease and obesity-related disorders such as diabetes mellitus, hyperlipidemia, hypertension, and metabolic syndrome (Matsuzawa et al., 2006, FEBS Lett 580:2917-2921). Due to its location, visceral (or intra-abdominal) fat has ready access to the liver via the hepatic portal circulation, where it could influence metabolism, promote insulin resistance, and cause steatosis. Therefore, in a study similar to that described above (Examples 6-8), Applicants investigated effects of the truncated variant ActRIIB(25-131)-mFc on the quantities of visceral fat vs. abdominal subcutaneous fat under high-fat dietary conditions. Nine-week-old C57BL/6 mice were treated with ActRIIB(25-131)-mFc (n=20), at 10 mg/kg, s.c., or Tris-buffered-saline (TBS) vehicle (n=10) twice per week for 60 days. Beginning 7 days before the start of dosing, mice had unlimited access to a diet containing 58% fat instead of the standard chow containing 4.5% fat. An additional group of mice (n=10) maintained on the standard chow diet was also treated with TBS vehicle and followed as a dietary control. Fat volumes were determined by microCT for a subset of mice (n=4 per group) whose percentages of total body fat, as determined by nuclear magnetic resonance (NMR) analysis, were closest to group means (all mice were subjected to NMR analysis).

Figure 20:
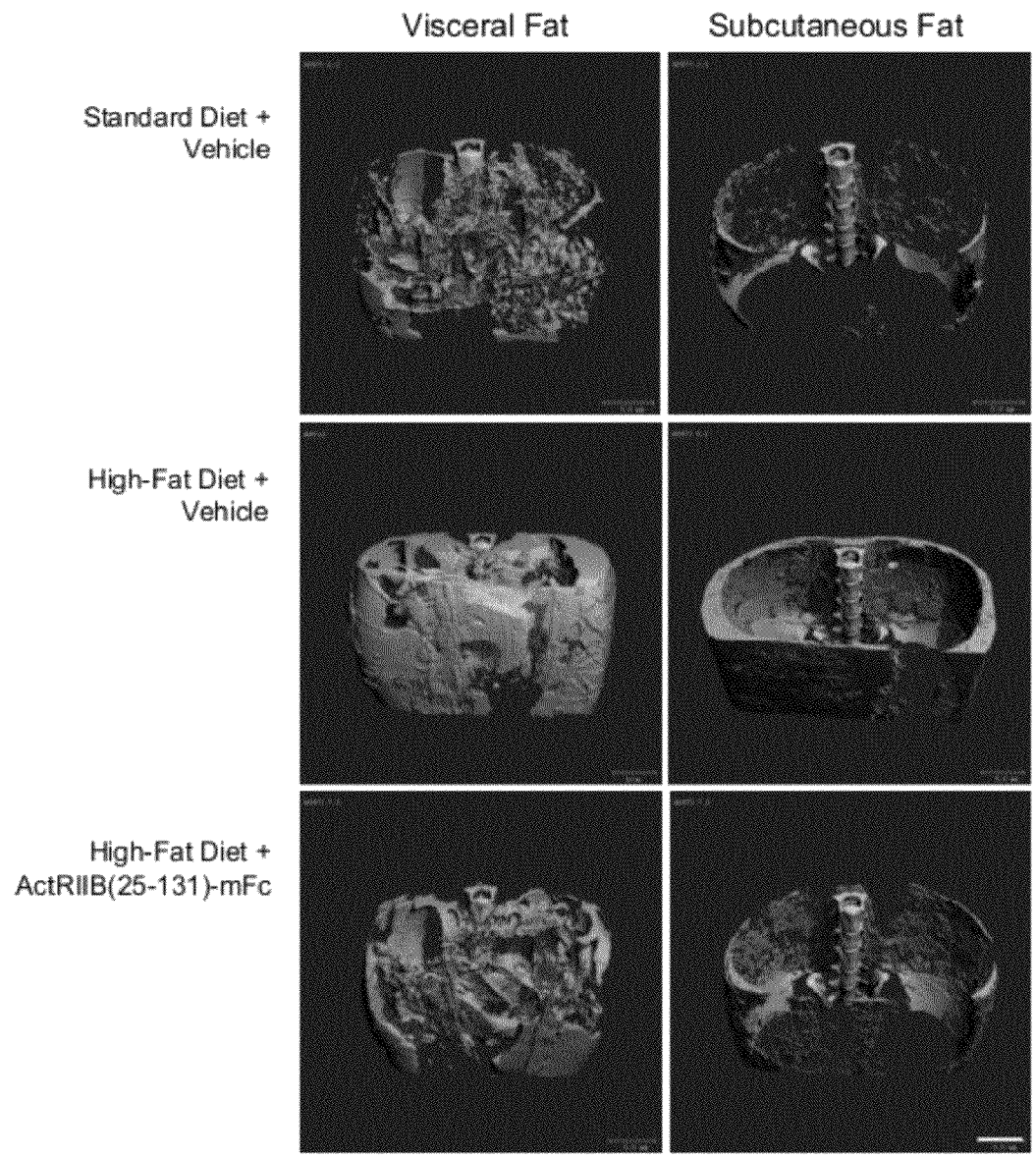
FIG. 20 shows the effect of ActRIIB(25-131)-mFc treatment for 35 days on the distribution of abdominal fat in a mouse model of diet-induced obesity. Visceral and subcutaneous fat depots were detected and differentiated in vivo by micro-computed tomography (microCT) encompassing spinal cord segments T13-L5. N=4 per group; scale bar=5 mm Compared to controls fed a high-fat diet, ActRIIB(25-131)-mFc treatment reduced the volume of both visceral and subcutaneous depots of abdominal fat.
Figure 21:
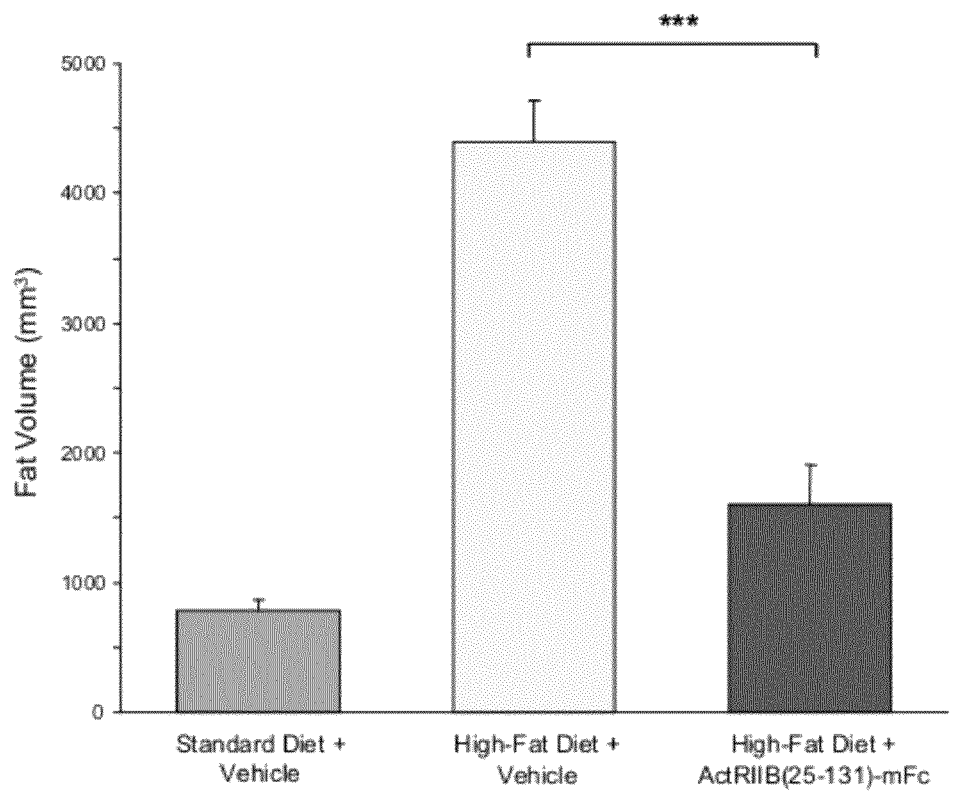
FIG. 21 shows the effect of ActRIIB(25-131)-mFc treatment for 60 days on the volume of visceral fat as determined by microCT in a mouse model of diet-induced obesity. Data are means±SEM; n=4 per group; ***, P<0.001. In mice fed a high-fat diet, ActRIIB(25-131)-mFc reduced the volume of visceral fat by more than 60% compared to vehicle.
Figure 22:
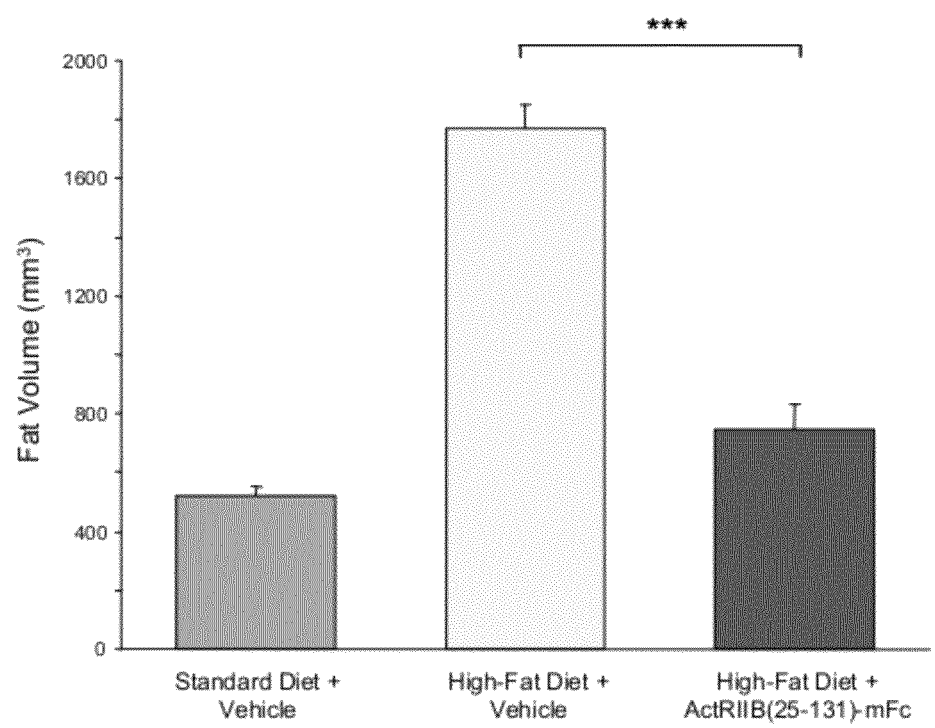
FIG. 22 shows the effect of ActRIIB(25-131)-mFc treatment for 60 days on the volume of abdominal subcutaneous fat as determined by microCT in a mouse model of diet-induced obesity. Data are means±SEM; n=4 per group; ***, P<0.001. In mice fed a high-fat diet, ActRIIB(25-131)-mFc reduced the volume of subcutaneous fat by nearly 60% compared to vehicle.

Visceral fat and abdominal subcutaneous fat both varied markedly in size with diet and ActRIIB(25-131)-mFc treatment. Three-dimensional reconstruction of microCT images obtained partway through the study (35 days) demonstrates that the depots of visceral fat and subcutaneous fat both expanded as a result of the high-fat diet and that ActRIIB(25-131)-mFc largely reversed those increases (FIG. 20). When analyzed quantitatively at study conclusion (60 days), the effect of ActRIIB(25-131)-mFc compared to high-fat diet alone was highly significant for both visceral fat (FIG. 21) and abdominal subcutaneous fat (FIG. 22).

Example 10

Figure 23:
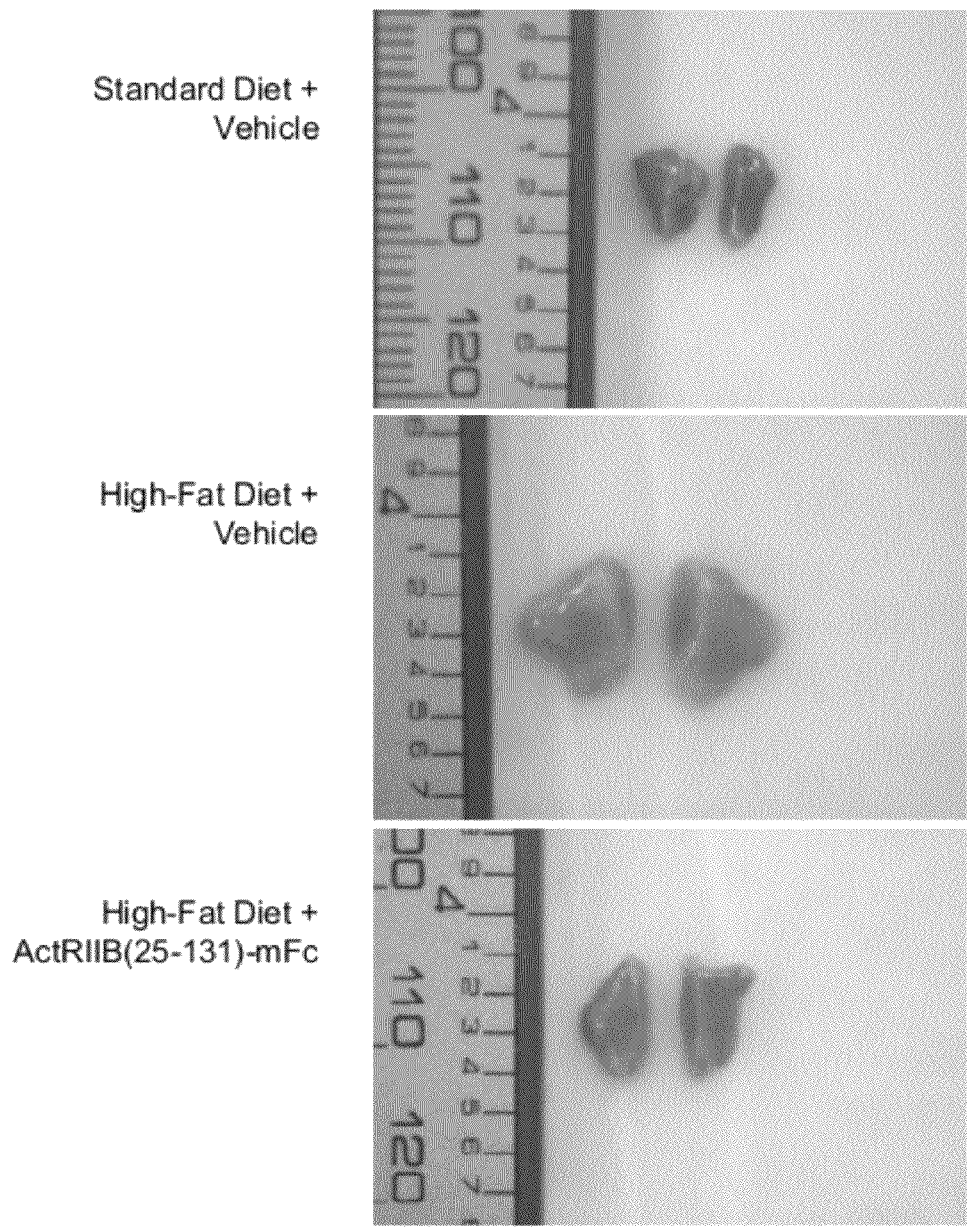
FIG. 23 shows photographs of bilateral pairs of interscapular brown fat depots as a function of diet and ActRIIB(25-131)-mFc treatment for 60 days in a mouse model of diet-induced obesity. High-fat diet increased the size and lightened the color of the depots, whereas ActRIIB(25-131)-mFc largely reversed these changes.
Figure 24:
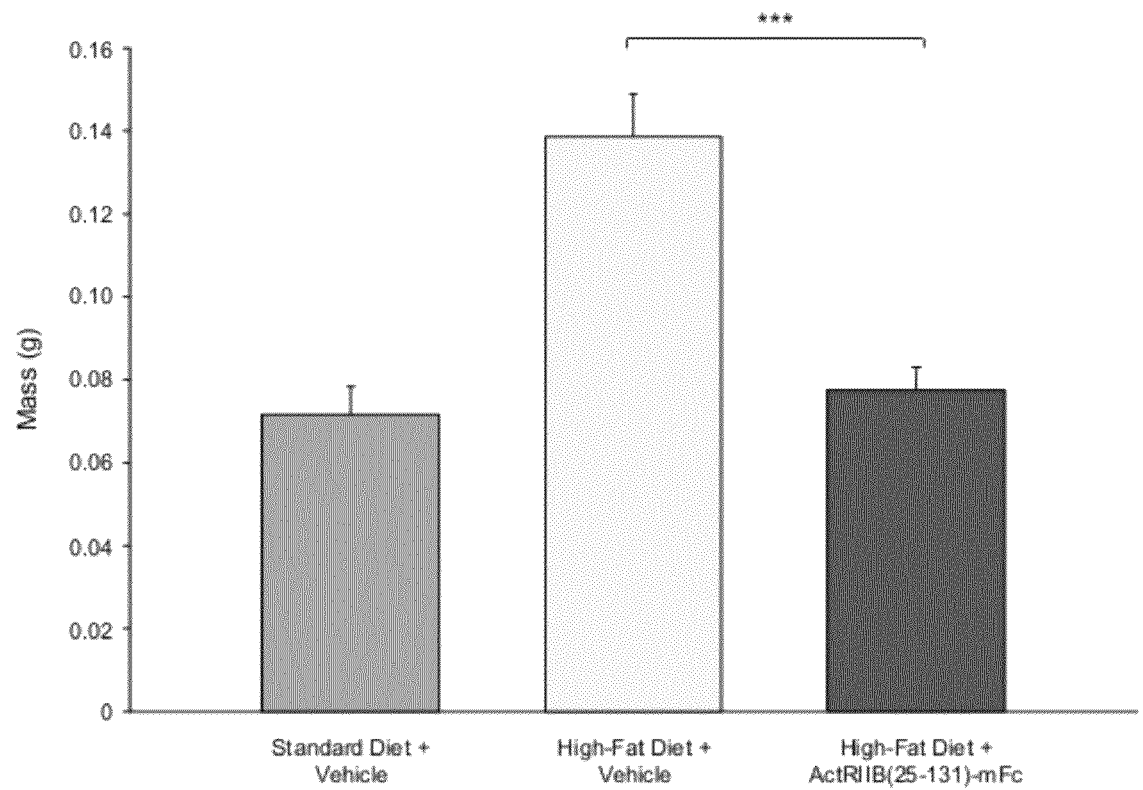
FIG. 24 depicts the effect of ActRIIB(25-131)-mFc treatment for 60 days on the mass of interscapular brown fat in a mouse model of diet-induced obesity. Data are means±SEM for combined left and right depots; ***, p<0.001. ActRIIB (25-131)-mFc reversed the effect of high-fat diet on the mass of this brown fat depot.
Figure 25:
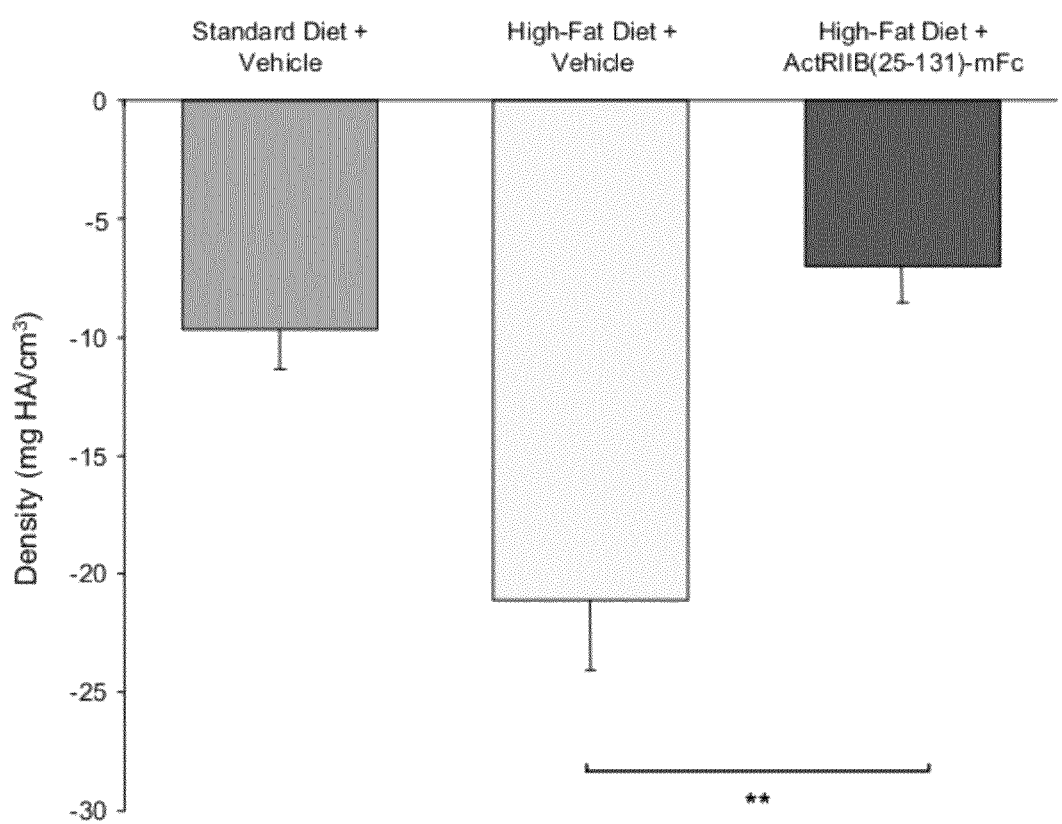
FIG. 25 depicts the effect of ActRIIB(25-131)-mFc treatment for 60 days on the density of interscapular brown fat as determined by microCT in a mouse model of diet-induced obesity. Data (means±SEM) are expressed in standardized units based on a positive value for the bone mineral hydroxyapatite (HA) and a value of zero for water; therefore, fat values are negative, with values for white fat typically close to −120. **, p<0.01. ActRIIB(25-131)-mFc completely reversed the effect of high-fat diet on the density of this brown fat depot.

Effect of ActRIIB(25-131)-mFc on Brown Fat Properties in Mouse Model of Diet-Induced Obesity In the study described in Example 9, Applicants also investigated effects of ActRIIB(25-131)-mFc on properties of intrascapular brown fat depots under high-fat dietary conditions. Compared to the standard diet, the high-fat diet produced several changes in the interscapular depot of brown adipose tissue, and ActRIIB(25-131)-mFc treatment either completely or largely reversed each of these changes. Specifically, high-fat diet caused a pronounced enlargement of the interscapular depot as well as lightening of its color from red to pink (FIG. 23). This diet-induced enlargement reflected a doubling of the mass (FIG. 24) and a reduction in the density (FIG. 25) of brown fat depots. Depot density was determined by micro-computed tomography (microCT) in situ for a subset of mice (n=4 per group) whose percentages of total body fat, as determined by nuclear magnetic resonance (NMR) analysis, were closest to the group means (all mice were subjected to NMR analysis). ActRIIB(25-131)-mFc treatment completely reversed diet-induced changes in brown fat mass (FIG. 24) and density (FIG. 25), while largely reversing diet-induced changes in size and color of the depot (FIG. 23). These results indicate that, under high-fat dietary conditions, ActRIIB(25-131)-mFc largely or completely restores properties likely to correlate with healthy brown fat function and thus improves the quality of brown fat as it decreases the overall size of brown fat depots.

Example 11

Effects of ActRIIB(25-131)-mFc on Muscle, Bone, Fat, and Metabolic Hormones in Mouse Model of Aging Body composition changes with aging in a predictable manner. Normal age-dependent decline in muscle mass and strength, known as sarcopenia, begins around age 30 and accelerates after age 60 (Stenholm et al, 2008, Curr Opin Clin Nutr Metab Care 11:693-700). Bone mass and strength exhibit a similar decline with age, leading to an increased risk of osteoporosis in the elderly. Whole-body fat mass increases with age until around age 70, then declines in absolute terms but remains a roughly constant proportion of total body mass (Cartwright et al., 2007, Exp Gerontol 42:463-471). Based on efficacy observed in other models and described herein, Applicants investigated effects of ActRIIB(25-131)-mFc on muscle, bone, fat, and insulin levels in a mouse model of aging. Nineteen-month-old male C57BL/6 mice were given unlimited access to a standard chow diet and treated with ActRIIB(25-131)-mFc (n=16), at 10 mg/kg, s.c., or TBS vehicle (n=15) twice per week for 8 weeks. As a frame of reference, median life expectancy in this mouse strain was previously found to be approximately 27 months under standard dietary conditions (Turturro et al., 2002, J Gerontol A Biol Sci Med Sci 57:B379-389).

Figure 26:
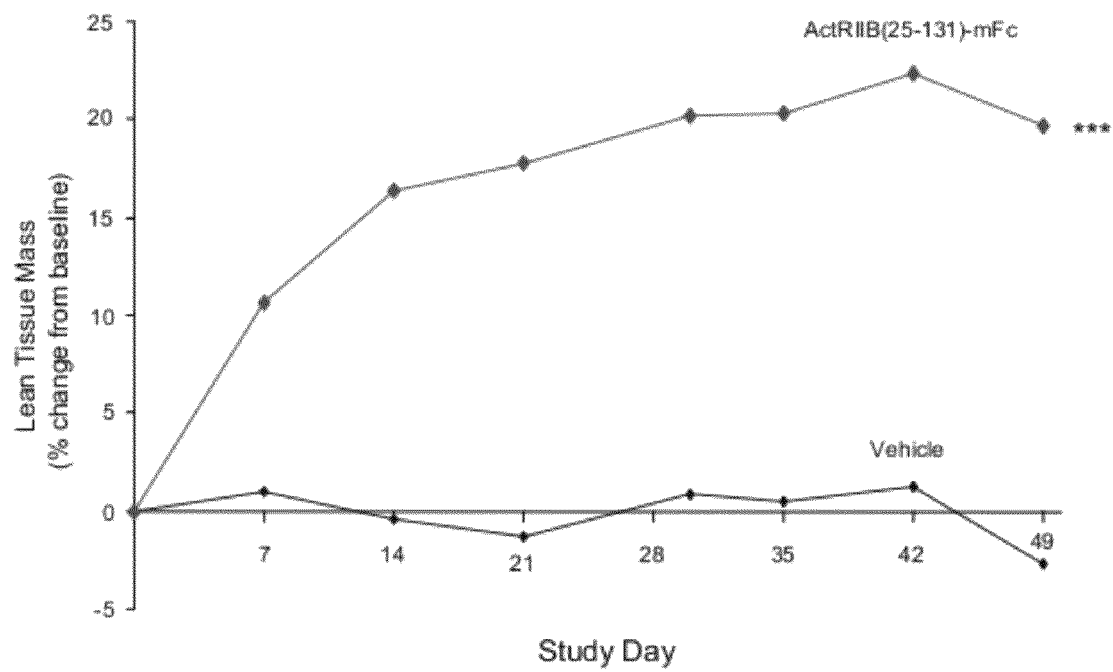
FIG. 26 depicts the effect of ActRIIB(25-131)-mFc treatment on lean tissue mass as determined in a mouse model of aging by nuclear magnetic resonance (NMR) analysis at multiple time points. Data are means of 10-15 mice per group per time point; ***, P<0.001 vs. vehicle at same time point. After 7 weeks of dosing, lean tissue mass in aged mice treated with ActRIIB(25-131)-mFc increased nearly 20% from baseline, in contrast to essentially unchanged values in vehicle-treated controls.
Figure 27:
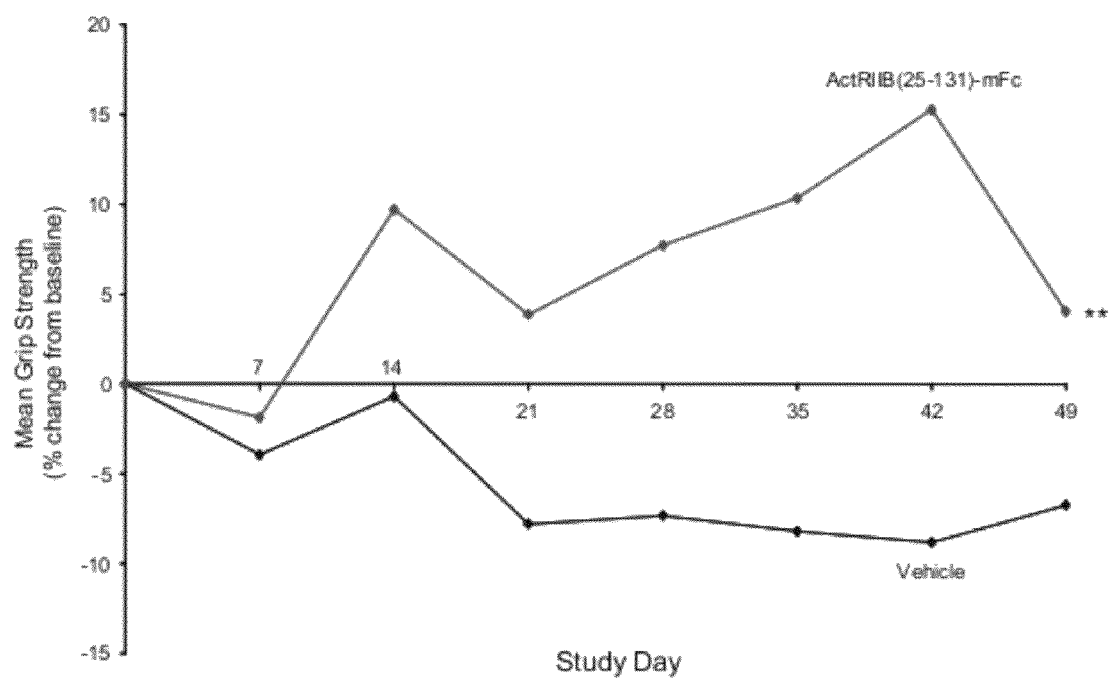
FIG. 27 depicts the effect of ActRIIB(25-131)-mFc treatment on forelimb grip strength as determined at multiple time points in a mouse model of aging. Data are means of 13-15 mice per group per time point; **, P<0.01 vs. vehicle at same time point. Mice treated with ActRIIB(25-131)-mFc displayed an overall trend of increasing grip strength across the study, in contrast to the decline in grip strength observed in vehicle controls over the same interval.

ActRIIB(25-131)-mFc treatment generated a series of notable changes in body composition and metabolic hormone effects in these aged mice. As determined by whole-body NMR analysis, lean tissue mass was essentially unchanged in control mice over the course of the study, whereas in ActRIIB(24-131)-mFc-treated mice it increased progressively to almost 20% above baseline by 7 weeks (FIG. 26). Consistent with this whole-body effect, ActRIIB(25-131)-mFc also significantly increased the mass of individual muscle groups, including the pectoralis (increased 55%), rectus femoris (40%), triceps (40%), and gastrocnemius (28%), compared to vehicle-treated controls at 8 weeks Importantly, ActRIIB(25-131)-mFc treatment improved neuromuscular function, as determined by forelimb grip strength testing according to an established protocol (http://jaxservices.jax.org/phenotyping/gripstrength_protocol.html) (FIG. 27).

Figure 28:
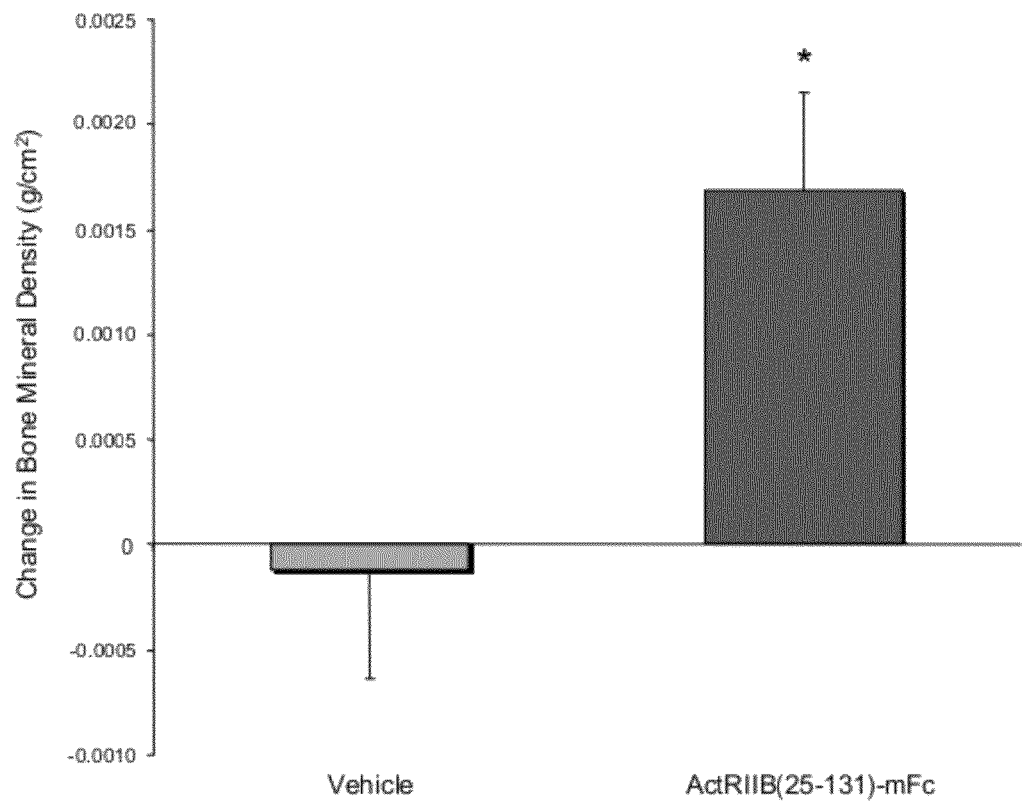
FIG. 28 depicts the effect of ActRIIB(25-131)-mFc treatment for 8 weeks on bone mineral density as determined in a mouse model of aging by dual energy x-ray absorptiometry (DEXA). Data are means±SEM; *, P<0.05. Bone mineral density in aged mice treated with ActRIIB(25-131)-mFc (n=10) increased significantly compared to vehicle-treated controls (n=14).

Several bone-related parameters improved with ActRIIB(25-131)-mFc treatment in aged mice. As determined by DEXA analysis at baseline and 8-week time points, ActRIIB(25-131)-mFc increased whole-body bone mineral density over the course of the study, whereas controls were essentially unchanged (FIG. 28). In addition, microCT analysis of the proximal tibia demonstrated that ActRIIB(25-131)-mFc treatment for 8 weeks doubled the bone volume fraction of the proximal tibia compared to controls (P<0.01).

Figure 29:
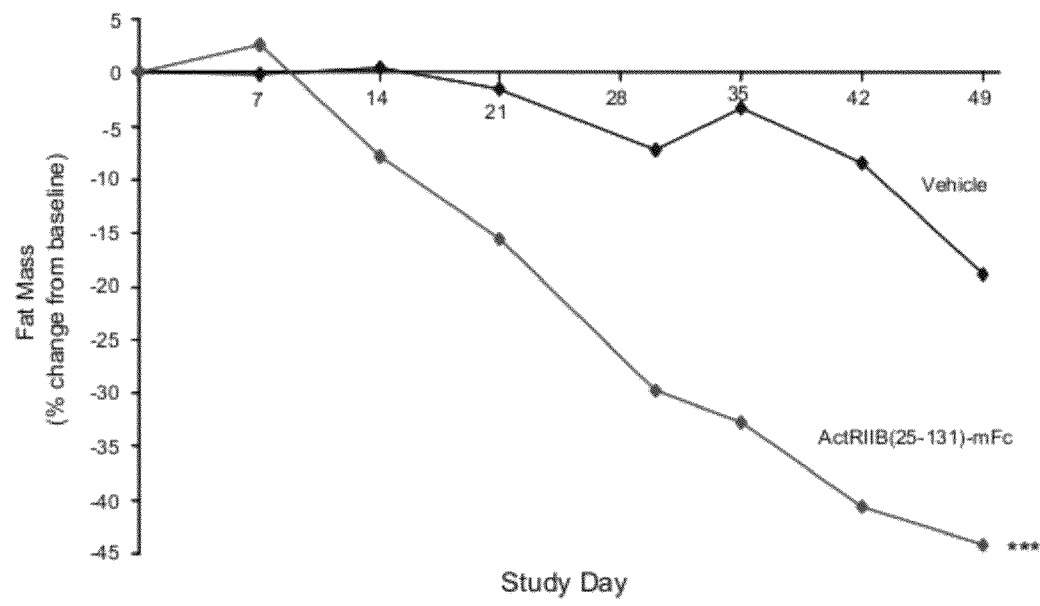
FIG. 29 depicts the effect of ActRIIB(25-131)-mFc treatment on whole-body fat mass as determined in a mouse model of aging by NMR analysis at multiple time points. Data are means of 10-15 mice per group per time point. ***, P<0.001 vs. vehicle at same time point. After 7 weeks of dosing, fat mass in aged mice treated with ActRIIB(25-131)-mFc exhibited a percent decrease from baseline more than twice the magnitude of that in vehicle-treated controls.

ActRIIB(25-131)-mFc exerted major effects on fat in aged mice. As determined by NMR analysis at multiple time points, there was a progressive decline in whole-body fat mass in vehicle-treated controls over the course of the study (FIG. 29), consistent with findings from humans in advanced old age. ActRIIB(25-131)-mFc treatment accelerated this change, triggering a decrease of twice the magnitude observed in controls (−44% vs. −19%, respectively) (FIG. 29). By the terminal time point, ActRIIB(25-131)-mFc significantly reduced the mass of the individual epididymal, inguinal, and retroperitoneal depots of white fat by amounts ranging from 48-54%. Interestingly, ActRIIB(25-131)-mFc treatment also reduced the mass of the interscapular brown fat depots by nearly 45% (P<0.05), similar to results obtained for this tissue in the mouse model of dietary obesity (Example 10). Finally, as determined by microCT analysis in a representative subset of mice (n=4) from each group, ActRIIB(25-131)-mFc reduced the volume of the visceral component of abdominal fat by 65% (P<0.01) and the subcutaneous component of abdominal fat by 49% (P<0.01). Hence, the critical visceral fat compartment was strongly targeted by ActRIIB(25-131)-mFc in this model of aging.

Figure 30:
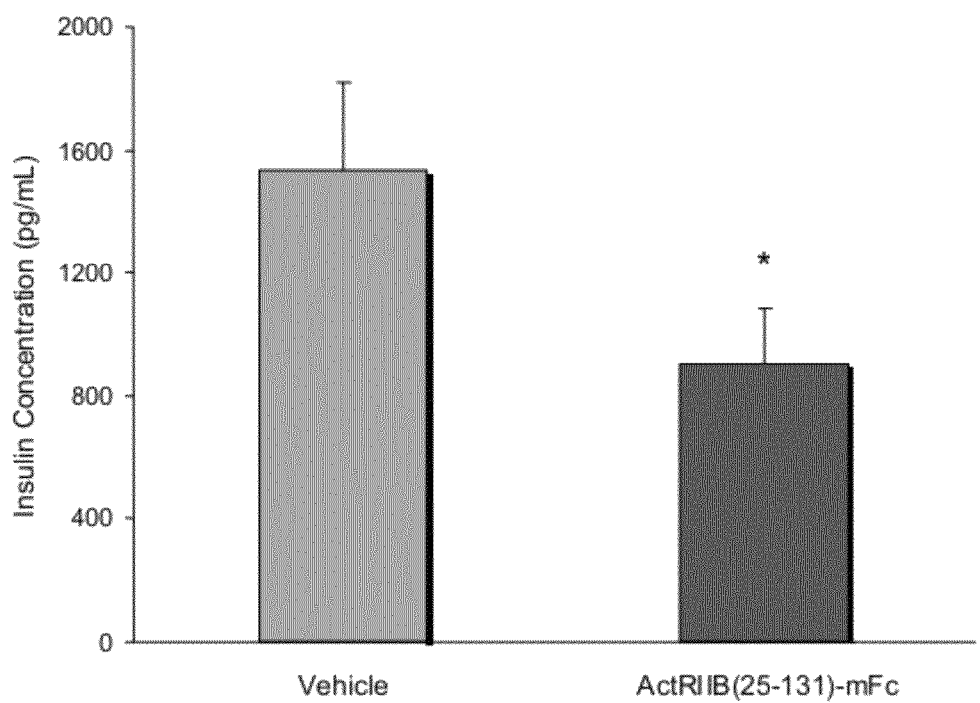
FIG. 30 depicts the effect of ActRIIB(25-131)-mFc treatment for 8 weeks on serum insulin concentrations in a mouse model of aging. Data are means±SEM; *, P<0.05. Insulin concentrations in aged mice treated with ActRIIB(25-131)-mFc (n=10) were reduced by more than 40% compared to vehicle-treated controls (n=14).
Figure 31:
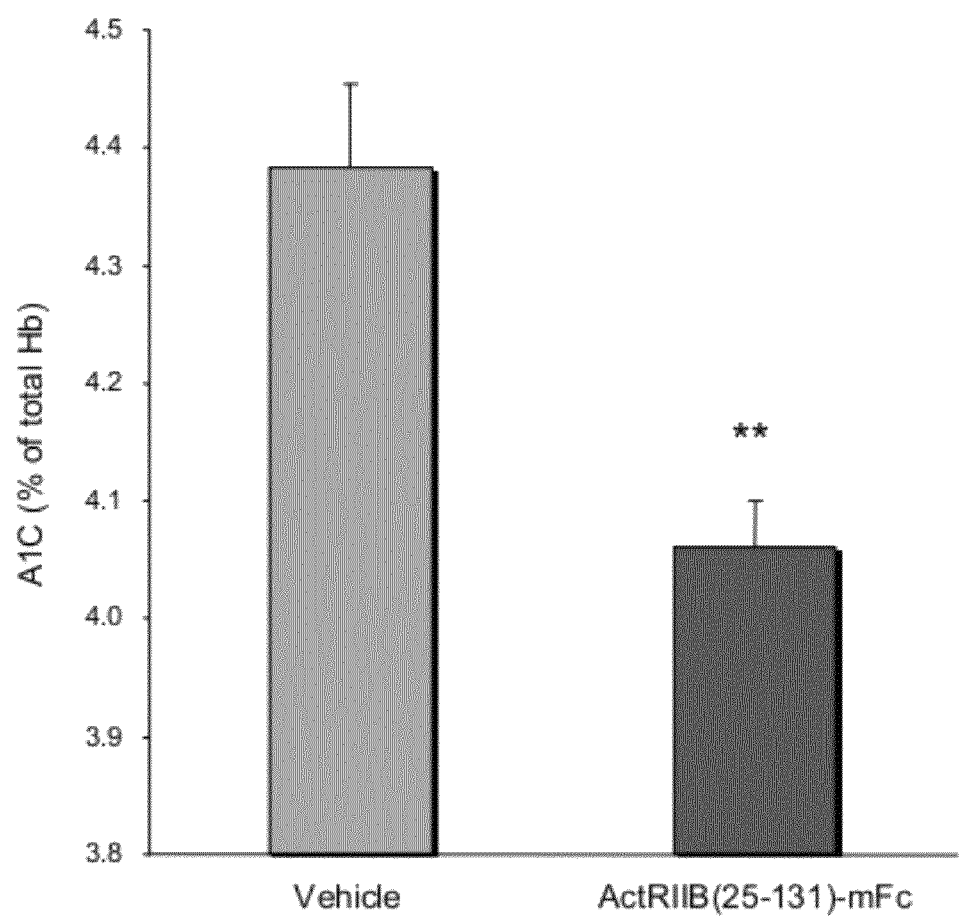
FIG. 31 depicts the effect of ActRIIB(25-131)-mFc treatment for 8 weeks on circulating glycated hemoglobin (A1C) concentrations. Data are means±SEM; n=5-6 per group; **, P<0.01. ActRIIB(25-131)-mFc significantly reduced concentrations of glycated hemoglobin, a widely accepted indicator of average blood glucose concentrations over an extended period.

ActRIIB(25-131)-mFc also produced beneficial changes in important metabolic hormones in aged mice. Eight weeks of treatment with ActRIIB(25-131)-mFc nearly doubled circulating adiponectin concentrations (P<0.001) and reduced circulating insulin concentrations by more than 40% (FIG. 30). An elevated fasting insulin concentration (hyperinsulinemia) is a widely accepted surrogate measure of insulin resistance (Weyer et al., 2000, Diabetes 49:2094-2101), and increased adiponectin concentrations are likely contributing to improved insulin sensitivity in the present study. Glycated hemoglobin (A1C) concentrations were significantly reduced by ActRIIB(25-131)-mFc in this study (FIG. 31), thereby providing additional evidence for improved glucose regulation with ActRIIB(25-131)-mFc treatment in this model of aging.

Example 12

Effect of ActRIIB(25-131)-hFc on Lean Tissue in Mouse Model of Cancer Cachexia

Figure 32:
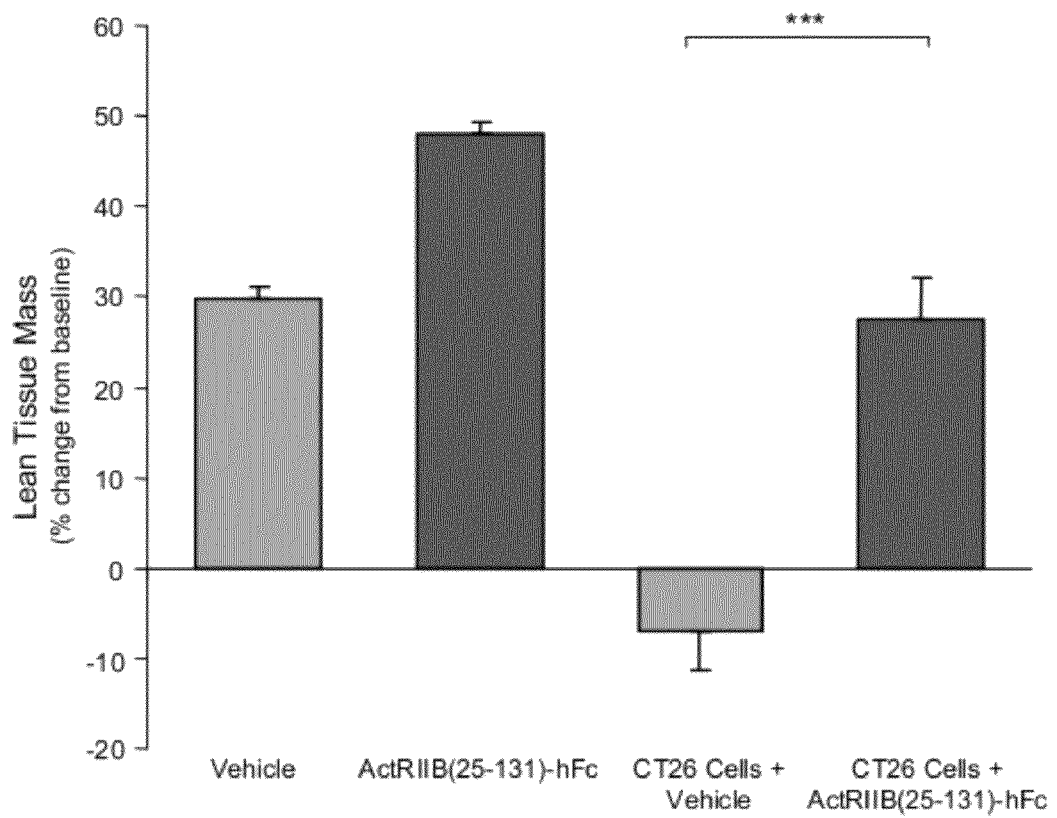
FIG. 32 depicts the effect of ActRIIB(25-131)-hFc treatment for 5 weeks on lean tissue mass as determined by NMR analysis in a mouse model of cancer cachexia. Data are means±SEM; ***, P<0.001. In tumor-implanted mice, vehicle treatment (n=7) was associated with a 7% loss in lean tissue mass, whereas ActRIIB(25-131)-hFc treatment (n=12) caused a 27% gain in lean tissue mass from baseline.

Cachexia is undesired weight loss resulting from loss of muscle and adipose tissue. Many tumors are associated with loss of appetite and severe muscle loss, and patients exhibiting cachexia have a poorer prognosis than non-cachectic patients. Since the colon-cancer cell line CT26 induces profound cachexia in mice, ActRIIB(25-131)-hFc was tested in this mouse model for potential effects on xenograft-induced cachexia. Eight-week-old BALB/c mice were injected subcutaneously with $10^6$ Colon-26 adenocarcinoma (CT26) cells per mouse. Two weeks after tumor implantation, treatment was initiated with ActRIIB(25-131)-hFc (n=15), at 10 mg/kg, s.c., or Tris-buffered-saline (TBS) vehicle (n=13) twice per week. Additional groups of BALB/c mice did not receive CT26 cells but were treated with ActRIIB(25-131)-hFc or vehicle as above. Treatment with ActRIIB(25-131)-hFc resulted in a significant increase in body weight that was maintained across the study. At 5 weeks post tumor implantation, vehicle-treated mice exhibited a 7% loss of lean tissue mass from baseline, as determined by NMR analysis, whereas mice treated with ActRIIB(25-131)-hFc exhibited a 27% increase in lean mass from baseline (FIG. 32). Fat mass did not differ significantly between the groups. These results demonstrate that ActRIIB(25-131)-hFc can alleviate cachexia in tumor-bearing mice and could be an effective therapy for treating cachexia in cancer patients.

Taken together, these data indicate that ActRIIB(25-131)-hFc fusion protein can be used as an antagonist of signaling by TGF-family ligands to reverse many pathological metabolic changes associated with diet-induced obesity, and thereby, to treat metabolic conditions exacerbated by high caloric intake. Moreover, ActRIIB(25-131)-hFc can be used to treat pathologic metabolic changes associated with aging or cancer cachexia.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. An isolated nucleic acid comprising a nucleic acid sequence that hybridizes to the complement of nucleotides 73-396 of SEQ ID NO:6 in the presence of 6.0× sodium/sodium citrate (SSC) at 45° C. followed by a wash in 2.0×SSC at 65° C.

2. The nucleic acid of claim 1, wherein the nucleic acid comprises nucleotides 73-396 of SEQ ID NO:6.

3. A cultured cell comprising the nucleic acid of claim 1.

4. The cultured cell of claim 3, wherein the cell is a mammalian cell.

5. The cultured cell of claim 3, wherein the cell is a CHO cell.

6. The nucleic acid of claim 1, wherein the nucleic acid comprises the nucleotide sequence of SEQ ID NO:6.

7. The nucleic acid of claim 1, wherein the nucleic acid comprises a nucleotide sequence encoding a polypeptide comprising amino acids 25-131 of SEQ ID NO:1.

8. The nucleic acid of claim 1, wherein the nucleic acid comprises a nucleotide sequence encoding a polypeptide comprising the amino acid sequence of SEQ ID NO:1.

9. The nucleic acid of claim 1, wherein the nucleic acid further comprises a nucleotide sequence encoding a tissue plasminogen activator (TPA) leader sequence.

* * * * *

SEQUENCE LISTING

```
<160> NUMBER OF SEQ ID NOS: 15

<210> SEQ ID NO 1
<211> LENGTH: 512
<212> TYPE: PRT
<213> ORGANISM: Homo sapiens

<400> SEQUENCE: 1

Met Thr Ala Pro Trp Val Ala Leu Ala Leu Leu Trp Gly Ser Leu Trp
1               5                   10                  15

Pro Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140
```

```
Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
            165                 170                 175

Gly Pro Pro Pro Ser Pro Leu Val Gly Leu Lys Pro Leu Gln Leu
        180                 185                 190

Leu Glu Ile Lys Ala Arg Gly Arg Phe Gly Cys Val Trp Lys Ala Gln
            195                 200                 205

Leu Met Asn Asp Phe Val Ala Val Lys Ile Phe Pro Leu Gln Asp Lys
        210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
            245                 250                 255

Leu Glu Val Glu Leu Trp Leu Ile Thr Ala Phe His Asp Lys Gly Ser
        260                 265                 270

Leu Thr Asp Tyr Leu Lys Gly Asn Ile Ile Thr Trp Asn Glu Leu Cys
            275                 280                 285

His Val Ala Glu Thr Met Ser Arg Gly Leu Ser Tyr Leu His Glu Asp
        290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
            325                 330                 335

Leu Ala Asp Phe Gly Leu Ala Val Arg Phe Glu Pro Gly Lys Pro Pro
        340                 345                 350

Gly Asp Thr His Gly Gln Val Gly Thr Arg Arg Tyr Met Ala Pro Glu
            355                 360                 365

Val Leu Glu Gly Ala Ile Asn Phe Gln Arg Asp Ala Phe Leu Arg Ile
        370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
            405                 410                 415

Glu Ile Gly Gln His Pro Ser Leu Glu Glu Leu Gln Glu Val Val Val
        420                 425                 430

His Lys Lys Met Arg Pro Thr Ile Lys Asp His Trp Leu Lys His Pro
            435                 440                 445

Gly Leu Ala Gln Leu Cys Val Thr Ile Glu Glu Cys Trp Asp His Asp
        450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
            485                 490                 495

Val Thr Ser Val Thr Asn Val Asp Leu Pro Pro Lys Glu Ser Ser Ile
        500                 505                 510
```

<210> SEQ ID NO 2
<211> LENGTH: 1539
<212> TYPE: DNA
<213> ORGANISM: Homo sapiens

<400> SEQUENCE: 2
atgacggcgc cctgggtggc cctcgccctc ctctggggat cgctgtggcc cggctctggg     60

```
cgtggggagg ctgagacacg ggagtgcatc tactacaacg ccaactggga gctggagcgc      120
accaaccaga gcggcctgga gcgctgcgaa ggcgagcagg acaagcggct gcactgctac      180
gcctcctggc gcaacagctc tggcaccatc gagctcgtga agaagggctg ctggctagat      240
gacttcaact gctacgatag caggagtgt gtggccactg aggagaaccc ccaggtgtac       300
```

```
cgtggggagg ctgagacacg ggagtgcatc tactacaacg ccaactggga gctggagcgc      120
accaaccaga gcggcctgga gcgctgcgaa ggcgagcagg acaagcggct gcactgctac      180
gcctcctggc gcaacagctc tggcaccatc gagctcgtga agaagggctg ctggctagat      240
gacttcaact gctacgatag caggagtgt  gtggccactg aggagaaccc ccaggtgtac      300
ttctgctgct gtgaaggcaa cttctgcaac gagcgcttca ctcatttgcc agaggctggg      360
ggcccggaag tcacgtacga gccaccccg  acagccccca ccctgctcac ggtgctggcc      420
tactcactgc tgcccatcgg gggcctttcc ctcatcgtcc tgctggcctt ttggatgtac      480
cggcatcgca agccccccta cggtcatgtg acatccatg  aggaccctgg gcctccacca      540
ccatcccctc tggtgggcct gaagccactg cagctgctgg agatcaaggc tcggggcgc      600
tttggctgtg tctggaaggc ccagctcatg aatgactttg tagctgtcaa gatcttccca      660
ctccaggaca agcagtcgtg gcagagtgaa cgggagatct tcagcacacc tggcatgaag      720
cacgagaacc tgctacagtt cattgctgcc gagaagcgag gctccaacct cgaagtagag      780
ctgtggctca tcacggcctt ccatgacaag ggctcccctca cggattaccc tcaaggggaac   840
atcatcacat ggaacgaact gtgtcatgta gcagagacga tgtcacgagg cctctcatac      900
ctgcatgagg atgtgccctg gtgccgtggc gagggccaca gccgtctat  tgcccacagg      960
gactttaaaa gtaagaatgt attgctgaag agcgacctca cagccgtgct ggctgactttt    1020
ggcttggctg ttcgatttga gccagggaaa cctccagggg acacccacgg acaggtaggc     1080
acgagacggt acatggctcc tgaggtgctc gagggagcca tcaacttcca gagagatgcc     1140
ttcctgcgca ttgacatgta tgccatgggg ttggtgctgt gggagcttgt gtctcgctgc     1200
aaggctgcag acggacccgt ggatgagtac atgctgccct ttgaggaaga gattggccag     1260
caccttcgt tggaggagct gcaggaggtg gtggtgcaca agaagatgag gcccaccatt      1320
aaagatcact ggttgaaaca cccgggcctg gcccagcttt gtgtgaccat cgaggagtgc     1380
tgggaccatg atgcagaggc tcgcttgtcc gcgggctgtg tggaggagcg ggtgtccctg     1440
attcggaggt cggtcaacgg cactacctcg gactgtctcg tttccctggt gacctctgtc     1500
accaatgtgg acctgccccc taaagagtca agcatctaa                            1539
```

<210> SEQ ID NO 3  
<211> LENGTH: 360  
<212> TYPE: PRT  
<213> ORGANISM: Artificial Sequence  
<220> FEATURE:  
<223> OTHER INFORMATION: Description of Artificial Sequence: Synthetic  
      polypeptide

<400> SEQUENCE: 3

Met Asp Ala Met Lys Arg Gly Leu Cys Cys Val Leu Leu Leu Cys Gly
1               5                   10                  15

Ala Val Phe Val Ser Pro Gly Ala Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Cys Glu Gly Glu Gln Asp Lys Arg Leu His Cys Tyr Ala Ser Trp
    50                  55                  60

Arg Asn Ser Ser Gly Thr Ile Glu Leu Val Lys Lys Gly Cys Trp Leu
65                  70                  75                  80

Asp Asp Phe Asn Cys Tyr Asp Arg Gln Glu Cys Val Ala Thr Glu Glu
                85                  90                  95

Asn Pro Gln Val Tyr Phe Cys Cys Cys Glu Gly Asn Phe Cys Asn Glu

```
            100                 105                 110
Arg Phe Thr His Leu Pro Glu Ala Gly Gly Pro Glu Val Thr Tyr Glu
        115                 120                 125

Pro Pro Pro Thr Gly Gly Thr His Thr Cys Pro Pro Cys Pro Ala
130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
        180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
        260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
        340                 345                 350

Ser Leu Ser Leu Ser Pro Gly Lys
        355                 360

<210> SEQ ID NO 4
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (73)..(396)

<400> SEQUENCE: 4
atggatgcaa tgaagagagg gctctgctgt gtgctgctgc tgtgtggagc agtcttcgtt      60
tcgcccggcg cc gct gag aca cgg gag tgc atc tac tac aac gcc aac tgg     111
              Ala Glu Thr Arg Glu Cys Ile Tyr Tyr Asn Ala Asn Trp
                1               5                  10 gag ctg gag cgc acc aac cag agc ggc ctg gag cgc tgc gaa ggc gag      159
Glu Leu Glu Arg Thr Asn Gln Ser Gly Leu Glu Arg Cys Glu Gly Glu
 15                  20                  25 cag gac aag cgg ctg cac tgc tac gcc tcc tgg cgc aac agc tct ggc      207
Gln Asp Lys Arg Leu His Cys Tyr Ala Ser Trp Arg Asn Ser Ser Gly
 30                  35                  40                  45 acc atc gag ctc gtg aag aag ggc tgc tgg cta gat gac ttc aac tgc      255
Thr Ile Glu Leu Val Lys Lys Gly Cys Trp Leu Asp Asp Phe Asn Cys
```

|  |  |  |  |  |  |  |  |  |  |  |  |  |
|---|---|---|---|---|---|---|---|---|---|---|---|---|
|  |  |  | 50 |  |  |  | 55 |  |  |  | 60 |  |
| tac | gat | agg | cag | gag | tgt | gtg | gcc | act | gag | gag | aac | ccc | cag | gtg | tac | 303 |
| Tyr | Asp | Arg | Gln | Glu | Cys | Val | Ala | Thr | Glu | Glu | Asn | Pro | Gln | Val | Tyr |  |
|  |  |  | 65 |  |  |  | 70 |  |  |  | 75 |  |
| ttc | tgc | tgc | tgt | gaa | ggc | aac | ttc | tgc | aac | gag | cgc | ttc | act | cat | ttg | 351 |
| Phe | Cys | Cys | Cys | Glu | Gly | Asn | Phe | Cys | Asn | Glu | Arg | Phe | Thr | His | Leu |  |
|  |  |  | 80 |  |  |  | 85 |  |  |  | 90 |  |
| cca | gag | gct | ggg | ggc | ccg | gaa | gtc | acg | tac | gag | cca | ccc | ccg | aca |  | 396 |
| Pro | Glu | Ala | Gly | Gly | Pro | Glu | Val | Thr | Tyr | Glu | Pro | Pro | Pro | Thr |  |  |
|  |  |  | 95 |  |  |  | 100 |  |  |  | 105 |  |

```
ggtggtggaa ctcacacatg cccaccgtgc ccagcacctg aactcctggg ggaccgtca      456
gtcttcctct ccccccaaa acccaaggac accctcatga tctcccggac ccctgaggtc      516
acatgcgtgg tggtggacgt gagccacgaa gaccctgagg tcaagttcaa ctggtacgtg      576
gacggcgtgg aggtgcataa tgccaagaca agccgcggg aggagcagta caacagcacg      636
taccgtgtgt cagcgtcct caccgtcctg caccaggact ggctgaatgg caaggagtac      696
aagtgcaagg tctccaacaa agccctccca gcccccatcg agaaaaccat ctccaaagcc      756
aaagggcagc cccgagaacc acaggtgtac accctgcccc catcccggga ggagatgacc      816
aagaaccagg tcagcctgac ctgcctggtc aaaggcttct atcccagcga catcgccgtg      876
gagtgggaga gcaatgggca gccggagaac aactacaaga ccacgcctcc cgtgctggac      936
tccgacggct ccttcttcct ctatagcaag ctcaccgtgg acaagagcag gtggcagcag      996
gggaacgtct tctcatgctc cgtgatgcat gaggctctgc acaaccacta cacgcagaag     1056
agcctctccc tgtccccggg taaatga                                          1083
```

<210> SEQ ID NO 5
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
tcatttaccc ggggacaggg agaggctctt ctgcgtgtag tggttgtgca gagcctcatg       60
catcacggag catgagaaga cgttcccctg ctgccacctg ctcttgtcca cggtgagctt      120
gctatagagg aagaaggagc cgtcggagtc cagcacggga ggcgtggtct tgtagttgtt      180
ctccggctgc ccattgctct cccactccac ggcgatgtcg ctgggataga agcctttgac      240
caggcaggtc aggctgacct ggttcttggt catctcctcc cgggatgggg gcagggtgta      300
cacctgtggt tctcggggct gcccttggc tttggagatg gttttctcga tggggctgg       360
gagggctttg ttggagacct tgcacttgta ctccttgcca ttcagccagt cctggtgcag      420
gacggtgagg acgctgacca cacggtacgt gctgttgtac tgctcctccc gcggcttgt       480
cttggcatta tgcacctcca cgccgtccac gtaccagttg aacttgacct cagggtcttc      540
gtggctcacg tccaccacca cgcatgtgac ctcaggggtc cgggagatca tgagggtgtc      600
cttgggtttt ggggggaaga ggaagactga cgtcccccc aggagttcag gtgctgggca      660
cggtgggcat gtgtgagttc caccacctgt cggggtggc tcgtacgtga cttccgggcc      720
cccagcctct ggcaaatgag tgaagcgctc gttgcagaag ttgccttcac agcagcagaa      780
gtacacctgg gggttctcct cagtggccac acactcctgc ctatcgtagc agttgaagtc      840
atctagccag cagcccttct tcacgagctc gatggtgcca gagctgttgc gccaggaggc      900
gtagcagtgc agccgcttgt cctgctcgcc ttcgcagcgc tccaggccgc tctggttggt      960
```

```
gcgctccagc tcccagttgg cgttgtagta gatgcactcc cgtgtctcag cggcgccggg      1020
cgaaacgaag actgctccac acagcagcag cacacagcag agccctctct tcattgcatc      1080
cat                                                                    1083
```

<210> SEQ ID NO 6
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (73)..(396)

<400> SEQUENCE: 6

```
atggatgcaa tgaagagagg gctctgctgt gtgctgctgc tgtgtggagc agtcttcgtt       60
tcgcccggcg cc gcc gaa acc cgc gaa tgt att tat tac aat gct aat tgg     111
               Ala Glu Thr Arg Glu Cys Ile Tyr Tyr Asn Ala Asn Trp
                1               5                  10 gaa ctc gaa cgg acg aac caa tcc ggg ctc gaa cgg tgt gag ggg gaa        159
Glu Leu Glu Arg Thr Asn Gln Ser Gly Leu Glu Arg Cys Glu Gly Glu
 15                  20                  25 cag gat aaa cgc ctc cat tgc tat gcg tcg tgg agg aac tcc tcc ggg        207
Gln Asp Lys Arg Leu His Cys Tyr Ala Ser Trp Arg Asn Ser Ser Gly
 30              35                  40                  45 acg att gaa ctg gtc aag aaa ggg tgc tgg ctg gac gat ttc aat tgt        255
Thr Ile Glu Leu Val Lys Lys Gly Cys Trp Leu Asp Asp Phe Asn Cys
                 50                  55                  60 tat gac cgc cag gaa tgt gtc gcg acc gaa gag aat ccg cag gtc tat        303
Tyr Asp Arg Gln Glu Cys Val Ala Thr Glu Glu Asn Pro Gln Val Tyr
             65                  70                  75 ttc tgt tgt tgc gag ggg aat ttc tgt aat gaa cgg ttt acc cac ctc        351
Phe Cys Cys Cys Glu Gly Asn Phe Cys Asn Glu Arg Phe Thr His Leu
         80                  85                  90 ccc gaa gcc ggc ggg ccc gag gtg acc tat gaa ccc ccg ccc acc             396
Pro Glu Ala Gly Gly Pro Glu Val Thr Tyr Glu Pro Pro Pro Thr
     95                 100                 105 ggtggtggaa ctcacacatg cccaccgtgc ccagcacctg aactcctggg ggaccgtca       456 gtcttcctct tccccccaaa acccaaggac accctcatga tctcccggac ccctgaggtc      516
acatgcgtgg tggtggacgt gagccacgaa gaccctgagg tcaagttcaa ctggtacgtg      576
gacggcgtgg aggtgcataa tgccaagaca aagccgcggg aggagcagta caacagcacg      636
taccgtgtgg tcagcgtcct caccgtcctg caccaggact ggctgaatgg caaggagtac      696
aagtgcaagg tctccaacaa agccctccca gcccccatcg agaaaaccat ctccaaagcc      756
aaagggcagc cccgagaacc acaggtgtac accctgcccc catcccggga ggagatgacc      816
aagaaccagg tcagcctgac ctgcctggtc aaaggcttct atcccagcga catcgccgtg      876
gagtgggaga gcaatgggca gccggagaac aactacaaga ccacgcctcc cgtgctggac      936
tccgacggct ccttcttcct ctatagcaag ctcaccgtgg acaagagcag gtggcagcag      996
gggaacgtct tctcatgctc cgtgatgcat gaggctctgc acaaccacta cacgcagaag     1056
agcctctccc tgtccccggg taaatga                                         1083
```

<210> SEQ ID NO 7
<211> LENGTH: 1083
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

| | | | | | |
|---|---|---|---|---|---|
| tcatttaccc | ggggacaggg | agaggctctt | ctgcgtgtag | tggttgtgca | gagcctcatg | 60 |
| catcacggag | catgagaaga | cgttcccctg | ctgccacctg | ctcttgtcca | cggtgagctt | 120 |
| gctatagagg | aagaaggagc | cgtcggagtc | cagcacggga | ggcgtggtct | tgtagttgtt | 180 |
| ctccggctgc | ccattgctct | cccactccac | ggcgatgtcg | ctgggataga | agcctttgac | 240 |
| caggcaggtc | aggctgacct | ggttcttggt | catctcctcc | cgggatgggg | gcagggtgta | 300 |
| cacctgtggt | tctcggggct | gccctttggc | tttggagatg | gttttctcga | tgggggctgg | 360 |
| gagggctttg | ttggagacct | tgcacttgta | ctccttgcca | ttcagccagt | cctggtgcag | 420 |
| gacggtgagg | acgctgacca | cacggtacgt | gctgttgtac | tgctcctccc | gcggctttgt | 480 |
| cttggcatta | tgcacctcca | cgccgtccac | gtaccagttg | aacttgacct | cagggtcttc | 540 |
| gtggctcacg | tccaccacca | cgcatgtgac | ctcagggtc | cgggagatca | tgagggtgtc | 600 |
| cttgggtttt | gggggggaaga | ggaagactga | cggtcccccc | aggagttcag | gtgctgggca | 660 |
| cggtgggcat | gtgtgagttc | caccaccggt | gggcgggggt | tcataggtca | cctcgggccc | 720 |
| gccggcttcg | gggaggtggg | taaaccgttc | attacagaaa | ttcccctcgc | aacaacagaa | 780 |
| atagacctgc | ggattctctt | cggtcgcgac | acattcctgg | cggtcataac | aattgaaatc | 840 |
| gtccagccag | cacccttcc | tgaccagttc | aatcgtcccg | gaggagttcc | tccacgacgc | 900 |
| atagcaatgg | aggcgtttat | cctgttcccc | ctcacaccgt | tcgagcccgg | attggttcgt | 960 |
| ccgttcgagt | tcccaattag | cattgtaata | aatacattcg | cgggtttcgg | cggcgccggg | 1020 |
| cgaaacgaag | actgctccac | acagcagcag | cacacagcag | agccctctct | tcattgcatc | 1080 |
| cat | | | | | | 1083 |

<210> SEQ ID NO 8
<211> LENGTH: 335
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

Glu Thr Arg Glu Cys Ile Tyr Tyr Asn Ala Asn Trp Glu Leu Glu Arg
1               5                  10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Gly Gly Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr

```
                130                 135                 140
Pro Glu Val Thr Cys Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
                180                 185                 190

Val Leu Thr Val Leu His Gln Asp Trp Leu Asn Gly Lys Glu Tyr Lys
                195                 200                 205

Cys Lys Val Ser Asn Lys Ala Leu Pro Ala Pro Ile Glu Lys Thr Ile
210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
                260                 265                 270

Gly Gln Pro Glu Asn Asn Tyr Lys Thr Thr Pro Pro Val Leu Asp Ser
                275                 280                 285

Asp Gly Ser Phe Phe Leu Tyr Ser Lys Leu Thr Val Asp Lys Ser Arg
                290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 9
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Asp or Ala
<220> FEATURE:
<221> NAME/KEY: MOD_RES
<222> LOCATION: (100)..(100)
<223> OTHER INFORMATION: Lys or Ala
<220> FEATURE:
<221> NAME/KEY: MOD_RES
<222> LOCATION: (212)..(212)
<223> OTHER INFORMATION: Asn or Ala

<400> SEQUENCE: 9

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Xaa Val Ser His Glu Asp
                35                  40                  45

Pro Glu Val Lys Phe Asn Trp Tyr Val Asp Gly Val Glu Val His Asn
50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Xaa Val Ser Asn Lys Ala Leu Pro Val Pro Ile Glu Lys
```

```
                    100                 105                 110
Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
        130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Xaa His Tyr Thr Gln Lys Ser Leu Ser Leu Ser Pro Gly
    210                 215                 220

Lys
225

<210> SEQ ID NO 10
<211> LENGTH: 348
<212> TYPE: DNA
<213> ORGANISM: Homo sapiens

<400> SEQUENCE: 10
tctgggcgtg gggaggctga gacacgggag tgcatctact acaacgccaa ctgggagctg     60
gagcgcacca accagagcgg cctggagcgc tgcgaaggcg agcaggacaa gcggctgcac    120
tgctacgcct cctggcgcaa cagctctggc accatcgagc tcgtgaagaa gggctgctgg    180
ctagatgact tcaactgcta cgataggcag gagtgtgtgg ccactgagga gaaccccag    240 gtgtacttct gctgctgtga aggcaacttc tgcaacgagc gcttcactca tttgccagag    300
gctgggggcc cggaagtcac gtacgagcca ccccgacag cccccacc                  348

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Gly Gly Gly Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Gly Gly Gly Gly
1               5

<210> SEQ ID NO 13
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      6xHis tag

<400> SEQUENCE: 13

His His His His His His
1               5

<210> SEQ ID NO 14
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Glu Thr Arg Glu Cys Ile Tyr Tyr Asn Ala Asn Trp Glu Leu Glu
1               5                   10                  15

Arg Thr Asn Gln Ser Gly Leu Glu Arg Cys Glu Gly Glu Gln Asp Lys
            20                  25                  30

Arg Leu His Cys Tyr Ala Ser Trp Arg Asn Ser Ser Gly Thr Ile Glu
        35                  40                  45

Leu Val Lys Lys Gly Cys Trp Leu Asp Asp Phe Asn Cys Tyr Asp Arg
    50                  55                  60

Gln Glu Cys Val Ala Thr Glu Glu Asn Pro Gln Val Tyr Phe Cys Cys
65                  70                  75                  80

Cys Glu Gly Asn Phe Cys Asn Glu Arg Phe Thr His Leu Pro Glu Ala
                85                  90                  95

Gly Gly Pro Glu Val Thr Tyr Glu Pro Pro Thr
            100                 105

<210> SEQ ID NO 15
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Glu Thr Arg Glu Cys Ile Tyr Tyr Asn Ala Asn Trp Glu Leu Glu
1               5                   10                  15

Arg Thr Asn Gln Ser Gly Leu Glu Arg Cys Glu Gly Glu Gln Asp Lys
            20                  25                  30

Arg Leu His Cys Tyr Ala Ser Trp Arg Asn Ser Ser Gly Thr Ile Glu
        35                  40                  45

Leu Val Lys Lys Gly Cys Trp Leu Asp Asp Phe Asn Cys Tyr Asp Arg
    50                  55                  60

Gln Glu Cys Val Ala Thr Glu Glu Asn Pro Gln Val Tyr Phe Cys Cys
65                  70                  75                  80

Cys Glu Gly Asn Phe Cys Asn Glu Arg Phe Thr His Leu Pro Glu Ala
                85                  90                  95

Gly Gly Pro Glu Val Thr Tyr Glu Pro Pro Thr
            100                 105
```